US010449267B2

(12) United States Patent
Lu et al.

(10) Patent No.: US 10,449,267 B2
(45) Date of Patent: Oct. 22, 2019

(54) SELF-ASSEMBLING UNDERWATER ADHESIVES

(71) Applicant: Massachusetts Institute of Technology, Cambridge, MA (US)

(72) Inventors: Timothy Kuan-Ta Lu, Cambridge, MA (US); Chao Zhong, Bedford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 122 days.

(21) Appl. No.: 14/540,872

(22) Filed: Nov. 13, 2014

(65) Prior Publication Data

US 2016/0220727 A1    Aug. 4, 2016

Related U.S. Application Data

(60) Provisional application No. 62/051,104, filed on Sep. 16, 2014, provisional application No. 61/903,824, filed on Nov. 13, 2013.

(51) Int. Cl.

| C07K 14/78 | (2006.01) |
|---|---|
| C08H 1/00 | (2006.01) |
| C09J 189/00 | (2006.01) |
| A61L 24/10 | (2006.01) |
| C07K 14/245 | (2006.01) |
| C07K 14/435 | (2006.01) |
| D01F 4/00 | (2006.01) |
| C09J 5/00 | (2006.01) |
| A61L 24/00 | (2006.01) |

(52) U.S. Cl.
CPC ........... *A61L 24/108* (2013.01); *A61L 24/001* (2013.01); *C07K 14/245* (2013.01); *C07K 14/43504* (2013.01); *C07K 14/43509* (2013.01); *C07K 14/78* (2013.01); *C08H 1/00* (2013.01); *C09J 5/00* (2013.01); *C09J 189/00* (2013.01); *D01F 4/00* (2013.01); *C07K 2319/00* (2013.01); *C07K 2319/70* (2013.01); *C07K 2319/73* (2013.01); *C07K 2319/735* (2013.01); *C09J 2489/00* (2013.01)

(58) Field of Classification Search
None
See application file for complete search history.

(56) References Cited

U.S. PATENT DOCUMENTS

| 7,622,550 B2 | 11/2009 | Cha et al. |
| 7,947,806 B2 | 5/2011 | Cha et al. |
| 2012/0202748 A1 | 8/2012 | Cha et al. |

FOREIGN PATENT DOCUMENTS

| WO | WO 2008/022774 A2 | 2/2008 |
| WO | WO 2008/150101 A2 | 12/2008 |
| WO | WO 2012/166906 A1 | 12/2012 |

OTHER PUBLICATIONS

Rudinger, In "Peptide Hormones" (ed. J.A. Parsons), University Park Press, Baltimore (1976), pp. 1-7.*
International Search Report and Written Opinion for PCT/US2014/065470, dated Nov. 2, 2015.
International Preliminary Report on PAtentability for PCT/US2014/065470, dated May 26, 2016.
Invitation to Pay Additional Fees for PCT/US2014/065470, dated Aug. 26, 2015.
Zhong et al., Biologically Inspired Engineering of Self-assembling Underwater Adhesives with Synthetic Biology. Society for Biomaterials Annual Meeting and Exposition 2014—Transactions of the 38th Annual Meeting. Abstract No. 805.
Zhong et al., Strong underwater adhesives made by self-assembling multi-protein nanofibres. Nat Nanotechnol. Oct. 2014;9(10):858-66. doi: 10.1038/nnano.2014.199. Epub Sep. 21, 2014.
Al-Hilaly et al., A central role for dityrosine crosslinking of Amyloid-β in Alzheimer's disease. Acta Neuropathol Commun. Dec. 18, 2013;1:83. doi: 10.1186/2051-5960-1-83.
Auslander et al., Programmable single-cell mammalian biocomputers. Nature. Jul. 5, 2012;487(7405):123-7. doi:10.1038/nature11149.
Barlow et al., Characterization of the adhesive plaque of the barnacle Balanus amphitrite: amyloid-like nanofibrils are a major component. Langmuir. May 4, 2010;26(9):6549-56. doi: 10.1021/la9041309.
Barnhart et al., Curli biogenesis and function. Annu Rev Microbiol. 2006;60:131-47.
Bilic et al., Injectable candidate sealants for fetal membrane repair: bonding and toxicity in vitro. Am J Obstet Gynecol. Jan. 2010;202(1):85. e1-9. doi: 10.1016/j.ajog.2009.07.051.
Brubaker et al., Biological performance of mussel-inspired adhesive in extrahepatic islet transplantation. Biomaterials. Jan. 2010;31(3):420-7. doi: 10.1016/j.biomaterials.2009.09.062.
Brubaker et al., the present and future of biologically inspired adhesive interfaces and materials. Langmuir. Jan. 31, 2012;28(4):2200-5. doi:10.1021/la300044v.
Chan et al., Protein amyloids develop an intrinsic fluorescence signature during aggregation. Analyst. Apr. 7, 2013;138(7):2156-62. doi: 10.1039/c3an36798c.
Chapman et al., Role of *Escherichia coli* curli operons in directing amyloid fiber formation. Science. Feb. 1, 2002;295(5556):851-5.
Chen et al., Synthesis and patterning of tunable multiscale materials with engineered cells. Nat Mater. May 2014;13(5):515-23. doi: 10.1038/nmat3912.
Cheng et al., Synthetic biology: an emerging engineering discipline. Annu Rev Biomed Eng. 2012;14:155-78. doi: 10.1146/annurev-bioeng-071811-150118.

(Continued)

*Primary Examiner* — Robert C Hayes
(74) *Attorney, Agent, or Firm* — Wolf, Greenfield & Sacks, P.C.

(57) ABSTRACT

Compositions, methods, and kits are provided which involve novel fusion protein-based adhesives for use in medical and marine applications. In some aspects, the novel fusion proteins comprise an adhesive domain (e.g., derived from an adhesive protein of a marine organism) and an amyloid domain (e.g., derived from a bacterial amyloid protein). Also provided are copolymers and fibers of the fusion proteins.

14 Claims, 67 Drawing Sheets

Specification includes a Sequence Listing.

(56) References Cited

OTHER PUBLICATIONS

Collinson et al., Structural predictions of AgfA, the insoluble fimbrial subunit of Salmonella thin aggregative fimbriae. J Mol Biol. Jul. 16, 1999;290(3):741-56.

Danner et al., Adhesion of mussel foot protein Mefp-5 to mica: an underwater superglue. Biochemistry. Aug. 21, 2012;51(33):6511-8. doi: 10.1021/bi3002538.

Del Mercato et al., Charge transport and intrinsic fluorescence in amyloid-like fibrils. Proc Natl Acad Sci U S A. Nov. 13, 2007;104(46):18019-24. Erratum in: Proc Natl Acad Sci U S A. Apr. 22, 2008;105(16):6208.

Demidova-Rice et al., Bioactive peptides derived from vascular endothelial cell extracellular matrices promote microvascular morphogenesis and wound healing in vitro. Wound Repair Regen. Jan.-Feb. 2011;19(1):59-70. doi: 10.1111/j.1524-475X.2010.00642.x.

Fowler et al., Functional amyloid—from bacteria to humans. Trends Biochem Sci. May 2007;32(5):217-24.

Goulter-Thorsen et al., CsgA production by *Escherichia coli* O157:H7 alters attachment to abiotic surfaces in some growth environments. Appl Environ Microbiol. Oct. 2011;77(20):7339-44. doi:10.1128/AEM.00277-11.

Heinig et al., STRIDE: a web server for secondary structure assignment from known atomic coordinates of proteins. Nucleic Acids Res. Jul. 1, 2004;32(Web Server issue):W500-2.

Hong et al., Cell-free protein synthesis from a release factor 1 deficient *Escherichia coli* activates efficient and multiple site-specific nonstandard amino acid Incorporation. ACS Synthetic Biology. 2014;3:398-409.

Hwang et al., Expression of functional recombinant mussel adhesive protein Mgfp-5 in *Escherichia coli*. Appl Environ Microbiol. Jun. 2004;70(6):3352-9.

Hwang et al., Practical recombinant hybrid mussel bioadhesive fp-151. Biomaterials. Aug. 2007;28(24):3560-8.

Hwang et al., Three intrinsically unstructured mussel adhesive proteins, mfp-1, mfp-2, and mfp-3: analysis by circular dichroism. Protein Sci. Nov. 2012;21(11):1689-95. doi: 10.1002/pro.2147.

Kamino et al., Significance of the conformation of building blocks in curing of barnacle underwater adhesive. FEBS J. May 2012;279(10):1750-60. doi: 10.1111/j.1742-4658.2012.08552.x.

Kamino, Underwater adhesive of marine organisms as the vital link between biological science and material science. Mar Biotechnol (NY). Mar.-Apr. 2008;10(2):111-21. doi: 10.1007/s10126-007-9076-3.

Knowles et al., Nanomechanics of functional and pathological amyloid materials. Nat Nanotechnol. Jul. 31, 2011;6(8):469-79. doi: 10.1038/nnano.2011.102.

Knowles et al., Nanostructured films from hierarchical self-assembly of amyloidogenic proteins. Nat Nanotechnol. Mar. 2010;5(3):204-7. doi: 10.1038/nnano.2010.26.

Knowles et al., Role of intermolecular forces in defining material properties of protein nanofibrils. Science. Dec. 21, 2007;318(5858):1900-3.

Kone et al., Selection of temperature intervals for parallel-tempering simulations. J Chem Phys. May 22, 2005;122(20):206101.

Lajoie et al., Genomically recoded organisms expand biological functions. Science. Oct. 18, 2013;342(6156):357-60. doi: 10.1126/science.1241459.

Lee et al., Mussel-inspired adhesives and coatings. Annu Rev Mater Res. Aug. 1, 2011;41:99-132.

Lee et al., Mussel-inspired surface chemistry for multifunctional coatings. Science. Oct. 19, 2007;318(5849):426-30.

Li et al., Biodegradable nanocomposites of amyloid fibrils and graphene with shape-memory and enzyme-sensing properties. Nat Nanotechnol. May 6, 2012;7(7):421-7. doi: 10.1038/nnano.2012.62.

Li et al., Single molecule evidence for the adaptive binding of Dopa to different wet surfaces. Langmuir. Apr. 22, 2014;30(15):4358-66. doi: 10.1021/la501189n.

Lu et al., Adhesion of mussel foot proteins to different substrate surfaces. J R Soc Interface. Feb. 2013;10(79):20120759. doi: 10.1098/rsif.2012.0759.

Luhrs et al., 3D structure of Alzheimer's amyloid-beta(1-42) fibrils. Proc Natl Acad Sci U S A. Nov. 29, 2005;102(48):17342-7.

Lv et al., Designed biomaterials to mimic the mechanical properties of muscles. Nature. May 6, 2010;465(7294):69-73. doi: 10.1038/nature09024.

Maji et al., Functional amyloids as natural storage of peptide hormones in pituitary secretory granules. Science. Jul. 17, 2009;325(5938):328-32. doi:10.1126/science.1173155.

Matos-Pérez et al., Polymer composition and substrate influences on the adhesive bonding of a biomimetic, cross-linking polymer. J Am Chem Soc. Jun. 6, 2012;134(22):9498-505. doi: 10.1021/ja303369p.

Oudhoff et al., Structure-activity analysis of histatin, a potent wound healing peptide from human saliva: cyclization of histatin potentiates molar activity 1,000-fold. FASEB J. Nov. 2009;23(11):3928-35. doi: 10.1096/fj.09-137588.

Padilla et al., Nanohedra: using symmetry to design self assembling protein cages, layers, crystals, and filaments. Proc Natl Acad Sci U S A. Feb. 27, 2001;98(5):2217-21.

Paz et al., Specific detection of quinoproteins by redox-cycling staining. J Biol Chem. Jan. 15, 1991;266:689-692.

Qian et al., Scaling up digital circuit computation with DNA strand displacement cascades. Science. Jun. 3, 2011;332(6034):1196-201. doi:10.1126/science.1200520.

Rhys Williams et al., Relative fluorescence quantum yields using a computer-controlled luminescence spectrometer. Analyst. 1983;108:1067-1071.

Sawaya et al., Atomic structures of amyloid cross-beta spines reveal varied steric zippers. Nature. May 24, 2007;447(7143):453-7.

Schneider et al., Self-assembling peptide nanofiber scaffolds accelerate wound healing. PLoS One. Jan. 9, 2008;3(1):e1410. doi:10.1371/journal.pone.0001410.

Shafiq et al., Bioinspired underwater bonding and debonding on demand. Angew Chem Int Ed Engl. Apr. 27, 2012;51(18):4332-5. doi: 10.1002/anie.201108629.

Shekaran et al., Nanoscale engineering of extracellular matrix-mimetic bioadhesive surfaces and implants for tissue engineering. Biochim Biophys Acta. Mar. 2011;1810(3):350-60. doi: 10.1016/j.bbagen.2010.04.006.

Shoemaker et al., Speeding molecular recognition by using the folding funnel: the fly-casting mechanism. Proc Natl Acad Sci U S A. Aug. 1, 2000;97(16):8868-73.

Sinclair et al., Generation of protein lattices by fusing proteins with matching rotational symmetry. Nat Nanotechnol. Jul. 31, 2011;6(9):558-62. doi: 10.1038/nnano.2011.122.

Smith, The fluorescence of dihydroxyphenylalanine: the effects of protonation-deprotonation. Coloration Technology. Nov. 1999;115(11):346-349.

Stewart et al., Natural underwater adhesives. J Polym Sci B Polym Phys. Jun. 2011;49(11):757-771.

Stewart, Protein-based underwater adhesives and the prospects for their biotechnological production. Appl Microbiol Biotechnol. Jan. 2011;89(1):27-33. doi: 10.1007/s00253-010-2913-8.

Sugase et al., Mechanism of coupled folding and binding of an intrinsically disordered protein. Nature. Jun. 21, 2007;447(7147):1021-5.

Taylor, Chemoenzymatic synthesis of peptidyl 3,4-dihydroxyphenylalanine for structure-activity relationships in marine invertebrate polypeptides. Anal Biochem. Mar. 1, 2002;302(1):70-4.

Von Der Mark et al., Nanoscale engineering of biomimetic surfaces: cues from the extracellular matrix. Cell Tissue Res. Jan. 2010;339(1):131-53. doi: 10.1007/s00441-009-0896-5.

Waite et al., Assay of dihydroxyphenylalanine (dopa) in invertebrate structural proteins. Methods Enzymol. 1984;107:397-413.

Wang et al., Gatekeeper residues in the major curlin subunit modulate bacterial amyloid fiber biogenesis. Proc Natl Acad Sci U S A. Jan. 5, 2010;107(1):163-8. doi: 10.1073/pnas.0908714107.

Wasmer et al., Amyloid fibrils of the HET-s(218-289) prion form a beta solenoid with a triangular hydrophobic core. Science. Mar. 14,

(56) References Cited

OTHER PUBLICATIONS

2008;319(5869):1523-6. doi:10.1126/science.1151839. Erratum in: Science. Apr. 4, 2008;320(5872):50.

Weber et al., Emerging biomedical applications of synthetic biology. Nat Rev Genet. Nov. 29, 2011;13(1):21-35. doi: 10.1038/nrg3094.

Wei et al., Hydrophobic enhancement of Dopa-mediated adhesion in a mussel foot protein. J Am Chem Soc. Jan. 9, 2013;135(1):377-83. doi: 10.1021/ja309590f.

Wu et al., Quantitative analysis of amyloid-integrated biofilms formed by uropathogenic *Escherichia coli* at the air-liquid interface. Biophys J. Aug. 8, 2012;103(3):464-71. doi: 10.1016/j.bpj.2012.06.049.

Yang et al., Development of aliphatic biodegradable photoluminescent polymers. Proc Natl Acad Sci U S A. Jun. 23, 2009;106(25):10086-91. doi:10.1073/pnas.0900004106. Erratum in: Proc Natl Acad Sci U S A. Jul. 14, 2009;106(28):11818.

Yin et al., Development of mussel adhesive polypeptide mimics coating for in-situ inducing re-endothelialization of intravascular stent devices. Biomaterials. May 2009;30(14):2764-73. doi:10.1016/j.biomaterials.2009.01.039.

Yu et al., Adaptive hydrophobic and hydrophilic interactions of mussel foot proteins with organic thin films. Proc Natl Acad Sci U S A. Sep. 24, 2013;110(39):15680-5. doi: 10.1073/pnas.1315015110.

\* cited by examiner

FIG. 2A
FIG. 2B
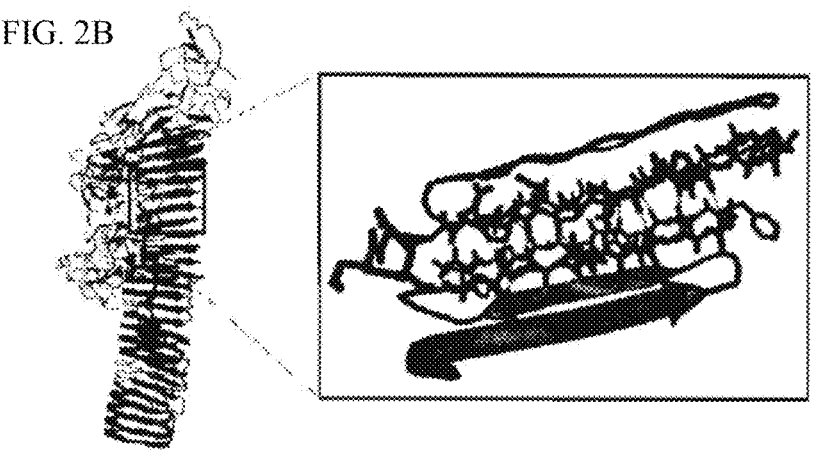
FIG. 2C
FIG. 2D
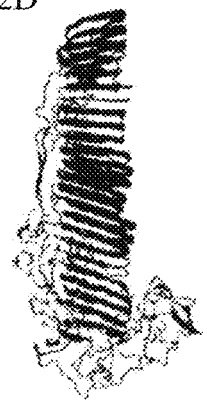
FIG. 2E
|  | Mfp3 domain | Mfp5 domain |
|---|---|---|
| Fraction of ($\alpha$) | 0.00± 0.004 | 0.00± 0.006 |
| Fraction of ($\beta$) | 0.23± 0.07 | 0.30± 0.05 |

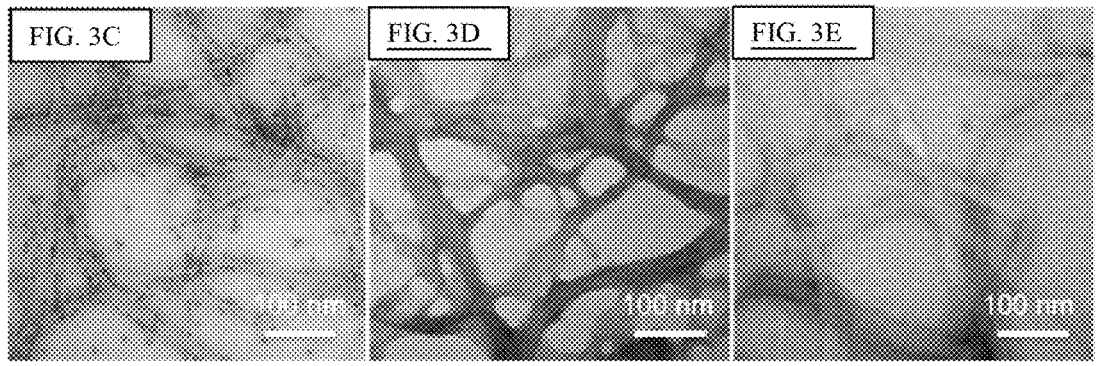
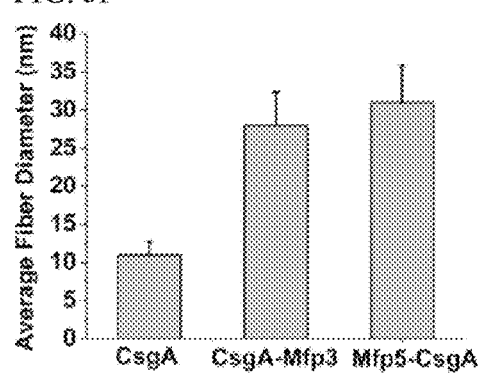
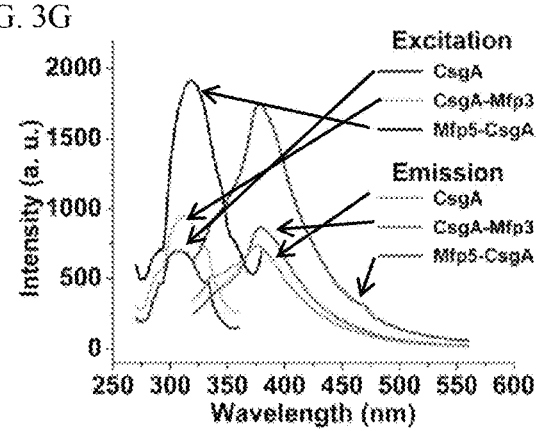
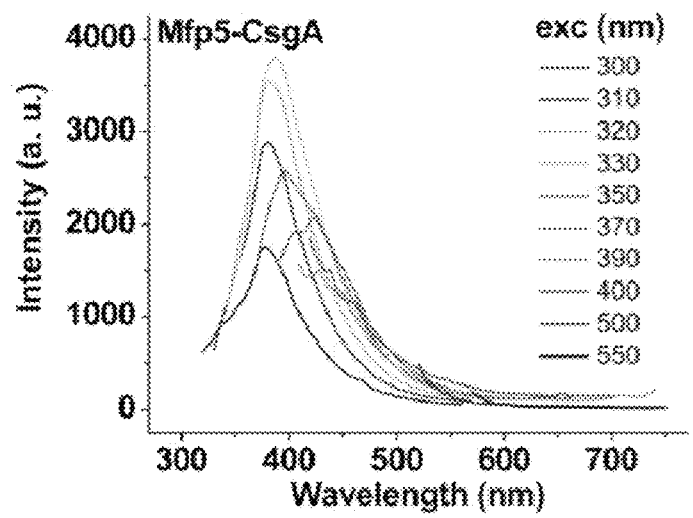

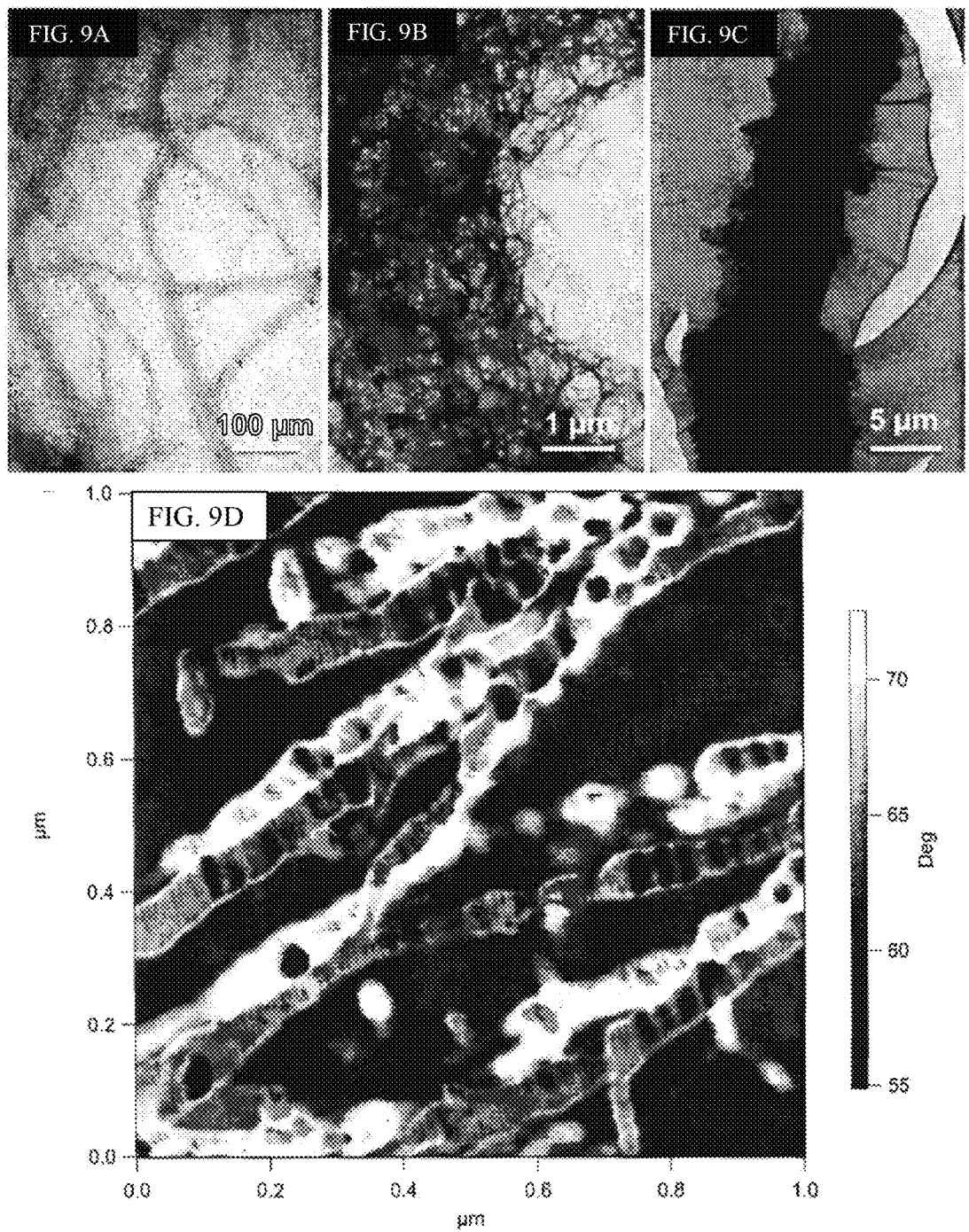

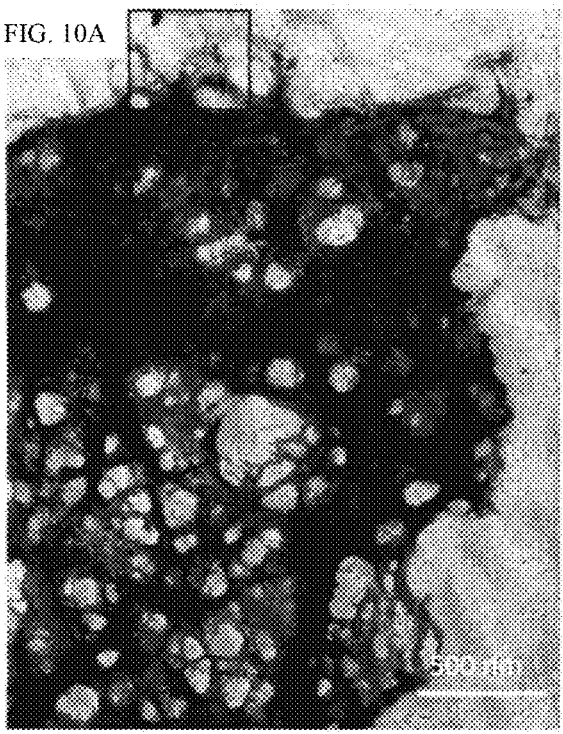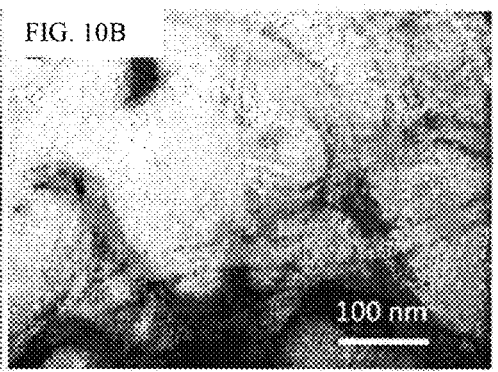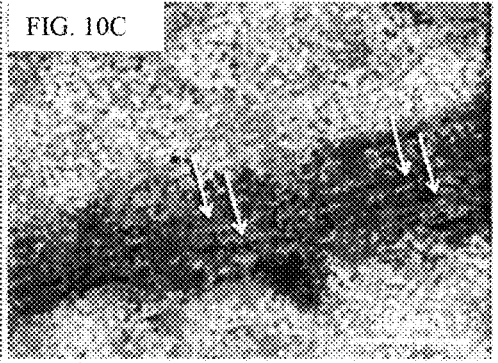

20 nm

HV = 80.0kV
Direct Mag: 180000x
AMT Camera System

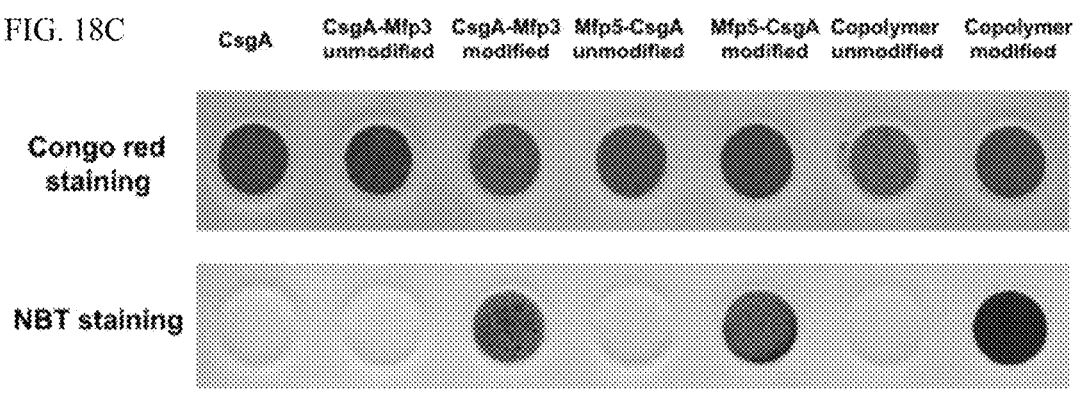

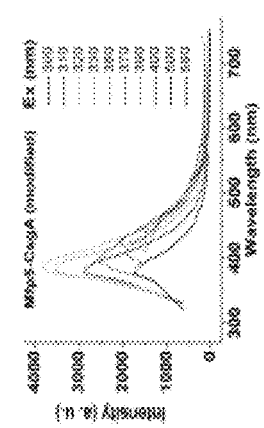
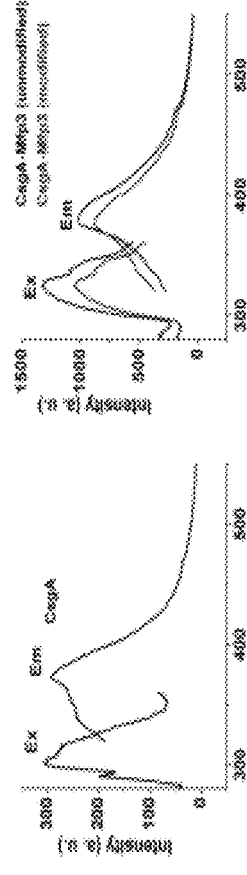
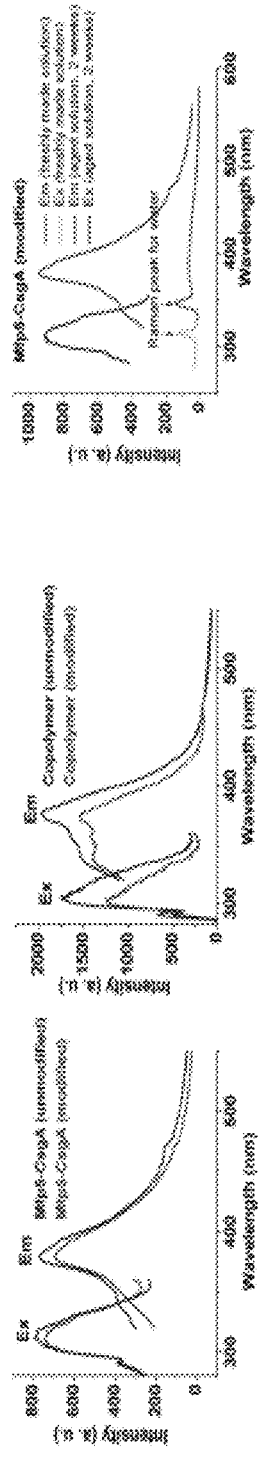
FIG. 19A
FIG. 19B
FIG. 19C
FIG. 19D

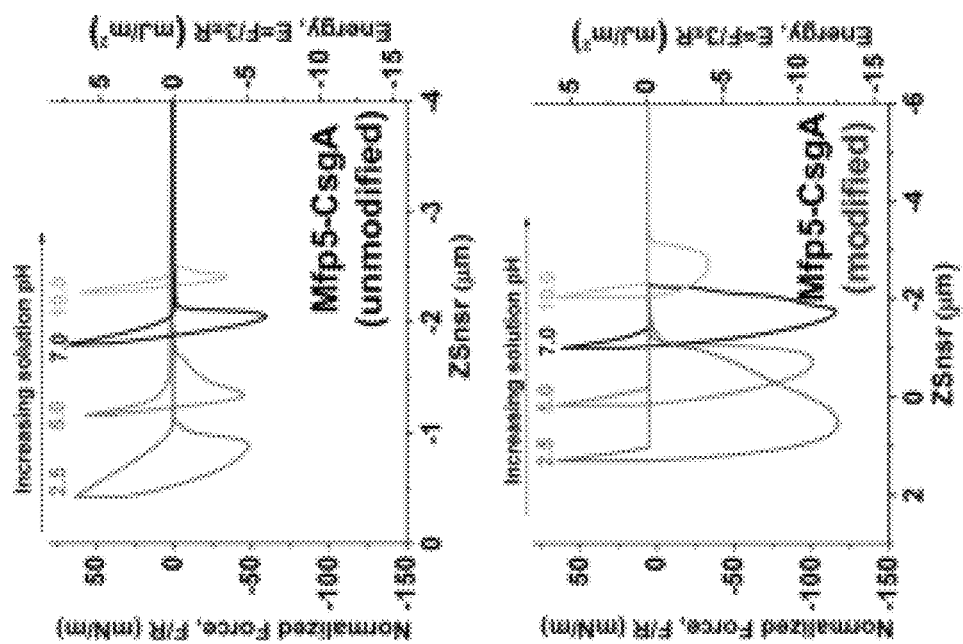
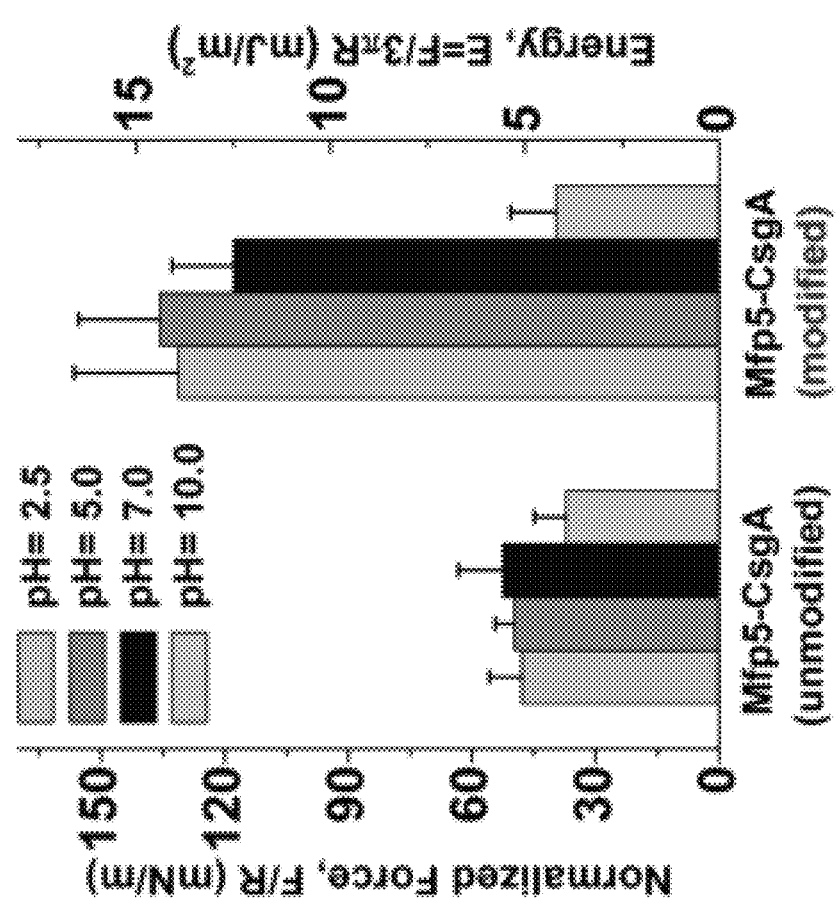
FIG. 20D

FIG. 24A
FIG. 24B
FIG. 24C
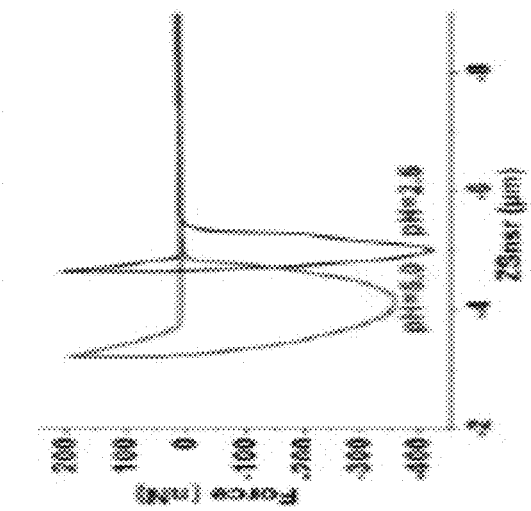
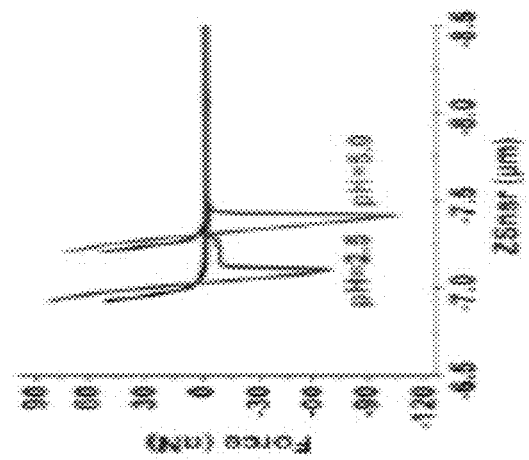

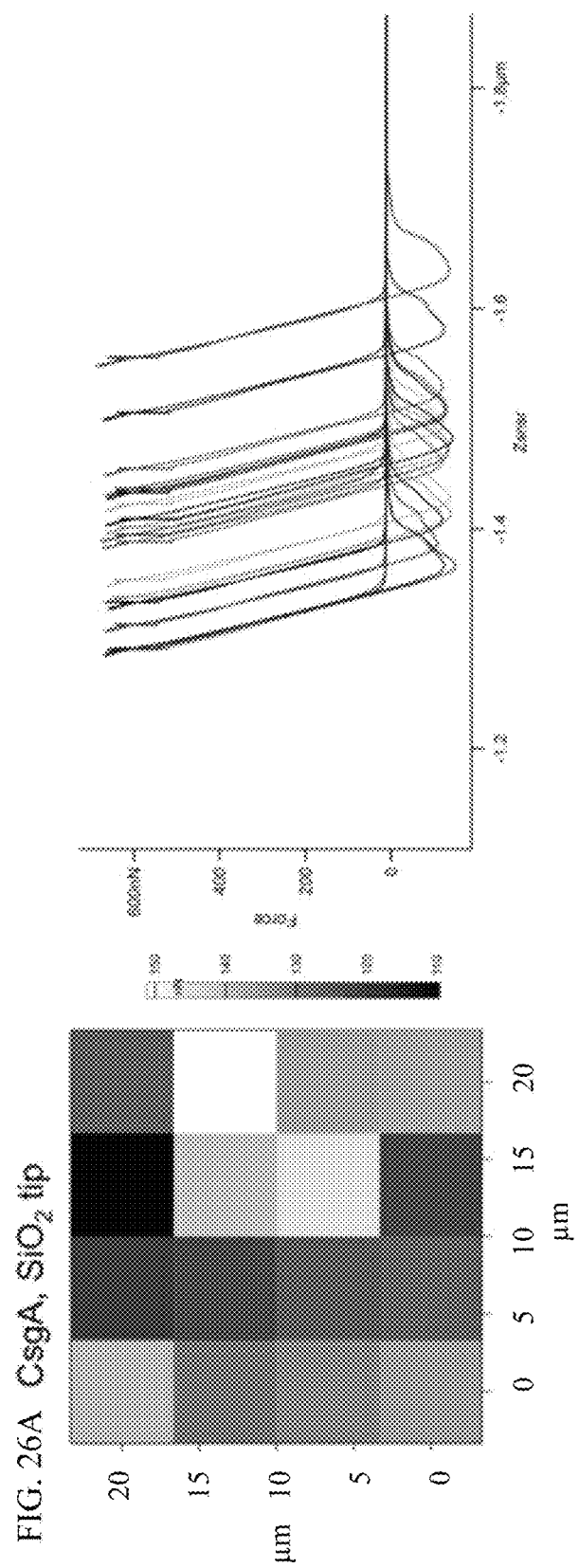
FIG. 26A CsgA, SiO₂ tip

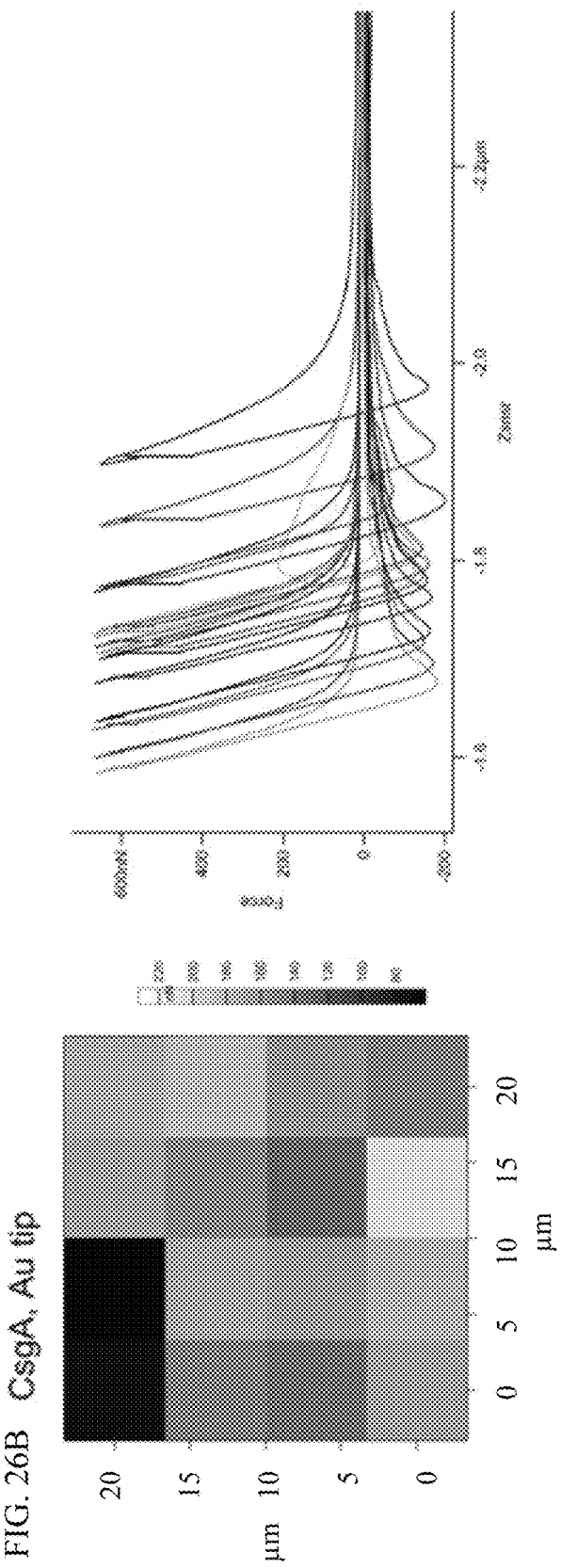
FIG. 26B CsgA, Au tip

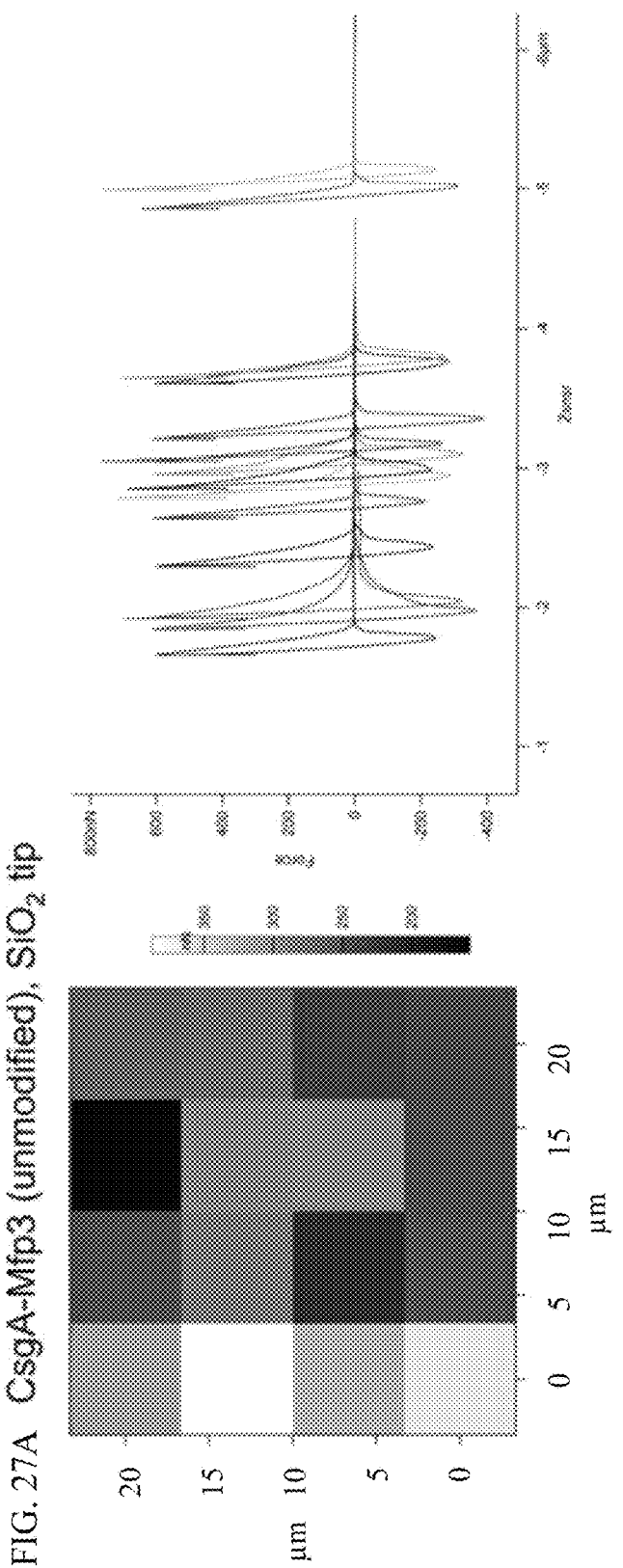
FIG. 27A CsgA-Mfp3 (unmodified), SiO₂ tip

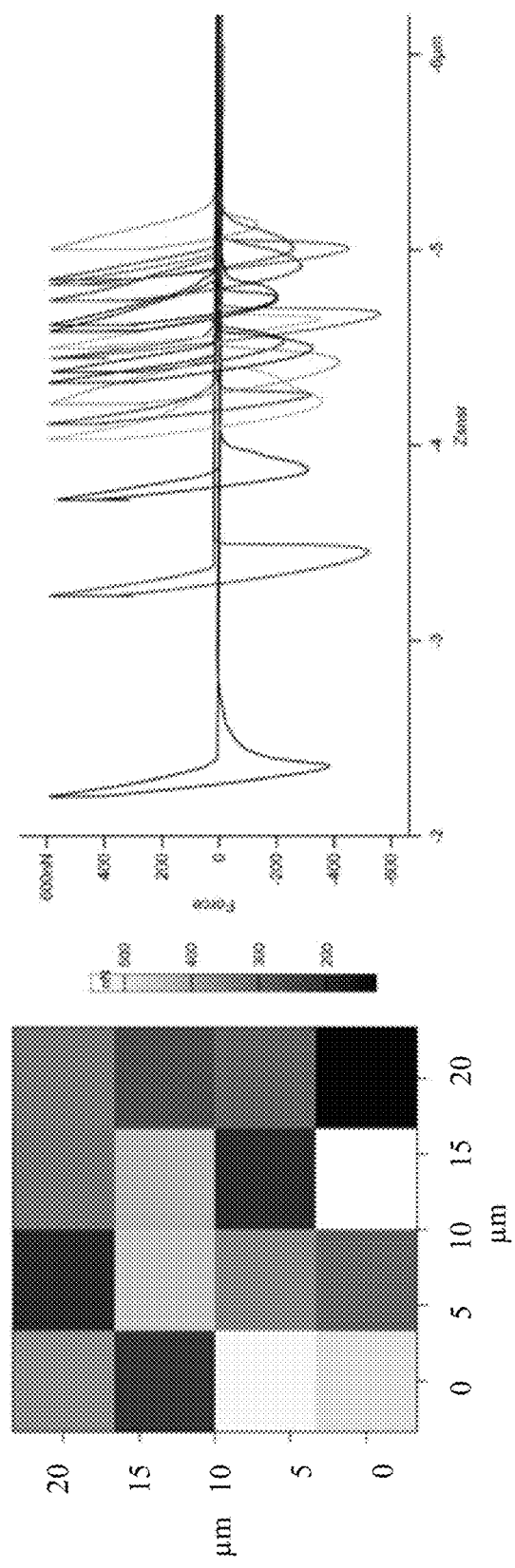
FIG. 27B CsgA-Mfp3 (unmodified), Au tip

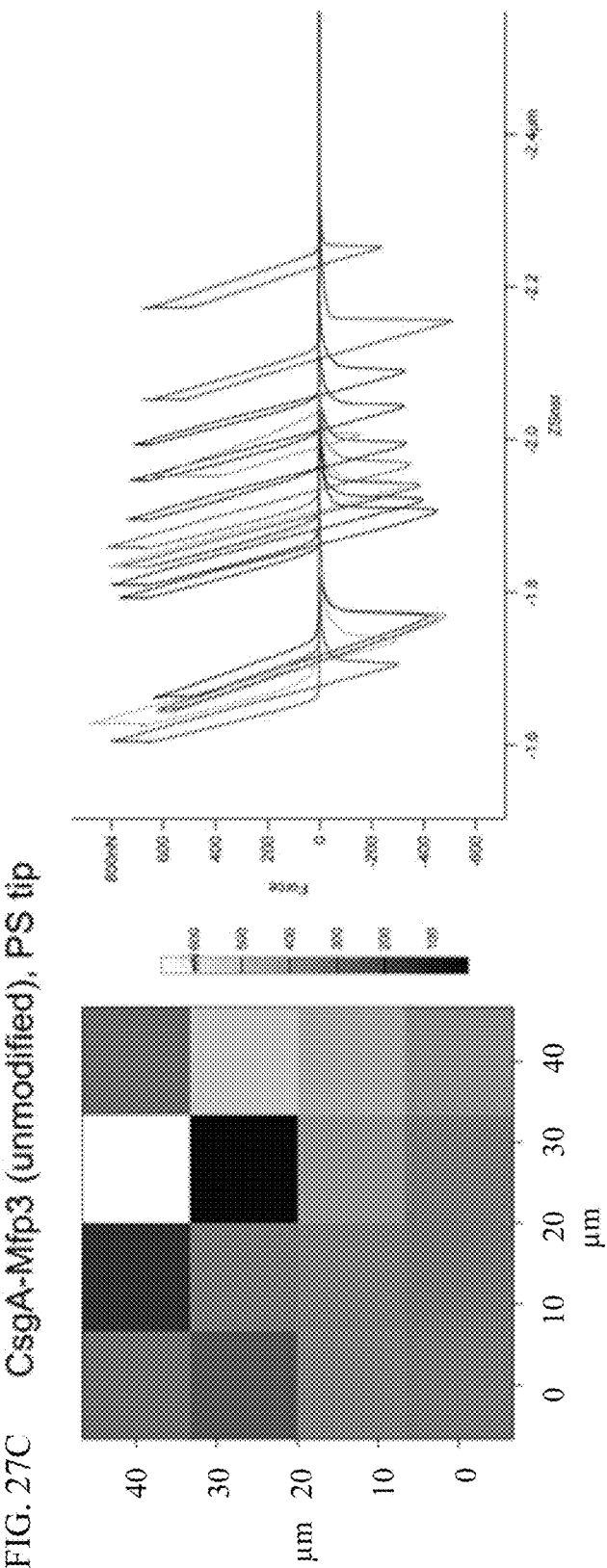
FIG. 27C CsgA-Mfp3 (unmodified), PS tip

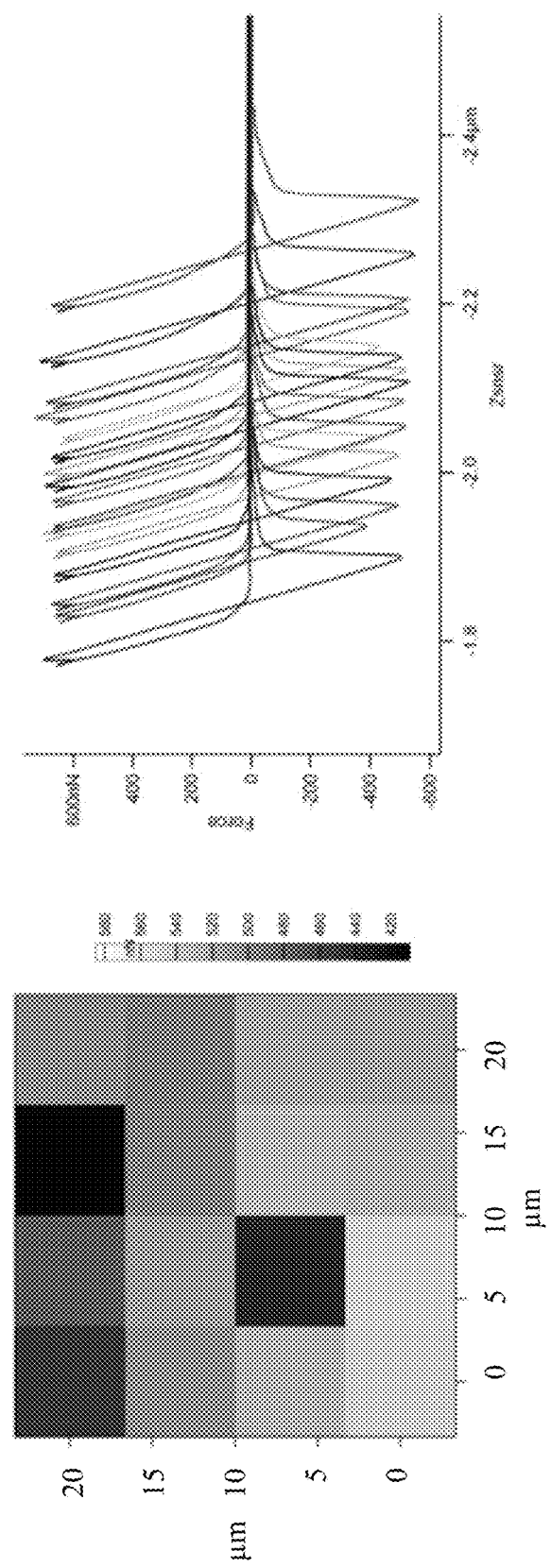
FIG. 28A  Mfp5-CsgA (unmodified), SiO₂ tip

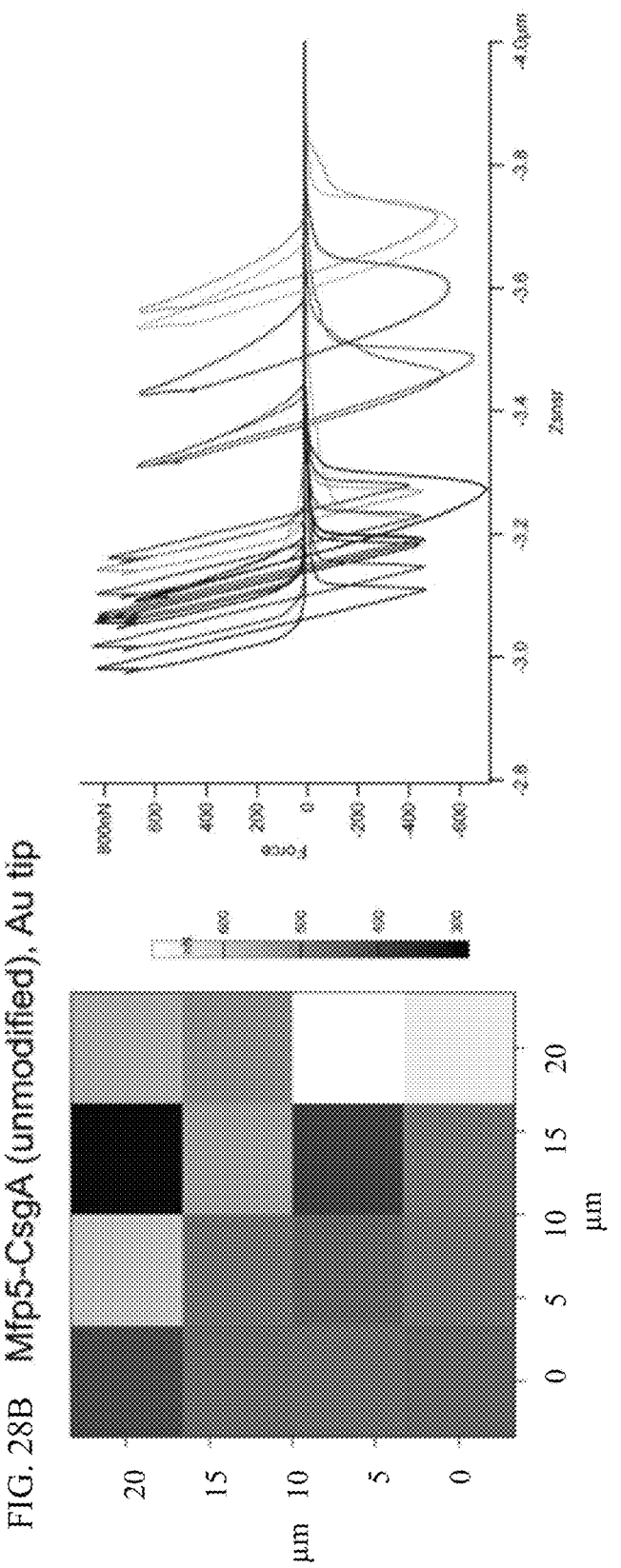
FIG. 28B  Mfp5-CsgA (unmodified), Au tip

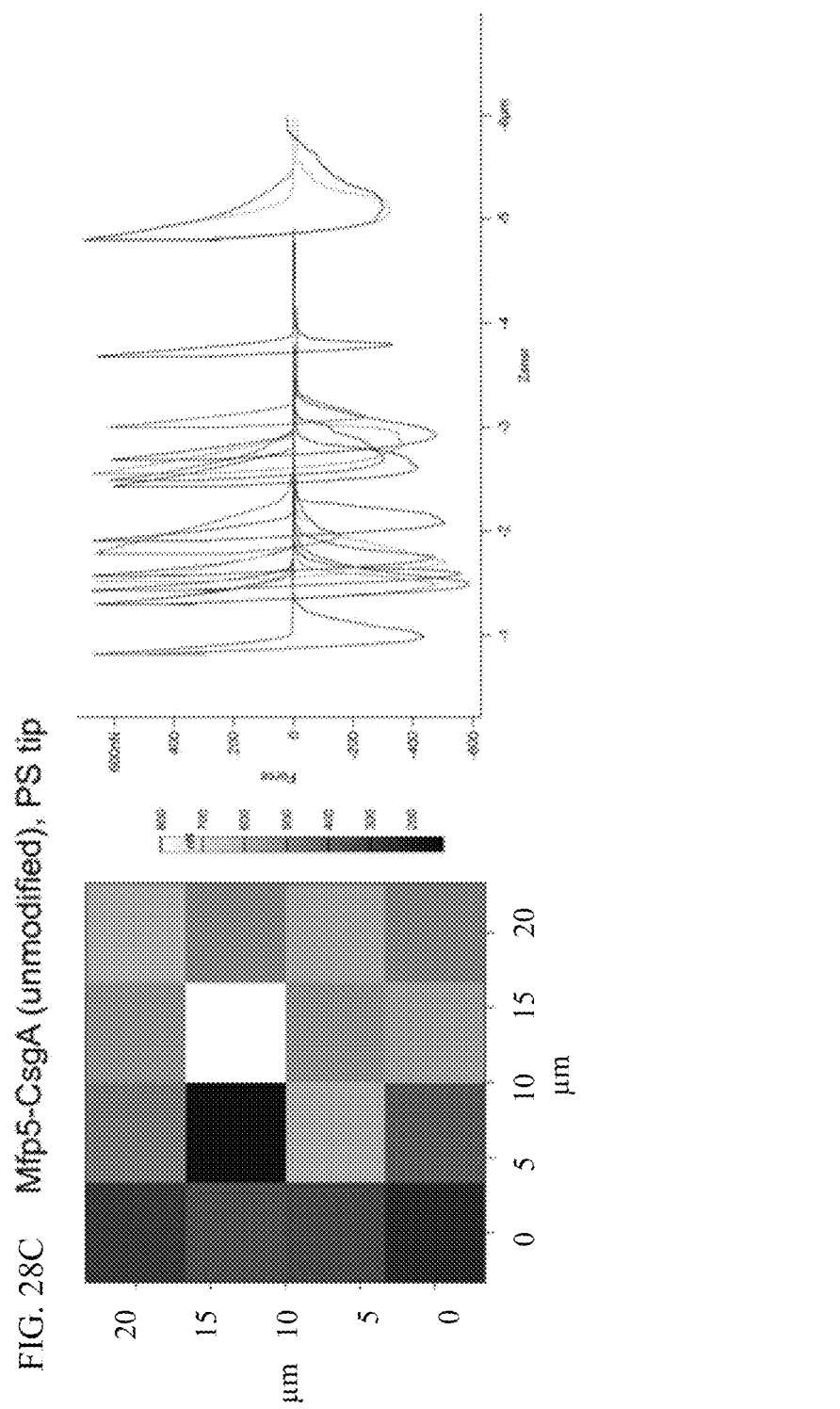
FIG. 28C  Mfp5-CsgA (unmodified), PS tip

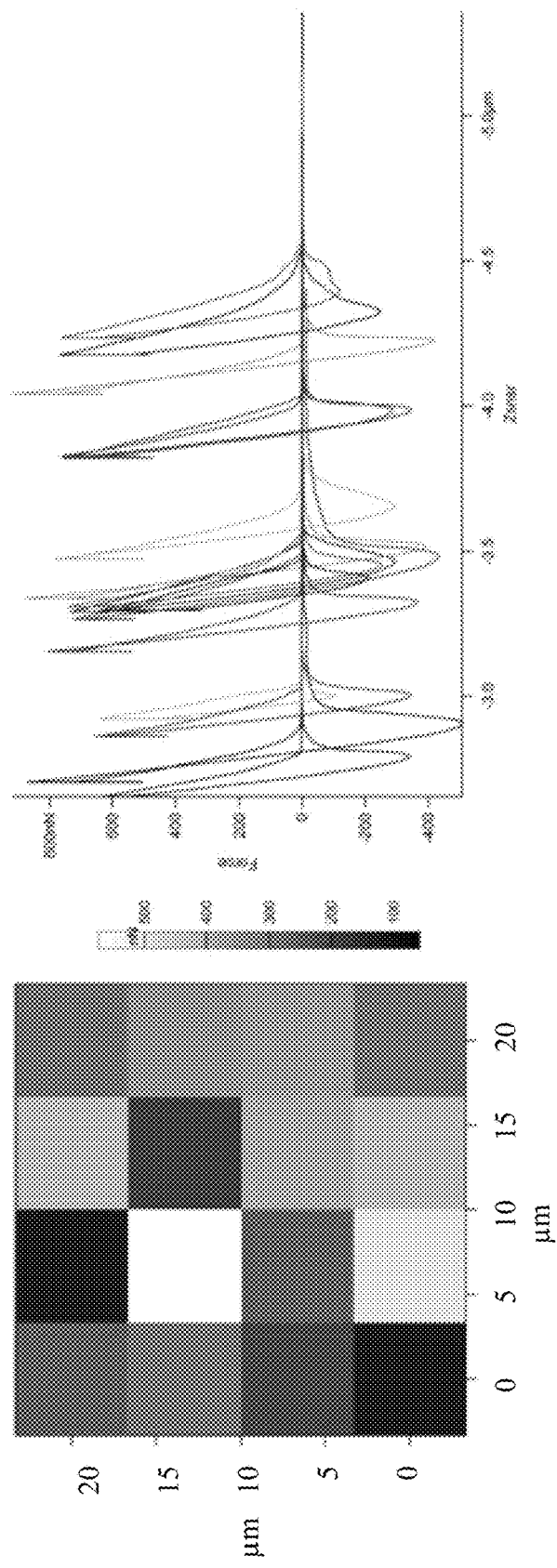
FIG. 29A Copolymer (unmodified), SiO$_2$ tip

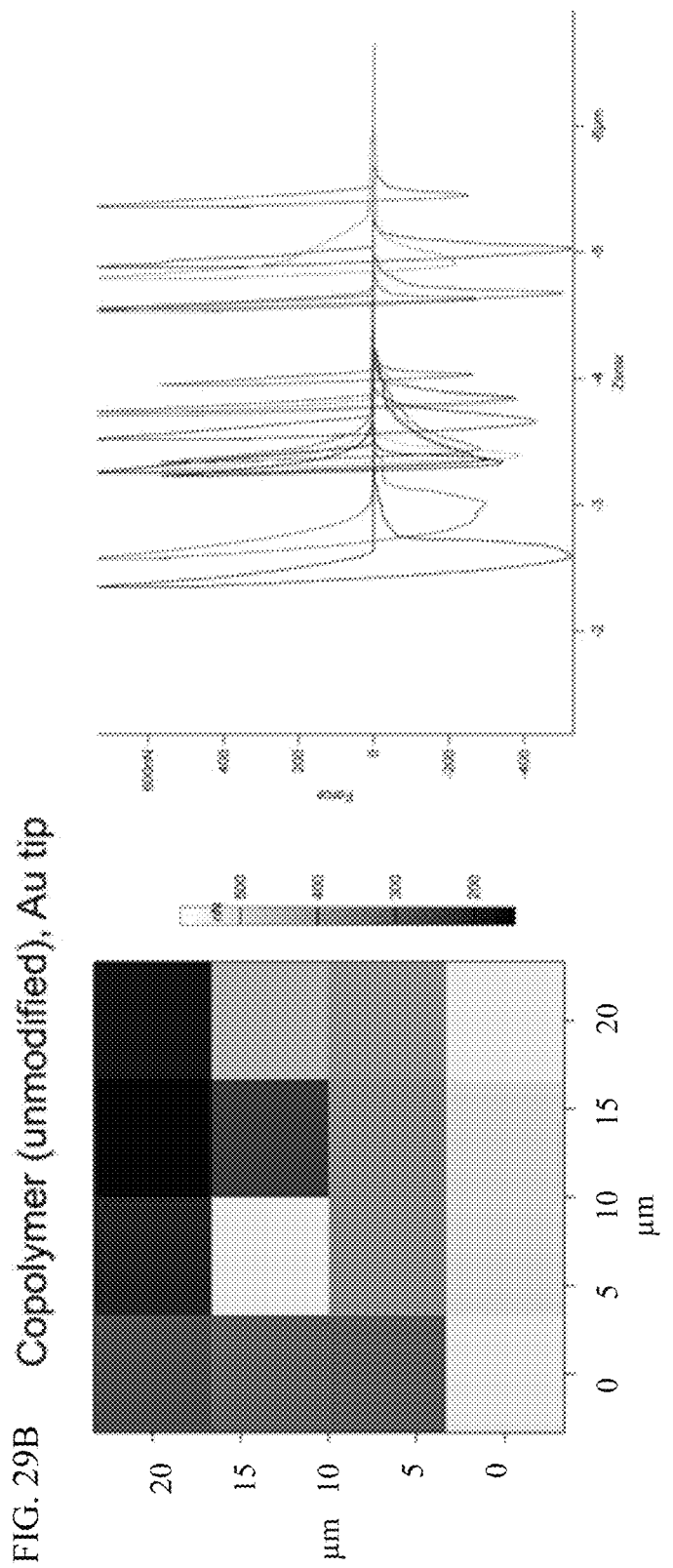
FIG. 29B Copolymer (unmodified), Au tip

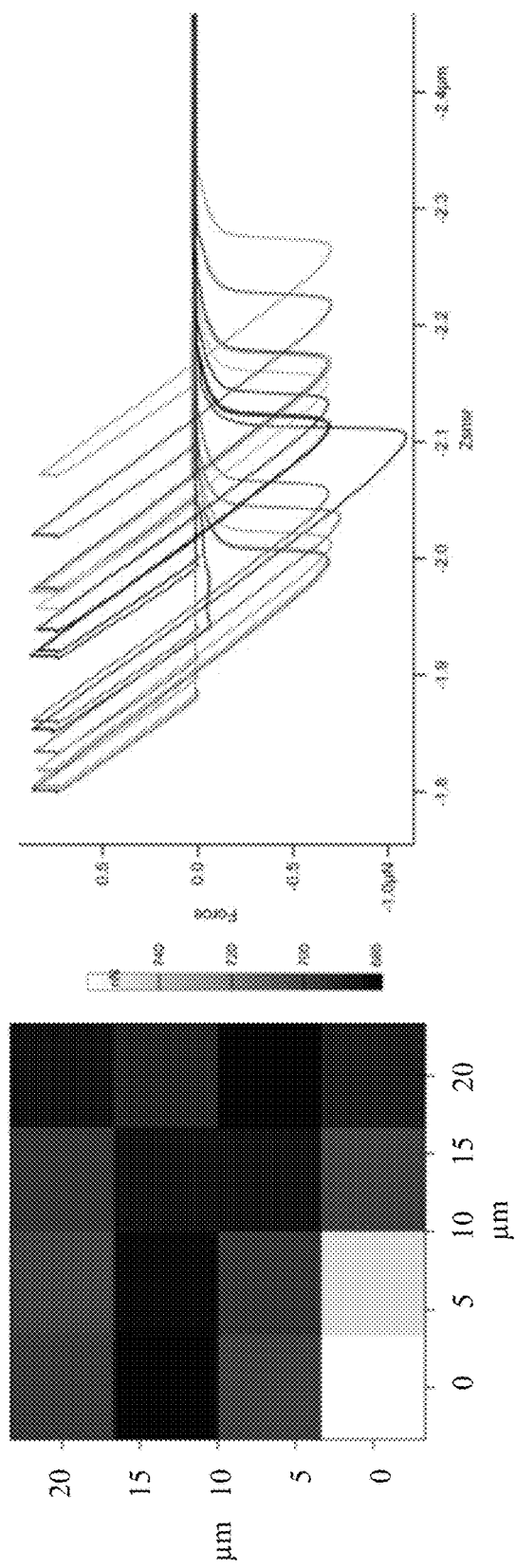
FIG. 30A CsgA-Mfp3 (modified), SiO$_2$ tip

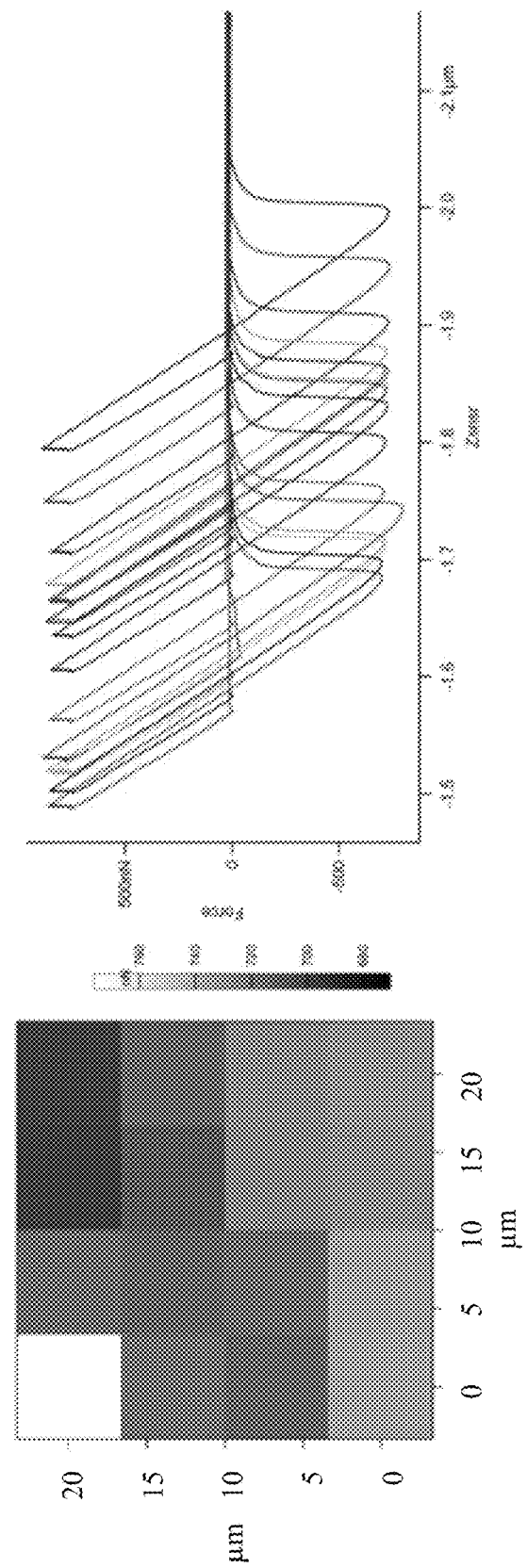
FIG. 30C CsgA-Mfp3 (modified), PS tip

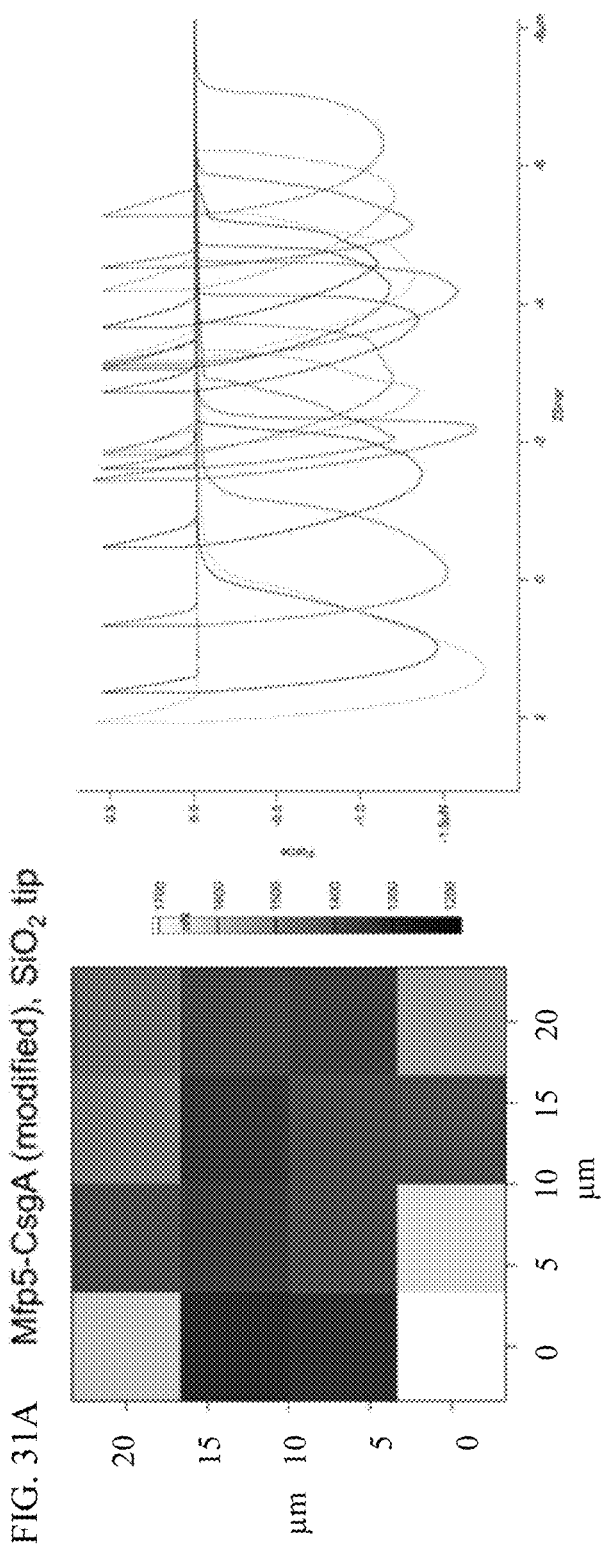
FIG. 31A  Mfp5-CsgA (modified), SiO$_2$ tip

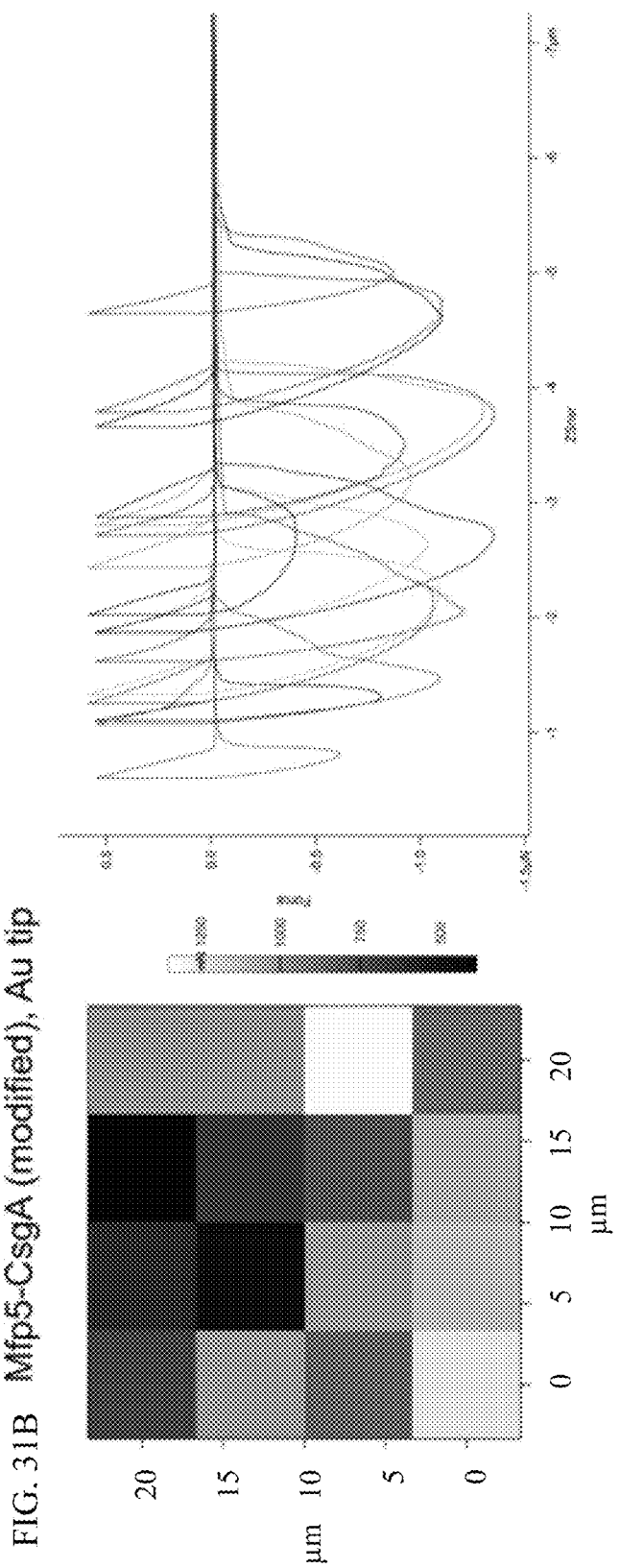
FIG. 31B  Mfp5-CsgA (modified), Au tip

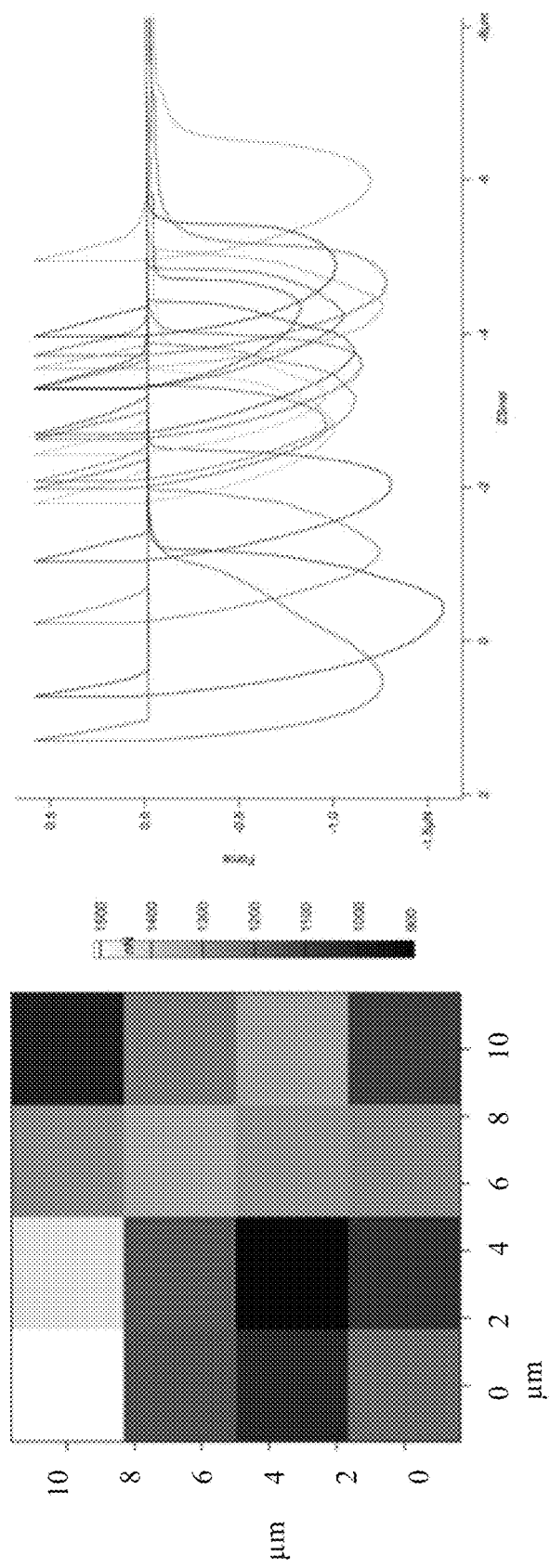
FIG. 31C Mfp5-CsgA (modified), PS tip

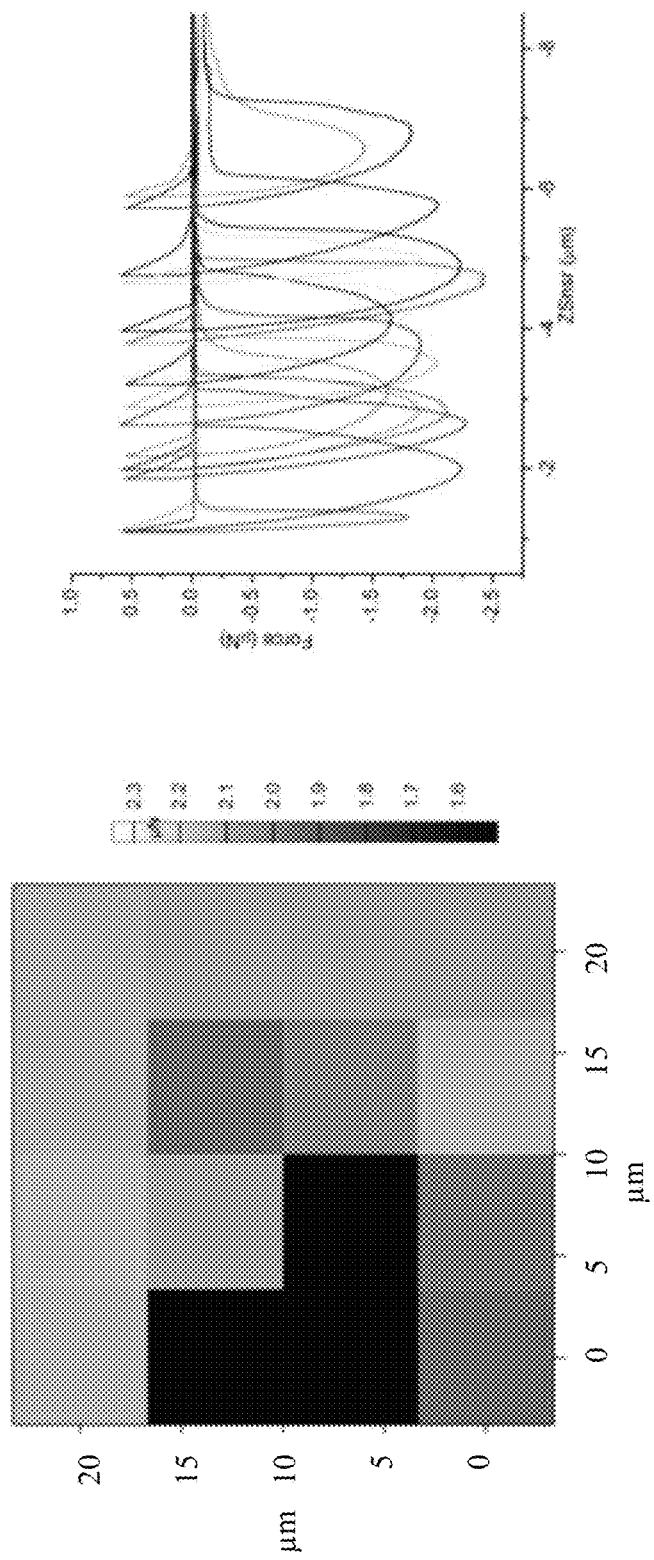
FIG. 32A Copolymer (modified), SiO₂ tip

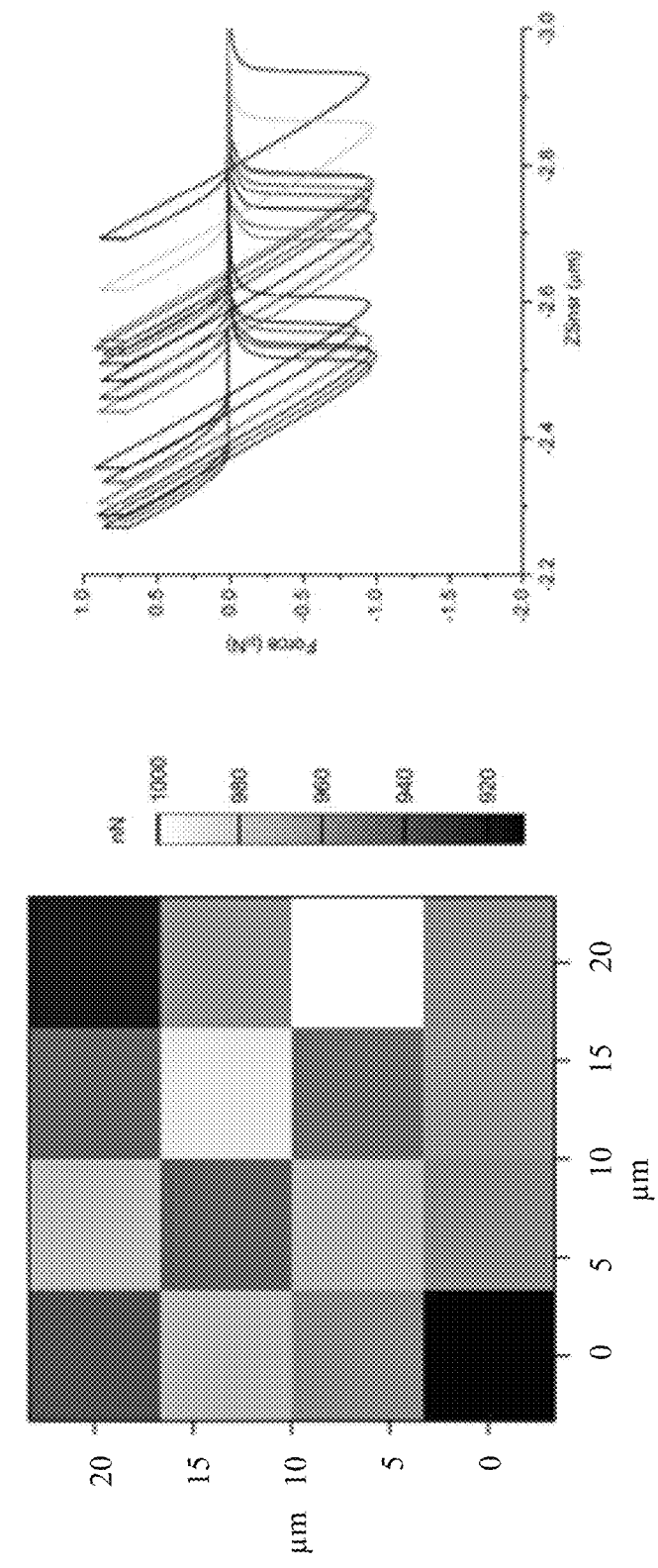
FIG. 32B Copolymer (modified), Au tip

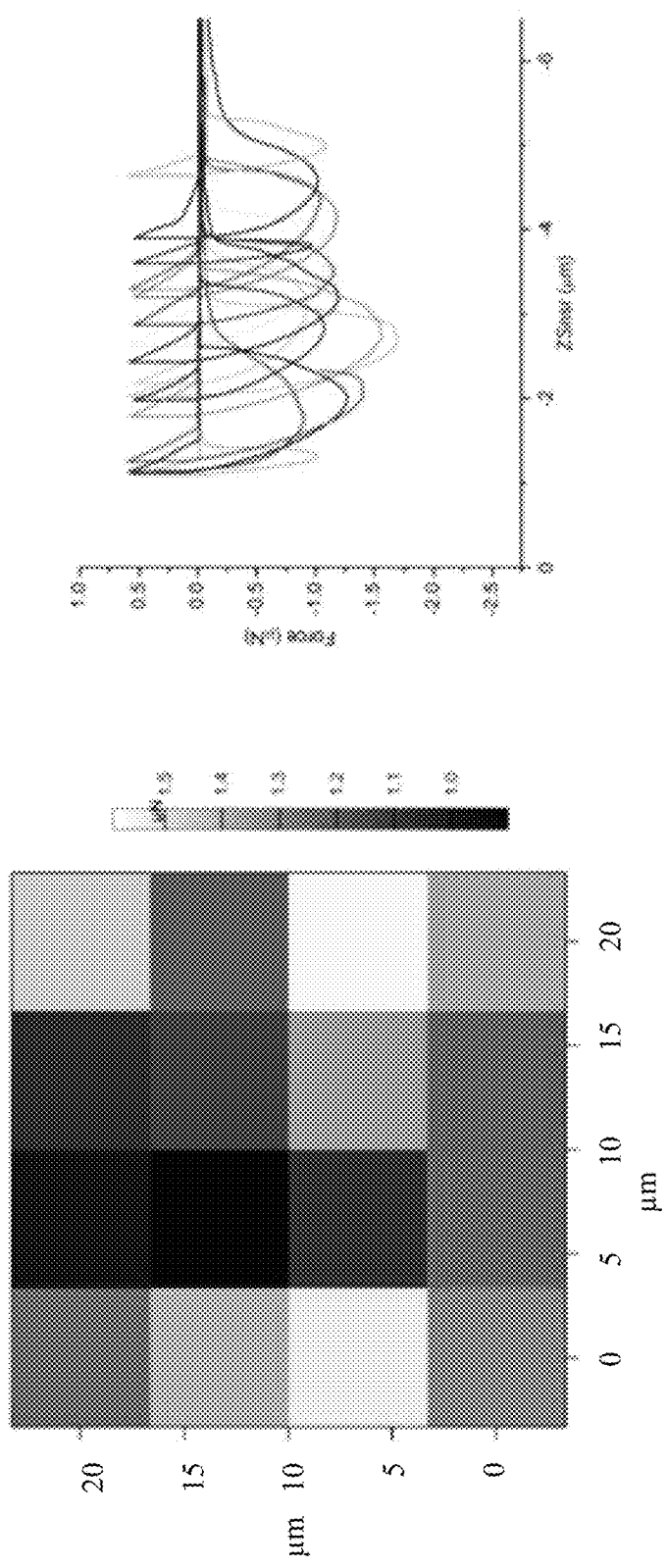
FIG. 32C Copolymer (modified), PS tip

SEQUENCE LISTING

<160> NUMBER OF SEQ ID NOS: 44

<210> SEQ ID NO 1
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 1

Ala Asp Tyr Tyr Gly Pro Lys Tyr Gly Pro Pro Arg Arg Tyr Gly Gly
1               5                  10                  15

Gly Asn Tyr Asn Arg Tyr Gly Arg Arg Tyr Gly Gly Tyr Lys Gly Trp
            20                  25                  30

Asn Asn Gly Trp Lys Arg Gly Arg Trp Gly Arg Lys Tyr Tyr
        35                  40                  45

<210> SEQ ID NO 2
<211> LENGTH: 76
<212> TYPE: PRT
<213> ORGANISM: Artificial Sequence
<220> FEATURE:
<223> OTHER INFORMATION: Synthetic Polypeptide

<400> SEQUENCE: 2

Ser Ser Glu Glu Tyr Lys Gly Gly Tyr Tyr Pro Gly Asn Thr Tyr His
1               5                  10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser
65                  70                  75

<210> SEQ ID NO 3
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 3

Ala Asp Tyr Tyr Gly Pro Asn Tyr Gly Pro Pro Arg Arg Tyr Gly Gly
1               5                  10                  15

Gly Asn Tyr Asn Arg Tyr Asn Arg Tyr Gly Arg Arg Tyr Gly Gly Tyr
            20                  25                  30

Lys Gly Trp Asn Asn Gly Trp Asn Arg Gly Arg Arg Gly Lys Tyr Trp
        35                  40                  45

<210> SEQ ID NO 4
<211> LENGTH: 74
<212> TYPE: PRT
<213> ORGANISM: Artificial Sequence
<220> FEATURE:
<223> OTHER INFORMATION: Synthetic Polypeptide

<400> SEQUENCE: 4

Ser Ser Glu Glu Tyr Lys Gly Gly Tyr Tyr Pro Gly Asn Ala Tyr His
1               5                  10                  15

Tyr His Ser Gly Gly Ser Tyr His Gly Ser Gly Tyr His Gly Gly Tyr

```
                    20                  25                  30
Lys Gly Lys Tyr Tyr Gly Lys Ala Lys Tyr Tyr Lys Tyr Lys
                35                  40                  45

Asn Ser Gly Lys Tyr Lys Tyr Leu Lys Lys Ala Arg Lys Tyr His Arg
            50                  55                  60

Lys Gly Tyr Lys Tyr Tyr Gly Gly Ser Ser
65                  70
```

<210> SEQ ID NO 5
<211> LENGTH: 151
<212> TYPE: PRT
<213> ORGANISM: Artificial Sequence
<220> FEATURE:
<223> OTHER INFORMATION: Synthetic Polypeptide

<400> SEQUENCE: 5

```
Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
                20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
        50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr
145                 150
```

<210> SEQ ID NO 6
<211> LENGTH: 151
<212> TYPE: PRT
<213> ORGANISM: Artificial Sequence
<220> FEATURE:
<223> OTHER INFORMATION: Synthetic Polypeptide

<400> SEQUENCE: 6

```
Met Lys Leu Leu Lys Val Ala Ala Phe Ala Ala Ile Val Val Ser Gly
1               5                   10                  15

Ser Ala Leu Ala Gly Val Val Pro Gln Trp Gly Gly Gly Gly Asn His
                20                  25                  30

Asn Gly Gly Gly Asn Ser Ser Gly Pro Asp Ser Thr Leu Ser Ile Tyr
            35                  40                  45

Gln Tyr Gly Ser Ala Asn Ala Ala Leu Ala Leu Gln Ser Asp Ala Arg
        50                  55                  60

Lys Ser Glu Thr Thr Ile Thr Gln Ser Gly Tyr Gly Asn Gly Ala Asp
65                  70                  75                  80

Val Gly Gln Gly Ala Asp Asn Ser Thr Ile Glu Leu Thr Gln Asn Gly
                85                  90                  95
```

```
Phe Arg Asn Asn Ala Thr Ile Asp Gln Trp Asn Ala Lys Asn Ser Asp
                100                 105                 110

Ile Thr Val Gly Gln Tyr Gly Gly Asn Ala Ala Leu Val Asn Gln
            115                 120                 125

Thr Ala Ser Asp Ser Ser Val Met Val Arg Gln Val Gly Phe Gly Asn
130                 135                 140

Asn Ala Thr Ala Asn Gln Tyr
145                 150
```

<210> SEQ ID NO 7
<211> LENGTH: 131
<212> TYPE: PRT
<213> ORGANISM: Artificial Sequence
<220> FEATURE:
<223> OTHER INFORMATION: Synthetic Polypeptide

<400> SEQUENCE: 7

```
Gly Val Val Pro Gln Tyr Gly Gly Gly Asn His Gly Gly Gly Gly
1               5                   10                  15

Asn Asn Ser Gly Pro Asn Ser Glu Leu Asn Ile Tyr Gln Tyr Gly Gly
                20                  25                  30

Gly Asn Ser Ala Leu Ala Leu Gln Thr Asp Ala Arg Asn Ser Asp Leu
            35                  40                  45

Thr Ile Thr Gln His Gly Gly Asn Gly Ala Asp Val Gly Gln Gly
    50                  55                  60

Ser Asp Asp Ser Ser Ile Asp Leu Thr Gln Arg Gly Phe Gly Asn Ser
65                  70                  75                  80

Ala Thr Leu Asp Gln Trp Asn Gly Lys Asn Ser Glu Met Thr Val Lys
                85                  90                  95

Gln Phe Gly Gly Gly Asn Gly Ala Ala Val Asp Gln Thr Ala Ser Asn
                100                 105                 110

Ser Ser Val Asn Val Thr Gln Val Gly Phe Gly Asn Asn Ala Thr Ala
            115                 120                 125

His Gln Tyr
    130
```

<210> SEQ ID NO 8
<211> LENGTH: 188
<212> TYPE: PRT
<213> ORGANISM: Artificial Sequence
<220> FEATURE:
<223> OTHER INFORMATION: Synthetic Polypeptide

<400> SEQUENCE: 8

```
Met Gly Val Val Pro Gln Tyr Gly Gly Gly Asn His Gly Gly Gly
1               5                   10                  15

Gly Asn Asn Ser Gly Pro Asn Ser Glu Leu Asn Ile Tyr Gln Tyr Gly
                20                  25                  30

Gly Gly Asn Ser Ala Leu Ala Leu Gln Thr Asp Ala Arg Asn Ser Asp
            35                  40                  45

Leu Thr Ile Thr Gln His Gly Gly Asn Gly Ala Asp Val Gly Gln
    50                  55                  60

Gly Ser Asp Asp Ser Ser Ile Asp Leu Thr Gln Arg Gly Phe Gly Asn
65                  70                  75                  80

Ser Ala Thr Leu Asp Gln Trp Asn Gly Lys Asn Ser Glu Met Thr Val
                85                  90                  95

Lys Gln Phe Gly Gly Gly Asn Gly Ala Ala Val Asp Gln Thr Ala Ser
                100                 105                 110
```

Asn Ser Ser Val Asn Val Thr Gln Val Gly Phe Gly Asn Asn Ala Thr
            115                 120                 125

Ala His Gln Tyr Gly Gly Gly Ser Gly Gly Gly Ser Ala Asp
    130                 135                 140

Tyr Tyr Gly Pro Lys Tyr Gly Pro Pro Arg Arg Tyr Gly Gly Asn
145                 150                 155                 160

Tyr Asn Arg Tyr Gly Arg Arg Tyr Gly Gly Tyr Lys Gly Trp Asn Asn
                165                 170                 175

Gly Trp Lys Arg Gly Arg Trp Gly Arg Lys Tyr Tyr
                180                 185

<210> SEQ ID NO 9
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 9

Met Ser Ser Glu Glu Tyr Lys Gly Gly Tyr Tyr Pro Gly Asn Thr Tyr
1               5                   10                  15

His Tyr His Ser Gly Gly Ser Tyr His Gly Ser Gly Tyr His Gly Gly
                20                  25                  30

Tyr Lys Gly Lys Tyr Tyr Gly Lys Ala Lys Lys Tyr Tyr Tyr Lys Tyr
            35                  40                  45

Lys Asn Ser Gly Lys Tyr Lys Tyr Leu Lys Lys Ala Arg Lys Tyr His
    50                  55                  60

Arg Lys Gly Tyr Lys Lys Tyr Tyr Gly Gly Ser Ser Gly Gly Gly
65                  70                  75                  80

Gly Ser Gly Gly Gly Ser Gly Val Val Pro Gln Tyr Gly Gly Gly
                85                  90                  95

Gly Asn His Gly Gly Gly Asn Asn Ser Gly Pro Asn Ser Glu Leu
            100                 105                 110

Asn Ile Tyr Gln Tyr Gly Gly Gly Asn Ser Ala Leu Ala Leu Gln Thr
            115                 120                 125

Asp Ala Arg Asn Ser Asp Leu Thr Ile Thr Gln His Gly Gly Gly Asn
    130                 135                 140

Gly Ala Asp Val Gly Gln Gly Ser Asp Ser Ser Ile Asp Leu Thr
145                 150                 155                 160

Gln Arg Gly Phe Gly Asn Ser Ala Thr Leu Asp Gln Trp Asn Gly Lys
                165                 170                 175

Asn Ser Glu Met Thr Val Lys Gln Phe Gly Gly Gly Asn Gly Ala Ala
            180                 185                 190

Val Asp Gln Thr Ala Ser Asn Ser Ser Val Asn Val Thr Gln Val Gly
            195                 200                 205

Phe Gly Asn Asn Ala Thr Ala His Gln Tyr
    210                 215

<210> SEQ ID NO 10
<211> LENGTH: 602
<212> TYPE: DNA
<213> ORGANISM: Artificial Sequence
<220> FEATURE:
<223> OTHER INFORMATION: Synthetic Polynucleotide

<400> SEQUENCE: 10
attcaggtgg tagttatcac ggatccggct atcatggagg atataaggga aagtattacg      60

```
gaaaggcaaa gaaatactat tataaatata aaaacagcgg aaaatacaag tatctgaaga    120
aagctagaaa ataccataga aagggttaca agaagtatta tggaggtggt agcagtggcg    180
gtggcggtag cggtggcggt ggcagtggtg ttgttcctca gtacggcggc ggcggtaacc    240
acggtggtgg cggtaataat agcggcccaa attctgagct gaacatttac cagtacggtg    300
gcggtaactc tgcacttgct ctgcaaactg atgcccgtaa ctctgacttg actattaccc    360
agcatggcgg cggtaatggt gcagatgttg gtcagggctc agatgacagc tcaatcgatc    420
tgacccaacg tggcttcggt aacagcgcta ctcttgatca gtggaacggc aaaaattctg    480 aaaatgacggt taaacagttc ggtggtggca acggtgctgc agttgaccag actgcatcta    540
actcctccgt caacgtgact caggttggct ttggtaacaa cgcgaccgct catcagtact    600
aa                                                                    602
```

<210> SEQ ID NO 11
<211> LENGTH: 567
<212> TYPE: DNA
<213> ORGANISM: Artificial Sequence
<220> FEATURE:
<223> OTHER INFORMATION: Synthetic Polynucleotide

<400> SEQUENCE: 11

```
atgggtgttg ttcctcagta cggcggcggc ggtaaccacg gtggtggcgg taataatagc     60
ggcccaaatt ctgagctgaa catttaccag tacggtggcg gtaactctgc acttgctctg    120
caaactgatg cccgtaactc tgacttgact attacccagc atggcggcgg taatggtgca    180
gatgttggtc agggctcaga tgacagctca atcgatctga cccaacgtgg cttcggtaac    240
agcgctactc ttgatcagtg gaacggcaaa aattctgaaa tgacggttaa acagttcggt    300
ggtggcaacg gtgctgcagt tgaccagact gcatctaact cctccgtcaa cgtgactcag    360
gttggctttg gtaacaacgc gaccgctcat cagtacggcg gtggcggtag cggtggcggt    420
ggcagtgctg attattatgg tccaaagtat ggtcctccaa gacgctacgg tggtggcaac    480
tacaatagat atggcagacg ttatggcggg tataaaggct ggaacaatgg ttggaaaaga    540
ggtcgatggg gacgaaagta ttattaa                                         567
```

<210> SEQ ID NO 12
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 12

Met Lys Leu Leu Lys Val Ala Ala Ile Ala Ala Ile Val Phe Ser Gly
1               5                   10                  15

Ser Ala Leu Ala
            20

<210> SEQ ID NO 13
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 13

Gly Val Val Pro Gln Tyr Gly Gly Gly Gly Asn His Gly Gly Gly Gly
1               5                   10                  15

Asn Asn Ser Gly Pro Asn
            20

<210> SEQ ID NO 14
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 14

Ser Glu Leu Asn Ile Tyr Gln Tyr Gly Gly Gly Asn Ser Ala Leu Ala
1               5                   10                  15

Leu Gln Thr Asp Ala Arg Asn
            20

<210> SEQ ID NO 15
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 15

Ser Asp Leu Thr Ile Thr Gln His Gly Gly Gly Asn Gly Ala Asp Val
1               5                   10                  15

Gly Gln Gly Ser Asp Asp
            20

<210> SEQ ID NO 16
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 16

Ser Ser Ile Asp Leu Thr Gln Arg Gly Phe Gly Asn Ser Ala Thr Leu
1               5                   10                  15

Asp Gln Trp Asn Gly Lys Asn
            20

<210> SEQ ID NO 17
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 17

Ser Glu Met Thr Val Lys Gln Phe Gly Gly Gly Asn Gly Ala Ala Val
1               5                   10                  15

Asp Gln Thr Ala Ser Asn
            20

<210> SEQ ID NO 18
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 18

Ser Ser Val Asn Val Thr Gln Val Gly Phe Gly Asn Asn Ala Thr Ala

<210> SEQ ID NO 19
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 19

Met Lys Leu Leu Lys Val Ala Ala Phe Ala Ala Ile Val Val Ser Gly
1               5                   10                  15

Ser Ala Leu Ala
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 20

Gly Val Val Pro Gln Trp Gly Gly Gly Gly Asn His Asn Gly Gly Gly
1               5                   10                  15

Asn Ser Ser Gly Pro Asp
            20

<210> SEQ ID NO 21
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 21

Ser Thr Leu Ser Ile Tyr Gln Tyr Gly Ser Ala Asn Ala Ala Leu Ala
1               5                   10                  15

Leu Gln Ser Asp Ala Arg Lys
            20

<210> SEQ ID NO 22
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 22

Ser Glu Thr Thr Ile Thr Gln Ser Gly Tyr Gly Asn Gly Ala Asp Val
1               5                   10                  15

Gly Gln Gly Ala Asp Asn
            20

<210> SEQ ID NO 23
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 23

Ser Thr Ile Glu Leu Thr Gln Asn Gly Phe Arg Asn Asn Ala Thr Ile

Asp Gln Trp Asn Ala Lys Asn
            20

<210> SEQ ID NO 24
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 24

Ser Asp Ile Thr Val Gly Gln Tyr Gly Gly Asn Asn Ala Ala Leu Val
1               5                   10                  15

Asn Gln Thr Ala Ser Asp
            20

<210> SEQ ID NO 25
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 25

Ser Ser Val Met Val Arg Gln Val Gly Phe Gly Asn Asn Ala Thr Ala
1               5                   10                  15

Asn Gln Tyr

<210> SEQ ID NO 26
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 26

Gly Gly Gly Gly Ser Gly Gly Gly Gly Ser
1               5                   10

<210> SEQ ID NO 27
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is hydroxyproline

<400> SEQUENCE: 27

Gly Phe Xaa Gly Glu Arg
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 28

Pro His Ser Arg Asn
1               5

```
<210> SEQ ID NO 29
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 29

Arg Glu Asp Val
1

<210> SEQ ID NO 30
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 30

Ile Lys Val Ala Val
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 31

Tyr Ile Gly Ser Arg
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 32

Pro Asp Ser Gly Arg
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 33

Val Pro Gly Xaa Gly
1               5

<210> SEQ ID NO 34
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 34
```
cagtacggtg gcggtaactc tgcacttgct ctgcaaactg                                      40

<210> SEQ ID NO 35
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 35
atcaccatca ccatcaccat                                                           20

<210> SEQ ID NO 36
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 36

Ser Gly Asp Leu Glu Asn Glu Val Ala Gln Leu Glu Asn Glu Val Arg
1               5                   10                  15

Ser Leu Glu Asp Glu Ala Ala Glu Leu Glu Gln Lys Val Ser Arg Leu
            20                  25                  30

Lys Asn Glu Ile Glu Asp Leu Lys Ala Glu
        35                  40

<210> SEQ ID NO 37
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 37
tttaacttta agaaggagat ataccatggg tgttgttcct cag                                 43

<210> SEQ ID NO 38
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 38
actgccaccg ccaccgctac cgccaccgcc gtactgatga gcggtcg                             47

<210> SEQ ID NO 39
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 39
ggcggtggcg gtagcggtgg cggtggcagt gctgattatt atggtccaaa gta                      53

<210> SEQ ID NO 40
<211> LENGTH: 72
<212> TYPE: DNA
<213> ORGANISM: Artificial Sequence
<220> FEATURE:
<223> OTHER INFORMATION: Synthetic Polynucleotide

<400> SEQUENCE: 40

```
tttcgggctt tgttagcagc cggatccta atggtgatgg tgatggtgat gataatactt        60
tcgtccccat cg                                                           72

<210> SEQ ID NO 41
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 41
tttaacttta agaaggagat ataccatgag ttctgaagaa tacaaaggtg                  50

<210> SEQ ID NO 42
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 42
ggaacaacac cactgccacc gccaccgcta ccgccaccgc cactgctacc acctcca          57

<210> SEQ ID NO 43
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 43
ggtggcggtg gcagtggtgt tgttcctcag tacg                                   34

<210> SEQ ID NO 44
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 44
gcttcctttc gggcttt                                                      17
```

SELF-ASSEMBLING UNDERWATER ADHESIVES

RELATED APPLICATIONS

The present application claims priority under 35 U.S.C. § 119(e) to U.S. provisional patent applications, U.S. Ser. No. 61/903,824, filed Nov. 13, 2013, and U.S. Ser. No. 62/051,104, filed Sep. 16, 2014, each of which is incorporated herein by reference.

FEDERALLY SPONSORED RESEARCH

This invention was made with Government support under Grant No. DMR-0819762 awarded by the National Science Foundation, under Grant No. W911NF-11-1-0281 awarded by the Army Research Office, and under Grant No. N00014-11-1-0687 awarded by the Office of Naval Research. The Government has certain rights in the invention.

BACKGROUND OF INVENTION

Several living organisms exhibit remarkable moisture-resistant adhesion to a variety of substrata.[1,2] For example, mussels attach to a variety of substrates under wet and turbulent environments using unstructured mussel holdfast proteins,[2] and marine invertebrates and microorganisms achieve interfacial adhesion and self-protection using functional amyloid proteins.[3,4] Natural underwater adhesives, particularly the mussel holdfasts, have inspired the development of catechol-containing or catechol-analogue-containing peptides,[6] polymers,[7] and recombinant mussel-mimic adhesive proteins,[9] with multiple applications ranging from surface coatings to medical adhesives.[2,7,10] To date, however, biomimetic adhesives have not yet achieved or exceeded the strong wet bonding strengths, robustness, or functionalities of their natural counterparts.

SUMMARY OF INVENTION

Provided herein are biomimetic adhesives that in some cases have been found to outperform naturally occurring adhesives, for example, in bonding materials in a wet or aqueous environment and providing multifunctional capabilities. A synthetic biology-enabled modular design was used to recombine genes that encode two natural adhesive elements: mussel foot proteins (Mfp) from mussels[2,11] and functional amyloid adhesive from *E. coli* (e.g., CsgA, subunit for Curli amyloid)[4]. The recombinant fusion proteins (e.g., CsgA-Mfp3 and Mfp5-CsgA) hierarchically self-assemble into fiber bundles or networks composed of fibril nanostructures with underwater adhesive properties that typically outperform the individual adhesiveness of CsgA or recombinant Mfp3/Mfp5 alone. Unexpectedly, these adhesives also exhibit intrinsic fluorescence. Molecular dynamics simulation reveal that both CsgA-Mfp3 and Mfp5-CsgA proteins exist as stable cross β-strand structures in aqueous solution, with disordered Mfp domains external to the central amyloid cores formed by CsgA domains. The two individual domains contribute to both the strong wet adhesion and the intrinsic fluorescence. Furthermore, the co-assembly (or copolymerization) of two different fusion proteins (e.g., CsgA-Mfp3, Mfp5-CsgA) led to fusion protein copolymer (or oligomeric) fibers (e.g., fibers of (CsgA-Mfp3)-co-(Mfp5-CsgA) copolymer) with strong underwater adhesive properties, outperforming known bio-derived and bio-inspired protein-based underwater adhesives reported thus far. Because these new adhesive biomaterials transition from an aqueous and injectable solution to a sticky fibril-based plaque or network, they have utility in both medical and technical fields, for example, as bioadhesives for surgical applications and as underwater adhesives for marine or plumbing applications. Additionally, other novel fusion proteins are provided including adhesive fusion proteins comprising thermal-reversible domains and/or domains that promote wound healing. The adhesive fusion proteins described herein comprising thermal-reversible domains are also useful for forming fusion protein copolymers. As used herein, the term monomer or the phrase monomer protein are used interchangeably with the phrase fusion proteins.

Accordingly, aspects of the present invention relate to novel fusion proteins comprising an adhesive protein and an amyloid protein. For example, the fusion protein may comprise an adhesive protein derived from a marine organism, or a fragment thereof, and an amyloid protein (e.g., a bacterial amyloid protein), or a fragment thereof. In some embodiments, the adhesive protein is derived from the sandcastle worm *Phragmatopoma californica* (e.g., Pc1, Pc2, Pc3A, Pc3B, Pc4, Pc5); caddisflies of the order Trichoptera (e.g., *Brachycentrus echo*, which produced underwater adhesive silks comprised of h-fibroin proteins); midge larva of the genus *Chironomus* (e.g., sp-Ia, sp-Ib, sp-Ic, sp-Id); sea cucumber (e.g., *Holothuria forskåli*) Cuvierian tubule adhesive protein; or barnacles (e.g., adhesive proteins cp-19k and cp-20k produced by *Megabalanus rosa*). In some embodiments, the adhesive protein is a mussel foot protein (Mfp), or a fragment thereof, derived from *Mytilus galloprovincialis* or *Mytilus edulis*. In some embodiments, the amyloid protein is a yeast or bacterial (e.g., derived from *Escherichia coli* (CsgA) or *Salmonella enteritidis* (AgfA)) amyloid protein. Typically, such fusion proteins are capable of forming amyloid structures. In some embodiments, the Mfp is Mfp3 (e.g., SEQ ID NO:1 or SEQ ID NO:3) or Mfp5 (e.g., SEQ ID NO:2 or SEQ ID NO:4). In some aspects, the Mfp3 or Mfp5 is at least 85%, at least 90%, at least 95%, or at least 98% identical to the wild-type amino acid sequence for Mfp3 or Mfp5, respectively. In some embodiments, the bacterial amyloid protein is CsgA (SEQ ID NO:5). In some aspects, the bacterial amyloid protein is at least 85%, at least 90%, at least 95%, or at least 98% identical to the wild-type amino acid sequence of CsgA. In some embodiments, Mfp3 or Mfp5 is fused to the C-terminus of CsgA, Mfp3 or Mfp5 is fused to the N-terminus of CsgA, or Mfp3 or Mfp5 is fused within CsgA. In some aspects, the engineered fusion of Mfp3 or Mfp5 with CsgA does not disrupt self-assembly of fibrils comprising the fusion protein. In some aspects, a linker is used to join Mfp3 or Mfp5 with CsgA, for example, a peptidic or non-peptidic linker. In some aspects, the non-peptidic linker is selected from a carbohydrate, a polyester, or a dendrimer. In some aspects, the non-peptidic linker is a PEG linker, a polyester amide, or a peptoid. With peptidic linkers, the linker comprises at least 1, at least 2, at least 3, at least 4, at least 5, at least 6, at least 7, at least 8, a least 9, at least 10, at least 11, at least 12, at least 13, at least 14, at least 15, at least 20, at least 25, at least 30, or more amino acids. In some embodiments, the linker comprises a sequence corresponding to a cell-adhesion peptide, including, but not limited to collagen (types I, II, and III), fibronectin, and/or laminin. For example, in some embodiments, the linker comprises a cell-adhesion peptide of collagen that comprises the sequence GFOGER (SEQ ID NO:27). In some embodiments, the linker comprises a cell-adhesion peptide of fibronectin that comprises one or more of the following sequences: RGD, PHSRN (SEQ ID NO:28), REDV (SEQ ID NO:29), and LDV. In some embodiments, the linker comprises a cell-adhesion peptide of laminin that comprises one or more of the following sequences: RGD, IKVAV (SEQ ID NO:30), YIGSR (SEQ ID NO:31), and PDSGR (SEQ ID NO:32). In some aspects, the fusion protein comprises a purification tag (e.g., a polyhistidine tag), detectable label (e.g., a fluorescent moiety or epitope tag), or both. In some embodiments, the fusion protein itself is fluorescent, for example, upon coming out of solution to form fibrils the fusion protein is fluorescent. In some embodiments, the fusion protein (e.g., Mfp5-CsgA) comprises SEQ ID NO:8. In some embodiments, the fusion protein (e.g., CsgA-Mfp3) comprises SEQ ID NO:9.

In another embodiment, fusion proteins comprising an adhesive protein and a thermal-reversible functional domain are provided. Typically, the thermal-reversible domain is one that changes conformation with a change in temperature, for example wherein the protein goes from an unstructured (soluble) state to structured (solid, gel-like) state with e.g., an increase in temperature. In some embodiments, the adhesive protein is derived from a marine organism, for example an Mfp such as Mfp3 (e.g., SEQ ID NO:1 or SEQ ID NO:3) or Mfp5 (e.g., SEQ ID NO:2 or SEQ ID NO:4). In some embodiments, the fusion protein comprises Mfp3 or Mfp5, wherein Mfp3 or Mfp5 shares homology that is at least 85%, at least 90%, at least 95%, or at least 98% identical to the wild type amino acid sequence for Mfp3 or Mfp5, respectively. In some embodiments, the thermal-reversible functional domain comprises one or more elastin-like peptide (ELP) sequences, for example VPGXG (SEQ ID NO:33), wherein X independently represents any amino acid. In some embodiments, the fusion protein comprises at least 2, at least 3, at least 4, at least 5, at least 10, at least 20, at least 40, at least 60, at least 80, at least 100, or at least 150 or more repeats of the sequence VPGXG (SEQ ID NO:33), wherein X independently represents any amino acid. In some embodiments, the fusion protein comprises a linker, as described herein.

In another embodiment, any of the inventive fusion proteins described herein further comprise one or more functional domains that promote wound healing. For example, in some embodiments a fusion protein comprising an adhesive domain and amyloid domain further comprises one or more wound healing domains, and in other aspects a fusion protein comprising an adhesive domain and a thermal-reversible domain further comprises one or more wound healing domains. In some embodiments, the one or more functional domains that promote wound healing is selected from fibronectin, histatin, epidermal growth factor (EGF), or fragments thereof. In some embodiments, the functional domain comprises a fragment of fibronectin selected from RGD, PHSRN (SEQ ID NO:28), REDV (SEQ ID NO:29), and LDV. In some embodiments, the one or more functional domains that promote wound healing is a cell-adhesion peptide selected from: a cell-adhesion peptide of collagen that comprises the sequence GFOGER (SEQ ID NO:27); and a cell-adhesion peptide of laminin that comprises one or more of the following sequences: RGD, IKVAV (SEQ ID NO:30), YIGSR (SEQ ID NO:31), and PDSGR (SEQ ID NO:32).

According to other embodiments, isolated polynucleotides are provided, for example, that encode any of the fusion proteins described herein. In some embodiments, a vector is provided, for example, a vector comprising an isolated polynucleotide of the present invention. In some aspects, the vector is suited for recombinant expression of any fusion protein described herein, for example the vector contains a promoter operably linked to a polynucleotide of the present invention that drives the overexpression of an inventive fusion protein. In some aspects, the vector is suited for overexpression of an inventive fusion protein in bacteria, yeast, or mammalian cells. In some aspects, the vector is suited for overexpression of an inventive fusion protein in *E. coli*.

In some embodiments, cells are provided, for example, cells comprising a genetic construct (e.g., a vector, or genomic modification) for expressing any fusion protein of the present invention. In some aspects, the cell is a bacterial, yeast, or mammalian cell. In some aspects, the cell is an *E. coli* cell.

In some embodiments, kits with the inventive fusion proteins or with a system for producing the inventive fusion proteins are provided. In some aspects, the kit comprises any of the fusion proteins of the present invention. In some aspects, the kit comprises an isolated polynucleotide of the present invention (e.g., an isolated polynucleotide encoding an inventive fusion protein). In some aspects, the kit comprises a vector of the present invention (e.g., a vector for recombinant expression of an inventive fusion protein). In some aspects, the kit comprises a cell of the present invention (e.g., a cell expressing an inventive fusion protein).

According to other embodiments, medical adhesives comprising one or more of the fusion proteins of the present invention or fibers thereof are provided. In some aspects, the medical adhesive further comprises one or more therapeutic agents, for example, agents that promote wound healing (e.g., growth factors and antibiotics). In some aspects, the one or more therapeutic agents is selected from the group consisting of PDGF, TGF-α, TGF-β, EGF, HGF, VEGF, FGF-1, FGF-2, KGF, IGF-1. In some aspects, the one or more therapeutic agents is selected from the group consisting of kanamycin, neomycin, polymyxin B, and bacitracin. In some embodiments, a method for bonding tissue is provided. In some aspects, the method involves contacting a tissue with an inventive medical adhesive. In some aspects, the tissue is in a subject, for example, in vivo. In some aspects, the tissue is skin, adipose tissue, an organ, cartilage, tendons, ligaments, bone, or combinations thereof. In other aspects, the tissues being bonded are in vitro.

According to other embodiments, adhesives for bonding materials underwater or in an aqueous environment are provided. In some aspects, the adhesive comprises any fusion protein of the present invention or fibers thereof. In some embodiments, the adhesive comprises additional agents, for example, antioxidants, colorant, polymers, water or another solvent.

In some embodiments, methods for bonding materials underwater using the inventive adhesives are provided. In some aspects, the methods involve contacting the materials with an inventive adhesive (e.g., any of those described in the previous paragraph). In some aspects, the materials comprise one or more aspects of a watercraft. In some aspects, the materials are underwater or are to be placed underwater.

In another embodiment, methods of attaching cells or tissue to a substrate in vitro are provided. In some aspects, the method involves contacting the substrate with a fusion protein of the present invention; and contacting the coated substrate with cells or tissue. In certain embodiments, the substrate is a plastic or glass surface, and the fusion protein coats the surface to which the cells or tissue are to be attached.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF DRAWINGS

FIG. 1A depicts a schematic illustration of two independent natural adhesive proteins: curli from E. coli and mussel foot proteins (Mfp) from mussels. (Curli, major amyloid adhesive component in E. coli, is composed of functional subunits, CsgA. CsgA itself contains five stacked strand-loop strand motifs mediated by conserved residues and can self-assemble into nanofibers via a rate-limiting nucleation step followed by fibril extension[4]. Mfp3 and Mfp5, major mussel adhesive proteins, have unstructured coil structures in solution[11,13] and are critical to underwater interfacial adhesion of mussels[2].) FIG. 1B depicts a modular design of artificial adhesive materials that was enabled by rationally fusing genes encoding the two natural adhesive elements shown in FIG. 1A. Two gene constructs (CsgA-Mfp3 and Mfp5-CsgA) were independently cloned into expression vectors using one-pot isothermal Gibson assembly and tagged with polhistidine residues to enable purification. FIG. 1C depicts a schematic illustration of the predicted cross β-strand structures for Mfp5-CsgA in solution. A similar structure was also predicted for CsgAMfp3 (FIG. 6). In both predicted structures, CsgA forms the amyloid core, with Mfp3 and Mfp5 extending from C-terminal or N-terminal as unstructured coil structures. FIG. 1D depicts illustrations of inventive fusion protein (e.g., Mfp5-CsgA) forming hierarchically assembled sticky fibers. FIG. 1E is a schematic illustration of the predicted cross-β-strand structures for CsgA-Mfp3 and Mfp5-CsgA in solution. In both predicted structures, CsgA forms the amyloid core, with Mfp3 and Mfp5 extending from CsgA's C-terminal or N-terminal, respectively, as unstructured coil structures. FIG. 1F shows that, because of amyloidogenic domains, CsgA-Mfp3 and Mfp5-CsgA monomers can self-assemble into large bundles of fibrils or hierarchical networks of filaments. As used herein, the term monomer is used interchangeably with fusion protein. CsgA domains are key to fiber self-assembly by enabling fibril extension through self-polymerization and β-strand lamination by lateral stacking, with adhesive domains Mfp3 and Mfp5 exposed on the fibril surfaces. In vitro copolymerization of the CsgA-Mfp3 and Mfp5-CsgA monomers can lead to hierarchically co-assembled structures with two different adhesive domains displayed on amyloid scaffolds, potentially recapitulating intermolecular interactions between Mfp3 and Mfp5 molecules in natural mussel adhesion systems (Lee, B. P., Messersmith, P. B., Israelachvili, J. N. & Waite, J. H. in Annual Review of Materials Research Vol. 41 99-132 (2011). Enhanced underwater adhesion is expected to arise from the synergy between the high fiber surface area of curli and adhesive residues from the Mfp domains.

FIGS. 2A-2E depict fibril models constructed for the Mfp5-CsgA and CsgA-Mfp3 constructs showing packing of monomers into cross-β structures. FIG. 2A is a bottom view of the Mfp5-CsgA construct. FIG. 2B is a side view of the Mfp5-CsgA construct. The magnified image on the right showing hidden hydrogen bonds typically formed between neighboring monomers. FIG. 2C is a top view of the CsgA-Mfp3 construct. FIG. 2D is a side view of the CsgA-Mfp3 construct. FIG. 2E is a table showing secondary structure contents of the Mfp3/Mfp5 moieties within each construct over the course of 20 nanoseconds of the replica exchange molecular dynamics simulations. In both construct models, CsgA domains mainly dominated the well-ordered amyloid cores, with disordered Mfp5 or Mfp3 domains external to the amyloid core.

FIGS. 3A-3I depict the purification, in vitro assembly, and intrinsic fluorescence of CsgA (control), CsgA-Mfp3, and Mfp5-CsgA. FIG. 3A depicts Coommassie stain SDS/PAGE and Western blot with anti-His immunolabeling to confirm the expressed proteins purified by a disposable column packed with cobalt resin beads. Lanes 1, 3, and 5 represent data from SDS/PAGE, while lanes 2, 4, and 6 refer to data from western blot. The theoretical molecular weight of CsgA, CsgA-Mfp3, and Mfp5-CsgA are 14, 20.4 and 23.4 kDa, respectively; FIG. 3B depicts a thioflavin T (THT) assay used to monitor amyloid formation of the three samples; FIGS. 3C-3E depict TEM images of purified CsgA (FIG. 3C), CsgA-Mfp3 (FIG. 3D) and Mfp5-CsgA (FIG. 3E) after three-day solution incubation at 4° C.; FIG. 3F depicts fiber diameter plot of three proteins based on TEM images; FIG. 3G depicts the excitation and emission spectra of three adhesive proteins. Excitation spectra were measured with the detection wavelength fixed at 375 nm, while emission spectra were measured with the excitation wavelength fixed at 300 nm; FIG. 3H depicts the emission spectra of Mfp5-CsgA measured at different excitation wavelengths; FIG. 3I depicts the intrinsic blue fluorescence of Mfp5-CsgA proteins detected with standard imaging system by applying a EBFP fluorescence filter (excitation wavelength 385 nm, and emission wavelength 448 nm). Scale bar 20 μm.

FIG. 4A depicts a schematic illustration of a spherulitic particle AFM probe (R=10 μm, Novascan, USA) used to measure adhesion between the probe and nanofibers that were deposited on a smooth mica surface in the presence of buffered aqueous solution. FIG. 4B depicts a comparison of adhesion force (normalized force, F/R) and adhesion energy ($E_{ad}=F_{ad}/3\pi R$) for CsgA, CsgA-Mfp3, Mfp5-Csg3, and Mfp5 (literature data, on mica surface). Recordings obtained for F/R (10.8±1.7, 37.1±6.9, 127.1±24.2) and $W_{ad}$ (1.15±0.18, 3.94±0.73, 13.7±2.6 mJ/m$^2$). FIG. 4C depicts the typical force curve (including extension, dwell towards, and retraction curve) recorded for CsgA-Mfp3. FIG. 4D depicts the typical force curve recorded for Mfp5-CsgA. The insets in FIGS. 4C and 4D, respectively, show a histogram of adhesive force distribution corresponding to CsgA-Mfp3 (FIG. 4C) and Mfp5-CsgA (FIG. 4D) sample measured at different locations on mica surface. Note: Y-axis in the curves of (FIG. 4C) and (FIG. 4D) were both normalized into normalized force (left) and energy (right), the shape of the original force curve doesn't change after normalization.

FIG. 5A depicts top and side views of a single strand-loop-strand motif, as well as all five motifs stacked. FIG. 5B depicts the predicted amino acids (without the N-terminal start codon and Sec sequence shown) making up each strand of the five stacked strand-loop-strand motifs of CsgA (adapted from Collinson[31] and Barnhart[32]). The sequences, from top to bottom, correspond to SEQ ID NO:13, SEQ ID NO:14, SEQ ID NO:15, SEQ ID NO:16, SEQ ID NO:17, and SEQ ID NO:18.

FIGS. 9A-9D depict TEM and AFM images illustrating that the hierarchical structures formed by CsgA-Mfp3. FIG. 9A shows that adhesive nanofibers formed after overnight incubation. FIG. 9B shows that incubation with freshly made soluble CsgA-Mfp3 proteins in the presence of seeded adhesive nanofibers shown in (FIG. 9A) led to thick fiber bundles shown in (FIG. 9B) after 3 days. FIG. 9C shows that dense film-like structures composed of fibril structures formed after continuous incubation of freshly made soluble CsgA-Mfp3 proteins for 2 weeks in the presence of seeded adhesive nanofibers shown in (FIG. 9A). This phenomenon is due to the self-polymerization of CsgA-Mfp3 monomers over nucleation sites. Each fibril itself is composed of folded monomer having beta-sheet structures (FIG. 9D). In AFM imaging (FIG. 9D), the beta-sheet is perpendicular to the long fiber axis. Each fibril is comprised of folded monomers having beta-sheet structures.

FIGS. 10A-10C depict TEM images illustrating that assembled films (FIG. 10A) composed of interconnected fiber bundles (FIG. 10B), with each individual fiber comprising several fibril structures (FIG. 10C). Samples were prepared by incubation of concentrated (120 μM) Mfp5-CsgA solution overnight at ambient conditions. FIG. 10B is a magnified image of the boxed area shown in (FIG. 10A). In FIG. 10C, the white arrows show that large fibers are composed of individual fibrils laterally stacked together.

FIG. 12A shows a typical force curve recorded for CsgA samples. Y-axis in the curve is both normalized into normalized force (left) and energy (right), the shape of the original force curve doesn't change after normalization. FIG. 12B is a histogram of adhesive force distribution corresponding to CsgA sample measured at different locations on a mica surface.

FIG. 13A is AFM imaging showing that fibers covered the mica surface after absorption for one hour. Only 2 μL of 10 μM CsgA-Mfp3 solution was used for imaging. The sample was also imaged in phosphate buffer solution (pH 5.0) under air condition at room temperature. FIG. 13B is AFM imaging showing fibrous structures of CsgA-Mfp3 by directly imaging the measured sites under aqueous solutions with contact mode AFM tips. This result confirmed that the measured sites contained absorbed fibrous structures.

FIG. 14A shows typical force-distance curves for one big spot (60 μm size) recorded on a clean mica surface with no proteins deposited. A corresponding force histogram was plotted below. Notice that all force values are less than 30 nN. FIG. 14B shows typical force-distance curves for one big spot (60 μm size) recorded on Mfp3-CsgA sample absorbed on mica surface. A corresponding force histogram is plotted below. Notice that no force value less than 25 nN was found, this was due to measurement on some areas that were not absorbed with fibrous structures, as confirmed with AFM imaging.

FIG. 17A shows the start and end simulated structures for the CsgA-Mfp3 monomer (top) and fibril (bottom). FIG. 17B shows the start and end simulated structures for the Mfp5-CsgA monomer (top) and fibril (bottom). FIG. 17C shows the start and end simulated structures for (CsgA-Mfp3)-(Mfp5-CsgA) fibril (bottom), which are assembled via copolymerization of CsgA-Mfp3 and Mfp5-CsgA (top). For both monomeric and fibrillar states of the constructs, the start and end structures display similar structures: the CsgA domains always dominate the well-ordered amyloid cores, while disordered Mfp5 or Mfp3 domains are external to the amyloid cores. The simulation times for the monomeric and the fibrillar structures were 1 μs and 200 ns, respectively.

FIGS. 18A-18F show the purification, in vitro self-assembly and characterization of CsgA, CsgA-Mfp3, Mfp5-CsgA, and (CsgA-Mfp3)-(Mfp5-CsgA) fibers. FIG. 18A shows that Coomassie-stained SDS/PAGE gels and Western blots with anti-His antibodies confirm purification of the expressed proteins by cobalt-resin columns. Lanes 1, 3, 5, 7 and 9 represent data from SDS/PAGE, while lanes 2, 4, 6, 8 and 10 refer to corresponding data from Western blots. In FIG. 18B, MALDI-TOF confirms the molecular weights of CsgA-Mfp3 (unmodified and modified) and Mfp5-CsgA (unmodified and modified), which are consistent with the predicted molecular weights. The term "modified" means some or all of the tyrosine residues of the proteins are converted to DOPA residues and "unmodified means that the tyrosine residues have not been converted to DOPA. In FIG. 18C, the Congo red (CR) assay confirms the amyloidogenic features of all fibers, while the Nitro Blue Tetrazolium (NBT) assay detects Dopa residues in modified fibers only. FIG. 18D shows the quantitative analysis of Dopa residues in modified samples by acid-borate difference spectrum (ABDS) analysis and amino acid analysis (AAA) (N=3). In FIG. 18E, a Thioflavin T (ThT) assay reveals the kinetics of amyloid formation for CsgA, CsgAMfp3 (unmodified and modified), and Mfp5-CsgA (unmodified and modified), respectively. FIG. 18F presents TEM images of purified CsgA, CsgA- Mfp3 (unmodified and modified), Mfp5-CsgA (unmodified and modified), and (CsgA-Mfp3)-(Mfp5-CsgA) (unmodified and modified) solutions after three-day incubations at 4° C. demonstrating the formation of self-assembled fibers in all cases. CsgA-Mfp3, Mfp5-CsgA, and (CsgA-Mfp3)-(Mfp5-CsgA) fibers all had larger diameters than CsgA fibers based on measurements from TEM images. Significant differences were detected between unmodified and modified (CsgA-Mfp3)-(Mfp5-CsgA) fibers, while no significant differences were found among unmodified and modified fibers of the other two types (P<0.05). The error bars represent standard deviations (SD) of the fiber diameters (N=50). The copolymer refers to fiber structures formed via copolymerization of CsgA-Mfp3 and Mfp5-CsgA at a molar ratio 1:1 (15 μM:15 μM) in solution.

FIGS. 19A-19D show the intrinsic fluorescence of CsgA, CsgA-Mfp3, Mfp5-CsgA, and (CsgAMfp3)-(Mfp5-CsgA) copolymer fibers. FIG. 19A is a comparison of intrinsic blue fluorescence of CsgA with both unmodified and modified samples of CsgA-Mfp3, Mfp5-CsgA, and copolymer fibers, detected with fluorescence microscopy with an EBFP fluorescence filter (excitation wavelength of 385 nm, and emission wavelength of 448 nm). Corresponding fluorescence quantum yields (ratios of photons absorbed to photons emitted) were determined following the standard Williams comparative method. Scale bar represents 20 μm. FIG. 19B shows the excitation and emission spectra of CsgA, CsgA-Mfp3 (unmodified and modified), Mfp5-CsgA (unmodified and modified), and copolymer (unmodified and modified) fibers. Excitation spectra were measured with the emission wavelength fixed at 375 nm, while emission spectra were measured with the excitation wavelength fixed at 300 nm. FIG. 19C shows the emission spectra of modified Mfp5-CsgA fibers measured at different excitation (exc) wavelengths. FIG. 19D shows the excitation and emission spectra for freshly made Mfp5-CsgA solutions as well as Mfp5-CsgA solutions aged for 2 weeks. No fluorescence features were detected with freshly made Mfp5-CsgA. The two peaks in the curves for freshly made Mfp5-CsgA could be assigned to Raman peaks for water[54]. In contrast, significant fluorescence signals were detected in solution after Mfp5-CsgA solutions were aged for two weeks, during which fibers formed. The fluorescence signal of aged solutions almost covered the Raman peaks assigned to water. The copolymer refers to fiber structures that formed via copolymerization of CsgA-Mfp3 and Mfp5-CsgA at a molar ratio 1:1 (15 μM:15 μM) in solution.

FIGS. 20A-20D show the adhesion force measurements and adhesion stability of hybrid adhesive fibers determined by the atomic force microscopy (AFM) colloidal probe technique. FIG. 20A is a schematic illustration of a spherulitic particle AFM probe (R=10 μm for silica and gold tips, R=12.5 μm for polystyrene tips) used to measure asymmetric adhesion of nanofibers that were deposited on smooth mica surfaces in the presence of buffered aqueous solutions. The graph on the right is a representative AFM image showing modified Mfp5-CsgA fibers one hour after deposition on a mica surface. FIG. 20B shows representative adhesion force curves collected through force mapping mode and continuous measurement mode for modified Mfp5-CsgA samples measured with silica tips. The force mapping mode enables statistical analyses of fiber adhesion based on the random measurement of spots containing nanofibers on the mica surfaces with a scanning range of 20-100 μm. The continuous measurement mode includes 20 continuous measurements on the same specific fiber spot, thus enabling assessment of the cyclic behaviour of contacts between nanofibers and probes. FIG. 20C shows representative adhesion force curves collected through force mapping mode and continuous measurement mode for modified (CsgA-Mfp3)-(Mfp5-CsgA) copolymer (1:1 ratio) measured with silica tips. FIG. 20D shows the adhesion stability of Mfp5-CsgA (unmodified and modified) fibers measured with silica tips in the presence of buffered aqueous solutions of varied pH values (left). (N=64) The graphs on the right show representative adhesion curves for both unmodified and modified samples of Mfp5-CsgA. Note: the adhesion force curves are plotted as force-displacement curves. The x-axis, Zsnsr (Z sensor), stands for the displacement between the sample surface and the resting position of the cantilever (rather than the actual distance between the sample surface and the AFM tip).

FIG. 21A is a comparison of adhesion forces (normalized force (Force/Radius) and adhesion energies (Ead=F/3πR)) for CsgA (control) with unmodified and modified versions of functionalized adhesive fibers measured with the use of silica, gold, and polystyrene (PS) tips, respectively. FIG. 21B shows the effects of AFM tips with varied surface energies on the adhesion properties of all adhesive fibers, including CsgA and unmodified and modified versions of CsgAMfp3, Mfp5-CsgA, and (CsgA-Mfp3)-(Mfp5-CsgA) copolymer (1:1 ratio). * P<0.05, ** P<0.01. The error bars in the figure represent standard deviations (SD). The number of measurements for each statistical analysis was 64 (4 groups×16 random spots/group). All data collected in this figure were measured under force mapping mode in phosphate buffer at pH=5.0. FIGS. 21A and 21B contain the same data plotted in two different formats to enable convenient comparisons. In a), the asterisk (*) for CsgA versus unmodified fibers indicates three independent tests between CsgA and the three different fibers, while 1-1, 2-2 and 3-3 refer to comparisons between unmodified and modified samples for the same type of fiber. FIG. 21C shows the effects of AFM tips of varied surface energies on the adhesion properties of CsgA fibers. Comparison of adhesion forces (normalized force, Force/Radius) and adhesion energies (Ead=F/3πR) for CsgA fibers, measured with silica, gold, and PS tips, respectively. These data are the same as those shown in FIGS. 21A and 21B. FIG. 21D show representative normalized force and energy curves for CsgA fibers measured with silica, gold, and PS tips, respectively. Force measurements were carried out under force mapping mode in phosphate buffer solution at pH=5.0. FIG. 21E shows the effects of AFM tips of varied surface energies on the adhesion properties of both unmodified and modified versions of CsgA-Mfp3 fibers. Comparison of adhesion forces (normalized force, Force/Radius) and adhesion energies (Ead=F/3πR) for CsgA-Mfp3 (unmodified and modified) fibers, measured with silica, gold, and PS tips, respectively. (* P<0.05). These data are the same as shown in FIGS. 21A and 21B. FIG. 21F shows representative normalized force and energy curves for CsgA-Mfp3 (unmodified and modified) fibers measured with silica, gold, and PS tips, respectively. Force measurements were carried out under force mapping mode in phosphate buffer solution at pH=5.0. FIG. 21G shows the effects of AFM tips of varied surface energies on the adhesion properties of both unmodified and modified versions of Mfp5-CsgA fibers. Comparison of adhesion forces (normalized force, Force/Radius) and adhesion energies (Ead=F/3πR) for Mfp5-CsgA (unmodified and modified) fibers, measured with silica, gold, and PS tips, respectively.

(* P<0.05). These data are the same as shown in FIGS. 21A and 21B. FIG. 21H shows representative normalized force and energy curves for Mfp5-CsgA (unmodified and modified) fibers measured with silica, gold, and PS tips, respectively. Force measurements were carried out under force mapping mode in phosphate buffer solution at pH=5.0. FIG. 21I shows the effects of AFM tips of varied surface energies on the adhesion properties of both unmodified and modified copolymer fibers (1:1 ratio). Comparison of adhesion forces (normalized force, Force/Radius) and adhesion energies (Ead=F/3πR) for copolymer fibers (molar ratio of CsgA-Mfp3:Mfp5-CsgA=15 µM:15 µM), measured with silica, gold, and PS tips, respectively. (* P<0.05). These data are the same as those shown in FIGS. 21A and 21B. FIG. 21J shows representative normalized force and energy curves for copolymer fibers measured with silica, gold, and PS tips, respectively. Force measurements were carried out under force mapping mode in phosphate buffer solution at pH=5.0.

FIG. 22A shows the MALDI-TOF of CsgAMfp3 (unmodified). MW=20241. FIG. 22B shows the MALDI-TOF of CsgA-Mfp3 (modified), acidified sample. MW=20427. FIG. 22C shows the MALDI-TOF of CsgA-Mfp3 (modified), borate buffer sample. MW=20583. FIG. 22D shows the MALDI-TOF of Mfp5-CsgA (unmodified). MW=23420.4. FIG. 22E shows the MALDI-TOF of Mfp5-CsgA (modified), acidified sample. MW=23733. FIG. 22F shows the MALDI-TOF of Mfp5-CsgA (modified), borate buffer sample. MW=23892. Acidified sample: the protein sample used for analysis was prepared from an acidic HFIP solution. Borate buffer sample: the protein sample used for analysis was prepared from a borate buffer solution. In agreement with the predicted MWs, the actual MWs for both CsgAMfp3 and Mfp5-CsgA increased after post-modification (tyrosine transformed into Dopa). For the same modified protein, the MW from the borate samples were higher than the MWs of the acidified samples due to the formation of diol-borate bonds compared with the two independent hydroxyl groups. Such observations were not found for the unmodified samples. Note: Apomyoglobin (MW=16952.6) was used as an internal standard for accurate MW labeling of the adhesion proteins.

FIG. 23A shows acid-borate difference spectra of the L-dopa standard with different concentrations in acid and borate buffers (left). Plot of absorptivity difference vs. concentration of L-dopa (right). FIG. 23B shows the acid-borate difference spectrum for CsgA-Mfp3. FIG. 23C shows the acid-borate difference spectrum of Mfp5-CsgA. The maximal absorptivity difference between the borate and acid curves occurs at 292 nm for free dopa and 294 for dopa-containing peptides or proteins.

FIGS. 24A-24C show adhesive force comparisons measured at two different solution pH values (pH=2.5 and 5.0) for (FIG. 24A) CsgA, (FIG. 24B) CsgA-Mfp3 (modified), (FIG. 24C) Table showing the mean adhesive forces and corresponding standard deviations (SD) for CsgA and CsgA-Mfp3 fibers.

FIG. 25A is a comparison of adhesion forces (normalized force, Force/Radius) and adhesion energies (Ead=F/3πR) for copolymer fibers constituted from two monomer proteins (CsgA-Mfp3 vs. Mfp5-CsgA) with molar ratio, 3:7, 5:5, and 7:3, respectively. The data for the molar ratio 5:5 is the same as shown in FIGS. 21A and 21B. FIG. 25B shows representative normalized force curves for copolymer fibers with varied monomer ratios. Force measurements were carried out under force mapping mode with the use of silica tips in phosphate buffer solution at pH=5.0.

FIGS. 26A-26C show representative force maps and corresponding force distance curves recorded with CsgA samples adsorbed on a mica surface measured with (FIG. 26A) silica; (FIG. 26B) Au; and (FIG. 26C) PS tips, respectively. Force measurements were carried out in phosphate buffer solution at pH=5.0.

FIGS. 27A-27C show representative force maps and corresponding force distance curves recorded with unmodified CsgA-Mfp3 samples adsorbed on a mica surface measured with (FIG. 27A) silica; (FIG. 27B) Au; and (FIG. 27C) PS tips, respectively. Force measurements were carried out in phosphate buffer solution at pH 5.0.

FIGS. 28A-28C show representative force maps and corresponding force distance curves recorded with unmodified Mfp5-CsgA samples adsorbed on a mica surface measured with (FIG. 28A) silica; (FIG. 28B) Au; and (FIG. 28C) PS tips, respectively. Force measurements were carried out in phosphate buffer solution at pH 5.0.

FIGS. 29A-29C show representative force maps and corresponding force-distance curves recorded with unmodified copolymer samples (1:1 molar ratio) adsorbed on a mica surface measured with (FIG. 29A) silica; (FIG. 29B) Au; and (FIG. 29C) PS tips, respectively. Force measurements were carried out in phosphate buffer solution at pH 5.0.

FIGS. 30A-30C show typical force maps and corresponding force-distance curves recorded with modified CsgA-Mfp3 samples adsorbed on a mica surface measured with (FIG. 30A) silica; (FIG. 30B) Au; and (FIG. 30C) PS tips, respectively. Force measurements were carried out in phosphate buffer solution at pH 5.0.

FIGS. 31A-31C show typical force maps and corresponding force-distance curves recorded with modified Mfp5-CsgA samples adsorbed on a mica surface measured with (FIG. 31A) silica; (FIG. 31B) Au; and (FIG. 31C) PS tips, respectively. Force measurements were carried out in phosphate buffer solution at pH 5.0.

FIGS. 32A-32C show typical force maps and corresponding force-distance curves recorded with modified copolymer samples (1:1 ratio) adsorbed on a mica surface measured with (FIG. 32A) silica; (FIG. 32B) Au; and (FIG. 32C) PS tips, respectively. Force measurements were carried out in phosphate buffer solution at pH 5.0.

DEFINITIONS

Figure 1A:
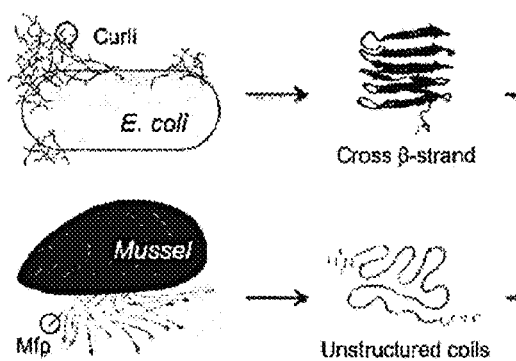
FIGS. 1A-1F depict the use of synthetic biology to engineer self-assembling underwater adhesives.

The term "agent," as used herein, refers to any molecule, entity, or moiety. For example, an agent may be a protein, an amino acid, a peptide, a polynucleotide, a carbohydrate, a lipid, a detectable label, a binding agent, a tag, a metal atom, a contrast agent, a catalyst, a non-polypeptide polymer, a synthetic polymer, a recognition element, a linker, or chemical compound, such as a small molecule. Additional agents suitable for use in embodiments of the present invention will be apparent to the skilled artisan. The invention is not limited in this respect.

The term "amino acid," as used herein, includes any naturally occurring and non-naturally occurring amino acid. Suitable natural and non-natural amino acids will be apparent to the skilled artisan, and include, but are not limited to, those described in S. Hunt, The Non-Protein Amino Acids: In *Chemistry and Biochemistry of the Amino Acids*, edited by G. C. Barrett, Chapman and Hall, 1985. Some non-limiting examples of non-natural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; —CH$_3$), disubstituted phenylalanines, substituted tyrosines (e.g., further substituted with —C(=O)C$_6$H$_5$; —CF$_3$; —CN; -halo; —NO$_2$; —CH$_3$), and statine. In the context of amino acid sequences, "X" or "Xaa" represents any amino acid residue, e.g., any naturally occurring and/or any non-naturally occurring amino acid residue.

The term "conjugated" or "conjugation" refers to an association of two entities, for example, of two molecules such as two proteins, or a protein and a reactive handle, or a protein and an agent, e.g., a detectable label. The association can be, for example, via a direct or indirect (e.g., via a linker) covalent linkage or via non-covalent interactions. In some embodiments, the association is covalent. In some embodiments, two molecules are conjugated via a linker connecting both molecules. For example, in some embodiments where two proteins are conjugated to each other to form a fusion protein, the two proteins may be conjugated via a polypeptide linker, e.g., an amino acid sequence connecting the C-terminus of one protein to the N-terminus of the other protein.

The term "detectable label" refers to a moiety that has at least one element, isotope, or functional group incorporated into the moiety which enables detection of the molecule, e.g., a protein or peptide, or other entity, to which the label is attached. Labels can be directly attached or can be attached via a linker. It will be appreciated that the label may be attached to or incorporated into a molecule, for example, a protein, polypeptide, or other entity, at any position. In general, a detectable label can fall into any one (or more) of five classes: I) a label which contains isotopic moieties, which may be radioactive or heavy isotopes, including, but not limited to, $^2$H, $^3$H, $^{13}$C, $^{14}$C, $^{15}$N, $^{18}$F, $^{31}$P, $^{32}$P, $^{35}$S, $^{67}$Ga, $^{76}$Br, $^{99m}$Tc (Tc-$^{99}$m), $^{111}$In, $^{123}$I, $^{125}$I, $^{131}$I, $^{153}$Gd, $^{169}$Yb, and $^{186}$Re; II) a label which contains an immune moiety, which may be antibodies or antigens, which may be bound to enzymes (e.g., such as horseradish peroxidase); III) a label which is a colored, luminescent, phosphorescent, or fluorescent moieties (e.g., such as the fluorescent label fluorescein-isothiocyanate (FITC); IV) a label which has one or more photo affinity moieties; and V) a label which is a ligand for one or more known binding partners (e.g., biotin-streptavidin, FK506-FKBP). In certain embodiments, a label comprises a radioactive isotope, preferably an isotope which emits detectable particles, such as β particles. In certain embodiments, the label comprises a fluorescent moiety. In certain embodiments, the label is the fluorescent label fluorescein-isothiocyanate (FITC). In certain embodiments, the label comprises a ligand moiety with one or more known binding partners. In certain embodiments, the label comprises biotin, which may be detected using a streptavidin conjugate (e.g., fluorescent streptavidin conjugates such as Streptavidin ALEXA FLUOR® 568 conjugate (SA-568) and Streptavidin ALEXA FLUOR® 800 conjugate (SA-800), Invitrogen). In some embodiments, a label is a fluorescent polypeptide (e.g., GFP or a derivative thereof such as enhanced GFP (EGFP)) or a luciferase (e.g., a firefly, Renilla, or Gaussia luciferase). It will be appreciated that, in certain embodiments, a label may react with a suitable substrate (e.g., a luciferin) to generate a detectable signal. Non-limiting examples of fluorescent proteins include GFP and derivatives thereof, proteins comprising fluorophores that emit light of different colors such as red, yellow, and cyan fluorescent proteins. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M. and Kain, S R (eds.) Green fluorescent protein: properties, applications, and protocols Methods of biochemical analysis, v. 47 Wiley-Interscience, Hoboken, N.J., 2006; and Chudakov, D M, et al., Physiol Rev. 90(3):1103-63, 2010, for discussion of GFP and numerous other fluorescent or luminescent proteins. In some embodiments, a label comprises a dark quencher, e.g., a substance that absorbs excitation energy from a fluorophore and dissipates the energy as heat.

The term "homologous," as used herein is an art-understood term that refers to nucleic acids or polypeptides that are highly related at the level of nucleotide or amino acid sequence. Nucleic acids or polypeptides that are homologous to each other are termed "homologues." Homology between two sequences can be determined by sequence alignment methods known to those of skill in the art. In accordance with the invention, two sequences are considered to be homologous if they are at least about 50-60% identical, e.g., share identical residues (e.g., amino acid residues) in at least about 50-60% of all residues comprised in one or the other sequence, at least about 70% identical, at least about 80% identical, at least about 90% identical, at least about 95% identical, at least about 98% identical, at least about 99% identical, at least about 99.5% identical, or at least about 99.9% identical, for at least one stretch of at least 20, at least 30, at least 40, at least 50, at least 60, at least 70, at least 80, at least 90, at least 100, at least 120, at least 150, or at least 200 amino acids. The "percent identity" of two nucleic acid or two amino acid sequences can be determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST nucleic acid or protein searches can be performed with the XBLAST program, score=50, wordlength=3 to obtain sequences homologous to the nucleic acid or protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

As used herein, the term "host cell" covers any kind of cellular system which can be used or engineered to generate proteins, protein fragments, fusion proteins, or peptides of interest. Host cells include, without limitation, cultured cells, e.g., bacterial cells (e.g., *Escherichia coli, Corynebac-* terium, *Pseudomonas fluorescens*); mammalian cultured cells derived from rodents (e.g., rats, mice, guinea pigs, or hamsters) such as CHO, BHK, NSO, SP2/0, YB2/0; or human tissues or hybridoma cells, yeast cells, and insect cells, but also cells within a transgenic animal or cultured tissue. In some embodiments, "host cell" is used interchangeably with "cell."

The term "linker," as used herein, refers to a chemical group or molecule covalently linked to a molecule, for example, a protein, and a chemical group or moiety, for example, a click chemistry handle. In some embodiments, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker comprises a sequence corresponding to a cell-adhesion peptide, including, but not limited to collagen (types I, II, and III), fibronectin, and/or laminin. For example, in some embodiments, the linker comprises a cell-adhesion peptide of collagen that comprises the sequence GFOGER (SEQ ID NO:27). In some embodiments, the linker comprises a cell-adhesion peptide of fibronectin that comprises one or more of the following sequences: RGD, PHSRN (SEQ ID NO:28), REDV (SEQ ID NO:29), and LDV. In some embodiments, the linker comprises a cell-adhesion peptide of laminin that comprises one or more of the following sequences: RGD, IKVAV (SEQ ID NO:30), YIGSR (SEQ ID NO:31), and PDSGR (SEQ ID NO:32). In some embodiments, the linker is an organic molecule (e.g., peptoid), polymer (e.g., PEG, polyester, polyester amides (PEA)), branched molecule (e.g., dendrimer), or chemical moiety.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. It should be appreciated that methods for making the amino acid substitutions (mutations) provided herein are well known in the art, and are provided by, for example, Green and Sambrook, *Molecular Cloning: A Laboratory Manual* ($4^{th}$ ed., Cold Spring Harbor Laboratory Press, Cold Spring Harbor, N.Y. (2012)).

The term "nucleic acid molecule," or "polynucleotide," refers to the phosphate ester form of ribonucleotides (RNA molecules) or deoxyribonucleotides (DNA molecules), or any phosphodiester analogs, in either single-stranded form, or a double-stranded helix. Double-stranded DNA-DNA, DNA-RNA and RNA-RNA helices are possible. The term nucleic acid molecule, and in particular DNA or RNA molecule, refers to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described according to the normal convention of giving only the sequence in the 5' to 3' direction along the nontranscribed strand of DNA (i.e., the strand having a sequence homologous to the mRNA).

A "recombinant nucleic acid molecule" is a nucleic acid molecule that has undergone a molecular biological manipulation, i.e., non-naturally occurring nucleic acid molecule or genetically engineered nucleic acid molecule. Furthermore, the term "recombinant DNA molecule" refers to a nucleic acid sequence which is not naturally occurring, or can be made by the artificial combination of two otherwise separated segments of nucleic acid sequence, i.e., by ligating together pieces of DNA that are not normally continuous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al., Molecular Cloning, second edition, Cold Spring Harbor Laboratory, Plainview, N.Y.; (1989), or Ausubel et al., Current Protocols in Molecular Biology, Current Protocols (1989), and DNA Cloning: A Practical Approach, Volumes I and II (ed. D. N. Glover) IREL Press, Oxford, (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid segments of desired functions to generate a single genetic entity comprising a desired combination of functions not found in the common natural forms. Restriction enzyme recognition sites are often the target of such artificial manipulations, but other site specific targets, e.g., promoters, DNA replication sites, regulation sequences, control sequences, open reading frames, or other useful features may be incorporated by design. Examples of recombinant nucleic acid molecule include recombinant vectors, such as cloning or expression vectors which contain DNA sequences encoding R or family proteins or immunoglobulin proteins which are in a 5' to 3' (sense) orientation or in a 3' to 5' (antisense) orientation.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively.

The term "subject" refers to any animal. A subject may be a mammal, which includes human, or non-human subjects. Non-human subjects can include experimental, test, agricultural, entertainment or companion animals. A subject may be a human. A subject may be a domesticated animal, such as a dog, cat, cow, goat, sheep, pig, etc. A subject may be an experimental animal, such as a mouse, rat, rabbit, monkey, etc.

The term "vector" refers to a polynucleotide comprising one or more recombinant polynucleotides of the present invention, e.g., those encoding a fusion protein provided herein. Vectors include, but are not limited to, plasmids, viral vectors, cosmids, artificial chromosomes, and phagemids. The vector is one which is able to replicate in a host cell, and which is further characterized by one or more endonuclease restriction sites at which the vector may be cut and into which a desired nucleic acid sequence (e.g., Mfp-CsgA) may be inserted. Vectors may contain one or more marker sequences suitable for use in the identification and/or selection of cells which have or have not been transformed or genomically modified with the vector. Markers include, for example, genes encoding proteins which increase or decrease either resistance or sensitivity to antibiotics (e.g., kanamycin, ampicillin) or other compounds, genes which encode enzymes whose activities are detectable by standard assays known in the art (e.g., β-galactosidase, alkaline phosphatase or luciferase), and genes which visibly affect the phenotype of transformed or transfected cells, hosts, colonies, or plaques. Any vector suitable for the transformation of a host cell, (e.g., E. coli, mammalian cells such as CHO cell, insect cells, etc.) are embraced by the present invention, for example vectors belonging to the pUC series, pGEM series, pET series, pBAD series, pTET series, or pGEX series. Typically, the vector includes a promoter (e.g., a constitutive or inducible promoter) operably linked to a polynucleotide which is capable of driving the overexpression of an inventive fusion protein. As used herein "operably linked" includes reference to a functional linkage between a promoter and a second sequence (e.g., a polynucleotide encoding an inventive fusion protein), wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

DETAILED DESCRIPTION OF CERTAIN EMBODIMENTS OF THE INVENTION

The development of advanced artificial adhesives is currently motivated by an increased understanding of naturally occurring underwater adhesives used by living marine organisms.[1,12] Mussel-mimic adhesives have attracted particular attention because of their wet bonding strength and high durability[2,12], leading to several molecular investigations into mussel adhesion.[2,11,13] Because 3,4-dihydroxyphenylalanine (DOPA) has been considered an essential component of the mussel holdfast proteins, research efforts have thus far been directed toward the development of DOPA-containing or DOPA analogue-containing peptides, small molecules, or polymer constructs[7,12]. Further findings about basic residues such as lysine between DOPA residues have contributed to subsequent development of polydopamine (pDA)[10], nitrocatecholamines,[14] and copolymers containing both DOPA and lysine residues.[6]

Although current mussel-mimetic adhesives are promising, they suffer from several limitations that restrict their practical application. First, the DOPA and/or lysine residues in synthetic adhesives do not fully capture the functional adhesive properties of native proteins, thereby producing inconsistent underwater adhesion performance or insufficient wet bonding strength. Furthermore, synthetic adhesives are often susceptible to mechanical abrasion due to insufficient robustness[12]. Recent attempts to push these limits with recombinant DNA techniques have led to variants of recombinant mussel foot proteins,[8,9] but they, too, have shown similar deficiencies.

Nature, however, provides alternative solutions for underwater adhesion that don't involve DOPA but still capitalizes on functional proteins. Certain marine invertebrates including algae, barnacles, and parasitic marine flatworms, harness functional folded amyloid structures as underwater glues[3]. Amyloids or amyloid fibers are aggregates of proteins or peptides characterized by beta-strands that are oriented perpendicularly to the fibril axis and stacked parallel to the fiber axis and are connected through a dense hydrogen-bonding network, which leads to supramolecular beta-sheets that usually extend continuously over thousands of molecular units (see Wasmer, C. et al. Science 319, 1523-1526, (2008); Sawaya, M. R. et al. Nature 447, 453-457, (2007); Knowles, T. P. J. & Buehler, M. J. Nature Nanotechnology 6, (2011)). The advantages of such amyloid structures include tolerance to environmental deterioration, self-healing (e.g., arising from self-polymerization), and large fiber surface areas[15,16], which appear to enhance adhesion by increasing contact area in the adhesive plaques of barnacles[17]. In addition, there are potential mechanical benefits of amyloid structures, including the cohesive strength associated with the generic amyloid intermolecular beta-sheet structure and adhesive strength possibly related to adhesive residues external to the amyloid core3.

Rational design and synthetic-biology techniques were used to create a new generation of bio-inspired adhesives that combine two independent natural adhesion systems. In one aspect, adhesive proteins (e.g., dopa-based adhesive proteins) derived from an organism (e.g., a marine organism) are combined with amyloid-based adhesive proteins. CsgA is a representative example of an amyloid-like adhesive protein, and Mfp3 and Mfp5 are representative examples of adhesive proteins derived from a marine organism. Thus, provided herein are inventive fusion proteins, and fibers thereof that are prepared from adhesive proteins (e.g., dopa-based adhesive proteins) derived from an organism (e.g., a marine organism), or fragments thereof, and amyloid-based adhesive proteins, or fragments thereof.

Accordingly, aspects of the present invention relate to fusion proteins, fusion protein copolymers, and/or fiber adhesives engineered to incorporate the benefits of diverse proteins such as Mfps and amyloids. The fusion proteins, fusion protein copolymers, and/or fibers provided herein exhibit superior and unexpected properties as compared to their natural counterparts and synthetic or recombinant biomimetic adhesives known in the art. For example, provided fusion proteins, fusion protein copolymers, and fibers (e.g., Mfp5-CsgA) display adhesion energies that can be four to ten times higher than those of the individual proteins making up the fusion. Additionally, it was unexpectedly found that the fusion proteins, fusion protein copolymers, and/or fibers exhibit intrinsic fluorescence signatures in the visible spectrum range, which in some embodiments provides for additional benefits in certain applications, as discussed herein. The fusion proteins can assemble into large bundles of fibrils (fibers) or hierarchical networks of filaments. Accordingly, also provided herein are fibers prepared from at least one type of fusion protein described herein. Also provided are fibers prepared from at least two types of fusion proteins co-assembled to form copolymer fiber structures. The copolymer fibers described herein have strong underwater adhesion (generally with an adhesion energy of at least about 5 mJ/m² or at least about 10 mJ/m² on silica surfaces), outperforming known bio-derived and bio-inspired protein-based underwater adhesives. The protein-based amyloid fibrils or fibers provided herein are made up of repeating subunits of fusion proteins. The subunits containing an amyloid domain (e.g., CsgA) self-assemble through self-polymerization and beta-strand lamination by lateral stacking. A fiber can be made up of repeating subunits of one type of fusion protein. For example, in certain embodiments, a fiber can be made up of only CsgA subunits (a CsgA fiber or curli fiber), only CsgA-Mfp3 subunits, or only Mfp5-CsgA subunits. A fiber can be made up of repeating subunits of at least two types of fusion proteins. For example, in certain embodiments, a fiber can be made up of CsgA-Mfp3 subunits and Mfp5-CsgA subunits (referred to as a CsgA-Mfp3-co-Mfp5-CsgA copolymer).

Other aspects of this invention relate to isolated polynucleotides and vectors encoding a fusion protein of the present invention (e.g., for recombinant expression of a fusion protein); cells comprising a genetic construct encoding a fusion protein; kits comprising inventive fusion proteins, fusion protein copolymers, and/or fibers thereof, and/or vectors and/or cells; as well as compositions for use as adhesives (e.g., medical, marine, plumbing, etc.) and/or coatings (e.g., coatings for cell culture dishes) and methods of their use.

Adhesive Fusion Proteins and Fibers

Aspects of the present invention provide novel fusion proteins, copolymers, and fibers thereof (collectively referred to as "adhesives") useful as adhesives in a variety of settings, e.g., in medical, marine, and/or plumbing applications. For example, the adhesives described herein are useful as medical adhesives, e.g., in a surgical application to aid in closing wounds or incisions, and in some settings, to promote wound healing. In some aspects, the inventive medical adhesives are useful in orthopedic applications, for example, to repair fractures (e.g., bond bone and/or cartilage), or to aid in joint replacements (e.g., hip, knee, ankle, shoulder, elbow, wrist, and finger arthroplasty procedures). In other aspects, the adhesives described herein having strong underwater adhesive properties are useful as underwater adhesives, for example, to bond or adhere components in a marine setting, or to secure certain fittings in a plumbing application. Some aspects of the present invention relate to the fluorescent properties of the adhesives described herein. For example, because the adhesives described herein display intrinsic fluorescence, it is possible to determine the robustness or integrity of the adhesion formed by the adhesives over time, e.g., by monitoring the amount or pattern of fluorescence at a bond interface. In a medical setting, this may allow, for example, monitoring the integrity of an implant interface of a medical device. In some aspects, the adhesives exhibits a fluorescence excitation maximum from about 300 nm to about 320 nm, and an emission maximum from about 370 nm to about 390 nm. In some aspects, the adhesive's excitation maximum is about 312 nm or about 318 nm, and the emission maximum is about 378 nm. In some aspects, the adhesive's excitation maximum is about 315 nm, and the emission maximum is about 378 nm. In some embodiments, the adhesive is a fiber composed of only Mfp5-CsgA and exhibits a fluorescence excitation maximum of about 318 nm, and an emission maximum from about 378 nm. In some embodiments, the adhesive is a fiber composed of only CsgA-Mfp3 and exhibits a fluorescence excitation maximum of about 312 nm, and an emission maximum from about 378 nm. In some embodiments, the fiber is composed of two types of fusion proteins ("copolymer fiber") such as CsgA-Mfp3 and Mfp5-CsgA, which exhibits an excitation maxima of about 315 nm, and the emission maxima of about 378 nm.

In some embodiments, the fusion proteins are comprised of two or more proteins, for example, an adhesive protein and an amyloid protein. Adhesive proteins include, without limitation, any adhesive protein produced by an organism. In some embodiments, an adhesive protein is a synthetic protein, such as a peptidomimetic, which in some embodiments is modeled on a naturally occurring adhesive protein. In some aspects, adhesive proteins include those produced by a marine organism. For example, adhesive proteins include those produced by the sandcastle worm *Phragmatopoma californica* (e.g., Pc1, Pc2, Pc3A, Pc3B, Pc4, Pc5)(see e.g., Zhao et al., Cement proteins of the tube-building polychaete *Phragmatopoma californica*. J. Biol. Chem. 2005; 280(52): 42938-42944); underwater adhesive silks such as those comprised of fibroin proteins (e.g., h-fibroin) produced by caddisflies of the order Trichoptera (e.g., *Brachycentrus echo*)(see e.g., Stewart and Wang, Adaptation of caddisfly larval silks to aquatic habitats by phosphorylation of h-fibroin serines. Biomacromolecules. 2010; 11(4):969-974), and those produced by midge larva of the genus *Chironomus* (e.g., sp-Ia, sp-Ib, sp-Ic, sp-Id)(see e.g., Kao and Case, A novel giant secretion polypeptide in chironomus salivary glands: implications for another balbiani ring gene. J. Cell Biol. 1985; 101(3):1044-1051); sea cucumber (e.g., *Holothuria forskåli*) Cuvierian tubule adhesive (see e.g., Flammang et al., Polyphosphoprotein-containing marine adhesives. J. Adhes. 2009; 85:447-464); and adhesive proteins produced by barnacles (e.g., cp-19k and cp-20k produced by *Megabalanus rosa*)(see e.g., Kamino, Molecular design of barnacle cement in comparison with those of mussel and tubeworm. J Adhes. 2010; 86:96-110). In some embodiments, the adhesive protein is a mussel foot protein (Mfp). In nature, Mfps allow mussels to attach their byssus to a variety of substrata that are wet, saline, corroded, and/or fouled by biofilms. The reactive oxidized form of DOPA, quinone, is a key amino acid for mussel underwater adhesion. DOPA is formed through post-modification of tyrosine residues via a polyphenoloxidase (tyrosinase). DOPA complexes with metal ions, metal oxides, and semimetals, such as silicon, and is thought to participate in the ability of Mfps to adhere to rocks and glass. In some embodiments, the fusion protein comprises a Mfp derived from any species of mussel known to produce such proteins, for example, those of the genus *Mytilus* (e.g., *Mytilus edulis, Mytilus galloprivincialis, Mytilus californianus, Mytilus coruscus*) and those of the genus *Perna* (e.g., *Perna canalicula, Perna perna, Perna viridis*). Variant Mfps may be referred to by the species from which they are derived—for example, Mefp is the Mfp variant from *Mytilus edulis* and Mgfp is from *M. galloprivincialis*. In some embodiments, the fusion protein comprises a Mfp derived from the species *Mytilus galloprivincialis*, and thus may interchangeably be referred to as a Mgfp. In some embodiments, the Mfp is Mfp3 (e.g., Mgfp3, SEQ ID NO:1) or Mfp5 (e.g., Mgfp5, SEQ ID NO:2). In some embodiments, the Mfp is Mefp3 (e.g., SEQ ID NO:3) or Mefp5 (e.g., SEQ ID NO:4) from *Mytilus edulis*. Mussel foot proteins, in particular Mfp3 and Mfp5, are conserved across species, and as such those skilled in the art will appreciate that fusion proteins of the present invention may comprise one or more Mfp or fragments thereof, from one or more species of mussel. Methods for expressing recombinant Mfps are known, and include those described by Hwang et al., "Expression of Functional Recombinant Mussel Adhesive Protein Mgfp-5 in *Escherichia coli*." Appl Environ Microbiol. 2004; 70(6): 3352-3359; as well as U.S. Patent Application No. 20120/0202748 A1 and U.S. Pat. Nos. 7,622,550 and 7,947,806; the entire contents of each are hereby incorporated by reference.

For sequences listed herein without a methionine as the first residue, it is understood by a person of ordinary skilled in the art that there may be a methionine as the first residue if there is a start codon present at the beginning of the corresponding nucleotide sequence.

A representative sequence for Mgfp3 is:

(SEQ ID NO: 1)
ADYYGPKYGPPRRYGGGNYNRYGRRYGGYKGWNNGWKRGRWGRKYY.

In some embodiments, the sequence comprises a polyhistidine tag, as described herein.

A representative sequence for Mgfp5 is:

(SEQ ID NO: 2)
SSEEYKGGYYPGNTYHYHSGGSYHGSGYHGGYKGKYYGKAKKYYYKYKNS

GKYKYLKKARKYHRKGYKKYYGGGSS.

In some embodiments, the sequence comprises a polyhistidine tag, as described herein.

A representative sequence for Mefp3 is:

(SEQ ID NO: 3)
ADYYGPNYGPPRRYGGGNYNRYNRYGRRYGGYKGWNNGWNRGRRGKYW.

In some embodiments, the sequence comprises a polyhistidine tag, as described herein.

A representative sequence for Mefp5 is:

(SEQ ID NO: 4)
SSEEYKGGYYPGNAYHYHSGGSYHGSGYHGGYKGKYYGKAKKYYYKYKNS

GKYKYLKKARKYHRKGYKYYGGSS.

In some embodiments, the sequence comprises a polyhistidine tag, as described herein.

In some embodiments, the fusion protein comprises a fragment of a Mfp, e.g., a fragment that maintains adhesive properties. For example, because the tyrosine residues (when converted to DOPA) are believed to contribute to the adhesive properties of Mfps, in some aspects the fragment may comprise the region(s) rich in tyrosine residues.

In some embodiments, the fusion protein comprises an amyloid protein. Amyloid proteins form robust and highly ordered self-polymerizing assemblies with large fiber surface areas that are self-healing, making them especially suited to certain applications described herein. Many organisms secrete adhesive amyloid proteins for attachment purposes or in forming an extracellular matrix. Amyloid proteins encompassed by the present invention include those that form natural adhesives, for example, those derived from bacteria (e.g., the family Enterobacteriaceae) or certain marine invertebrates including algae (e.g., *Coccomyxa* sp., *Glaphyrella trebouxiodes, Prasiola linearis, Klebsomidium flaccidum*), barnacles (e.g., *Balanus amphitrite*), and parasitic flatworms (e.g., *Entobdella soleae*). Other suitable amyloid proteins include those found in several species of yeast such as *Candida albicans* (e.g., Als1, Als3, and Als5) and *Saccharomyces cerevisiae* (e.g., Flo1 and Flo11), as well as bacteria of the genera *Pseudomonas* and *Bacillus*. In some embodiments, the amyloid protein is a bacterial curli (curlin) subunit protein, for example CsgA (curlin subunit gene A; SEQ ID NO:5) from *Escherichia coli*. A review of the curli proteins may be found in Chapter 7 of Jarvis and Mostaert's *The Functional Fold: Amyloid Structures in Nature*, pages 115-130 (Pan Stanford, 2012), the entire contents of which are incorporated herein by reference. The curli subunit proteins, in particular CsgA, are conserved across many species of the family Enterobacteriaceae, and as such those skilled in the art will appreciate that fusion proteins of the present invention may comprise one or more curli subunit proteins, or fragments thereof, from one or more species of bacteria. For example, a fusion protein of the present invention can include a CsgA homologue, e.g., AgfA from *Salmonella enteritidis*.

A representative sequence for CsgA (e.g., derived from *E. coli*) is:

(SEQ ID NO: 5)
MKLLKVAAIAAIVFSGSALAGVVPQYGGGGNHGGGGNNSGPNSELNIYQY

GGGNSALALQTDARNSDLTITQHGGGNGADVGQGSDDSSIDLTQRGFGNS

ATLDQWNGKNSEMTVKQFGGGNGAAVDQTASNSSVNVTQVGFGNNATAHQ

Y.

In some embodiments, the sequence for CsgA in a provided fusion protein lacks (e.g., residues 1-20), and comprises the sequence:

(SEQ ID NO: 7)
GVVPQYGGGGNHGGGGNNSGPNSELNIYQYGGGNSALALQTDARNSDLTI

TQHGGGNGADVGQGSDDSSIDLTQRGFGNSATLDQWNGKNSEMTVKQFGG

GNGAAVDQTASNSSVNVTQVGFGNNATAHQY.

In some embodiments, the sequence for CsgA contains one or more of the following sequence components, defined by region:

| Region | Residue #s | Sequence |
|---|---|---|
| Secretion sequence (M is the start codon) | 1-20 | MKLLKVAAIAAIVFSGSALA (SEQ ID NO: 12) (M is the start codon) |
| N | 21-42 | GVVPQYGGGGNHGGGGNNSGPN (SEQ ID NO: 13) |
| R1 | 43-65 | SELNIYQYGGGNSALALQTDARN (SEQ ID NO: 14) |
| R2 | 66-87 | SDLTITQHGGGNGADVGQGSDD (SEQ ID NO: 15) |
| R3 | 88-110 | SSIDLTQRGFGNSATLDQWNGKN (SEQ ID NO: 16) |
| R4 | 111-132 | SEMTVKQFGGGNGAAVDQTASN (SEQ ID NO: 17) |
| R5 | 133-151 | SSVNVTQVGFGNNATAHQY (SEQ ID NO: 18) |

A representative sequence for AgfA (e.g., derived from S. enteritidis) is:

```
                                              (SEQ ID NO: 6)
MKLLKVAAFAAIVVSGSALAGVVPQWGGGGNHNGGGNSSGPDSTLSIYQY

GSANAALALQSDARKSETTITQSGYGNGADVGQGADNSTIELTQNGFRNN

ATIDQWNAKNSDITVGQYGGNNAALVNQTASDSSVMVRQVGFGNNATANQ

Y
```

In some embodiments, the sequence for AgfA contains one or more of the following sequence components, defined by region:

| Region | Residue #s | Sequence |
|---|---|---|
| Secretion sequence (M is the start codon) | 1-20 | MKLLKVAAFAAIVVSGSALA (SEQ ID NO: 19) (M is the start codon) |
| N | 21-42 | GVVPQWGGGGNHNGGGNSSGPD (SEQ ID NO: 20) |
| R1 | 43-65 | STLSIYQYGSANAALALQSDARK (SEQ ID NO: 21) |
| R2 | 66-87 | SETTITQSGYGNGADVGQGADN (SEQ ID NO: 22) |
| R3 | 88-110 | STIELTQNGFRNNATIDQWNAKN (SEQ ID NO: 23) |
| R4 | 111-132 | SDITVGQYGGNNAALVNQTASD (SEQ ID NO: 24) |
| R5 | 133-151 | SSVMVRQVGFGNNATANQY (SEQ ID NO: 25) |

In some embodiments, the individual components of the fusion protein (e.g., a Mfp and amyloid protein) are directly linked to each other through an amide bond. In other embodiments, they are joined via a linker, preferably a peptidic linker or an organic linker. A peptidic linker typically has at least 1, at least 2, at least 3, at least 4, at least 5, at least 6, at least 7, at least 8, a least 9, at least 10, at least 11, at least 12, at least 13, at least 14, at least 15, at least 20, at least 25, at least 30, or more amino acids. In some embodiments, the linker has about 1-15 amino acids. A peptide linker may be composed of various amino acid sequences. Preferably, a peptide linker will introduce some structural flexibility between components to be linked. Structural flexibility is achieved e.g., by having a peptide linker containing various glycine, serine, and/or proline residues, preferably at least 30%, more preferably at least 40%, and even more preferably at least 60% glycine, serine, and/or proline residues within the linker sequence. Irrespective of the specific sequence the peptide linker may preferably be immunologically inactive. In some embodiments, the linker comprises the amino acid sequence GGGGSGGGGS (SEQ ID NO:26). In some embodiments, the linker comprises a sequence corresponding to a cell-adhesion peptide, including, but not limited to collagen (types I, II, and III), fibronectin, and/or laminin. Without wishing to be bound by any particular theory, having linkers comprising cell-adhesion peptides facilitates the binding and immunological tolerance of the fusion proteins provided herein, for example in certain medical applications described herein. In some embodiments, the linker comprises a cell-adhesion peptide of collagen that comprises the sequence GFOGER (SEQ ID NO:27). In some embodiments, the linker comprises a cell-adhesion peptide of fibronectin that comprises one or more of the following sequences: RGD, PHSRN (SEQ ID NO:28), REDV (SEQ ID NO:29), and LDV. In some embodiments, the linker comprises a cell-adhesion peptide of laminin that comprises one or more of the following sequences: RGD, IKVAV (SEQ ID NO:30), YIGSR (SEQ ID NO:31), and PDSGR (SEQ ID NO:32). In some embodiments, the linker is a non-peptide linker, for example, a polyethylene glycol (PEG) moiety, a carbohydrate, or any other functional group capable of chemically joining subunits of the fusion proteins described herein.

Figures 5A, 5B:
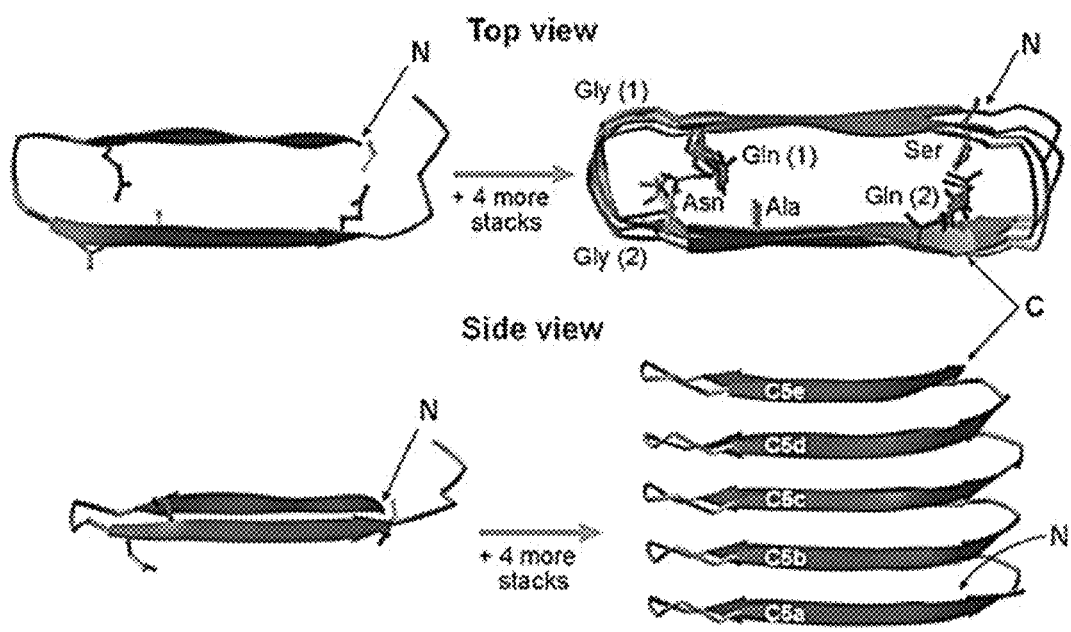
FIGS. 5A-5B depict the model structure and domains of CsgA.

In some embodiments, the fusion protein comprises a Mfp (e.g., those described herein) and an amyloid protein (e.g., those described herein), wherein the amyloid protein is fused to the N-terminus of the Mfp. In other embodiments, the amyloid protein is fused to the C-terminus of the Mfp. In still other embodiments, the Mfp is fused within the amyloid protein (e.g., the Mfp is flanked at both its N- and C-termini by aspects of the amyloid protein). For example, because CsgA contains five stacked strand-loop-strand motifs defined by conserved residues (referred to as repeating (R) domains 1-5; see FIG. 5), it is amenable for modification at multiple positions without interrupting its own self-assembling capability. Using rational design, the present invention provides 24 examples (Table 1) of fusion proteins comprising Mfp and CsgA, which vary in fusion positions and fusion domains, and are expected to self-assemble into fibril structures.

TABLE 1

| Numbers | Details of Construct | Note |
|---|---|---|
| 1-2 | CsgA (1-131)-LINKER-Mfp3(or Mfp5) | Fusion after C terminal (R5) |
| 3-4 | Mfp3(or Mfp5)-LINKER-CsgA | Fusion before N terminal (R1) |
| 5-6 | CsgA* (1-22)-LINKER-Mfp3(or Mfp5)-LINKER-CsgA* (23-131) | Fusion before R1 |
| 7-8 | CsgA* (31-22)-LINKER-Mfp3(or Mfp5)-LINKER-CsgA* (32-131) | Fusion within R1 |
| 9-10 | CsgA* (1-42)-LINKER1-Mfp3(or Mfp5)-LINKER-CsgA* (43-131) | Fusion between R1 and R2 |
| 11-12 | CsgA* (1-54)-LINKER-Mfp3(or Mfp5)-LINKER-CsgA* (55-131) | Fusion within R2 |
| 13-14 | CsgA* (1-65)-LINKER-Mfp3(or Mfp5)-LINKER-CsgA* (66-131) | Fusion between R2 and R3 |
| 15-16 | CsgA* (1-77)-LINKER-Mfp3(or Mfp5)-LINKER-CsgA* (78-131) | Fusion within R3 |

TABLE 1-continued

| Numbers | Details of Construct | Note |
| --- | --- | --- |
| 17-18 | CsgA* (1-87)-LINKER-Mfp3(or Mfp5)-LINKER-CsgA* (88-131) | Fusion between R3 and R4 |
| 19-20 | CsgA* (1-98)-LINKER-Mfp3(or Mfp5)-LINKER-CsgA* (99-131) | Fusion within R4 |
| 21-22 | CsgA* (1-110)-LINKER-Mfp3(or Mfp5)-LINKER-CsgA* (111-131) | Fusion between R4 and R5 |
| 23-24 | CsgA* (1-122)-LINKER-Mfp3(or Mfp5)-LINKER-CsgA* (123-131) | Fusion within R5 |

Numbers in parentheses indicate the residue numbers making up a particular portion of CsgA;
*indicates that CsgA is split by an intervening Mfp (e.g., Mfp3 or Mfp5) sequence.

In some embodiments, the fusion protein comprises Mfp5 and CsgA, wherein the C-terminus of Mfp5 is fused to the N-terminus of CsgA, e.g., Mfp5-CsgA. Representative sequences (amino acid: SEQ ID NO:9; nucleotide: SEQ ID NO:10) for Mfp5-CsgA are shown below.

```
Amino acid sequence for Mfp5-CsgA:
                                            (SEQ ID NO: 9)
MSSEEYKGGYYPGNTYHYHSGGSYHGSGYHGGYKGKYYGKAKKYYYKYKN

SGKYKYLKKARKYHRKGYKKYYGGGSSGGGGSGGGGSGVVPQYGGGGNHG

GGGNNSGPNSELNIYQYGGGNSALALQTDARNSDLTITQHGGGNGADVGQ

GSDDSSIDLTQRGFGNSATLDQWNGKNSEMTVKQFGGGNGAAVDQTASNS

SVNVTQVGFGNNATAHQY.
```

The underlined portion corresponds to a linker between Mfp5 and CsgA. In some embodiments, the sequence further comprises a poly-histidine tag, as described herein.

```
Nucleotide sequences of Mfp5-CsgA:
                                            (SEQ ID NO: 10)
ATGAGTTCTGAAGAATACAAAGGTGGTTATTACCCAGGCAATACTTACCA

CTATCATTCAGGTGGTAGTTATCACGGATCCGGCTATCATGGAGGATATA

AGGGAAAGTATTACGGAAAGGCAAAGAAATACTATTATAAATATAAAAAC

AGCGGAAAATACAAGTATCTGAAGAAAGCTAGAAAATACCATAGAAAGGG

TTACAAGAAGTATTATGGAGGTGGTAGCAGTGGCGGTGGCGGTAGCGGTG

GCGGTGGCAGTGGTGTTGTTCCTCAGTACGGCGGCGGCGGTAACCACGGT

GGTGGCGGTAATAATAGCGGCCCAAATTCTGAGCTGAACATTTACCAGTA

CGGTGGCGGTAACTCTGCACTTGCTCTGCAAACTGATGCCCGTAACTCTG

ACTTGACTATTACCCAGCATGGCGGCGGTAATGGTGCAGATGTTGGTCAG

GGCTCAGATGACAGCTCAATCGATCTGACCCAACGTGGCTTCGGTAACAG

CGCTACTCTTGATCAGTGGAACGGCAAAAATTCTGAAATGACGGTTAAAC

AGTTCGGTGGTGGCAACGGTGCTGCAGTTGACCAGACTGCATCTAACTCC

TCCGTCAACGTGACTCAGGTTGGCTTTGGTAACAACGCGACCGCTCATCA

GTACTAA.
```

In some embodiments, the sequence comprises a sequence encoding a poly-histidine tag 5' to the stop codon (e.g., TAA), such as ATCACCATCACCATCACCAT (SEQ ID NO:35).

In some embodiments, the fusion protein comprises Mfp3 and CsgA, wherein the C-terminus of CsgA is fused to the N-terminus of Mfp3, e.g., CsgA-Mfp3. Representative sequences (amino acid: SEQ ID NO:8; nucleotide: SEQ ID NO:11) for CsgA-Mfp3 are shown below.

```
                                            (SEQ ID NO: 8)
MGVVPQYGGGGNHGGGGNNSGPNSELNIYQYGGGNSALALQTDARNSDLT

ITQHGGGNGADVGQGSDDSSIDLTQRGFGNSATLDQWNGKNSEMTVKQFG

GGNGAAVDQTASNSSVNVTQVGFGNNATAHQYGGGGSGGGGSADYYGPKY

GPPRRYGGGNYNRYGRRYGGYKGWNNGWKRGRWGRKYY.
```

The underlined portion corresponds to a linker between CsgA and Mfp3. In some embodiments, the sequence further comprises a poly-histidine tag, as described herein.

```
Nucleotide sequences of CsgA-Mfp3:
                                            (SEQ ID NO: 11)
ATGGGTGTTGTTCCTCAGTACGGCGGCGGCGGTAACCACGGTGGTGGCGG

TAATAATAGCGGCCCAAATTCTGAGCTGAACATTTACCAGTACGGTGGCG

GTAACTCTGCACTTGCTCTGCAAACTGATGCCCGTAACTCTGACTTGACT

ATTACCCAGCATGGCGGCGGTAATGGTGCAGATGTTGGTCAGGGCTCAGA

TGACAGCTCAATCGATCTGACCCAACGTGGCTTCGGTAACAGCGCTACTC

TTGATCAGTGGAACGGCAAAAATTCTGAAATGACGGTTAAACAGTTCGGT

GGTGGCAACGGTGCTGCAGTTGACCAGACTGCATCTAACTCCTCCGTCAA

CGTGACTCAGGTTGGCTTTGGTAACAACGCGACCGCTCATCAGTACGGCG

GTGGCGGTAGCGGTGGCGGTGGCAGTGCTGATTATTATGGTCCAAAGTAT

GGTCCTCCAAGACGCTACGGTGGTGGCAACTACAATAGATATGGCAGACG

TTATGGCGGGTATAAAGGCTGGAACAATGGTTGGAAAAGAGGTCGATGGG

GACGAAAGTATTATTAA.
```

In some embodiments, the sequence comprises a sequence encoding a poly-histidine tag 5' to the stop codon (e.g., TAA), such as, e.g.,

```
                                            (SEQ ID NO: 34)
CAGTACGGTGGCGGTAACTCTGCACTTGCTCTGCAAACTG.
```

Figure 1B:
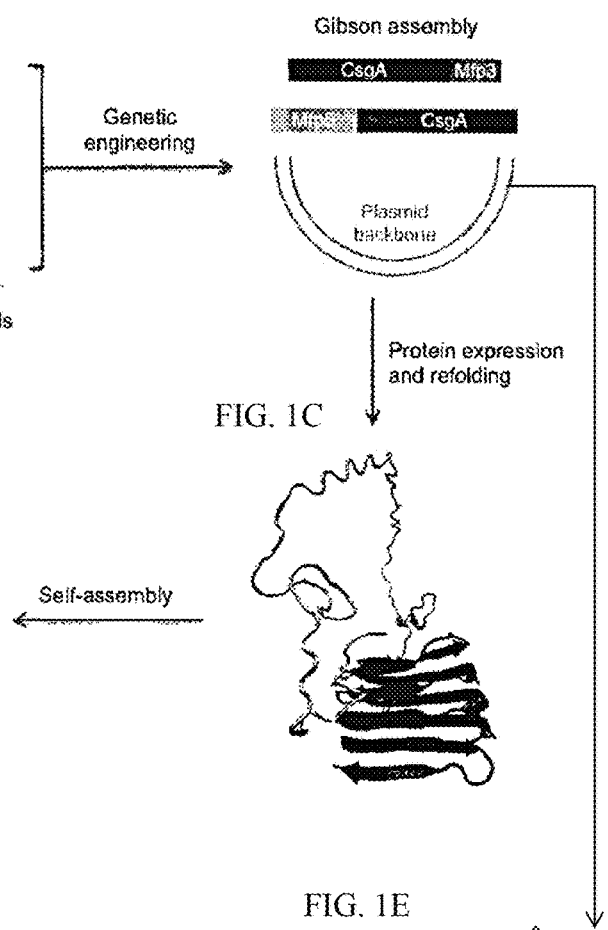
Figure 1D:
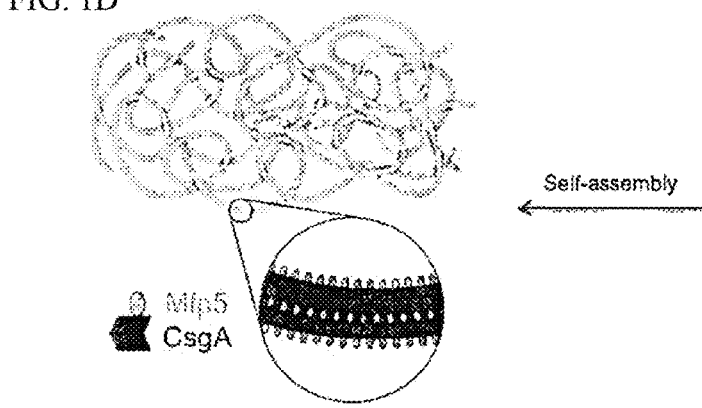

An illustration of the predicted structure of the fusion proteins (e.g., Mfp5-CsgA) is found in FIG. 1D. Because of the amyloidogenic feature, inventive fusion proteins have the capacity to self-assemble into large bundles of fibrils or hierarchical networks of filaments. Without wishing to be bound by any particular theory, is it believed that the CsgA domains are key to fiber self-assembling by fibril extension via self-polymerization and β-strand lamination via lateral stacking, while adhesive domains (e.g., Mfp3 and/or Mfp5)

are exposed on the fibril's surface. Enhanced underwater adhesion is believed to arise from the synergized behaviors from the two fusion domains including high fiber surface area and adhesive residues from Mfp domains.

In some embodiments, the fusion protein comprises a fragment of an amyloid protein, such as a fragment of CsgA. For example, the fragment is one that allows for the fusion protein to maintain amyloidgenic properties, e.g., allows for self-assembly. Thus, in some embodiments, a provided fusion protein may comprise a single stacked strand-loop-strand motif of CsgA (e.g., any one of R1, R2, R3, R4, or R5; see FIG. 5). In some embodiments, the fusion comprises one, two, three, four, or all five stacked strand-loop-strand motifs, in any combination or order. In some embodiments, the fusion protein comprises R1-R3, and does not contain R4 or R5.

Figure 16:
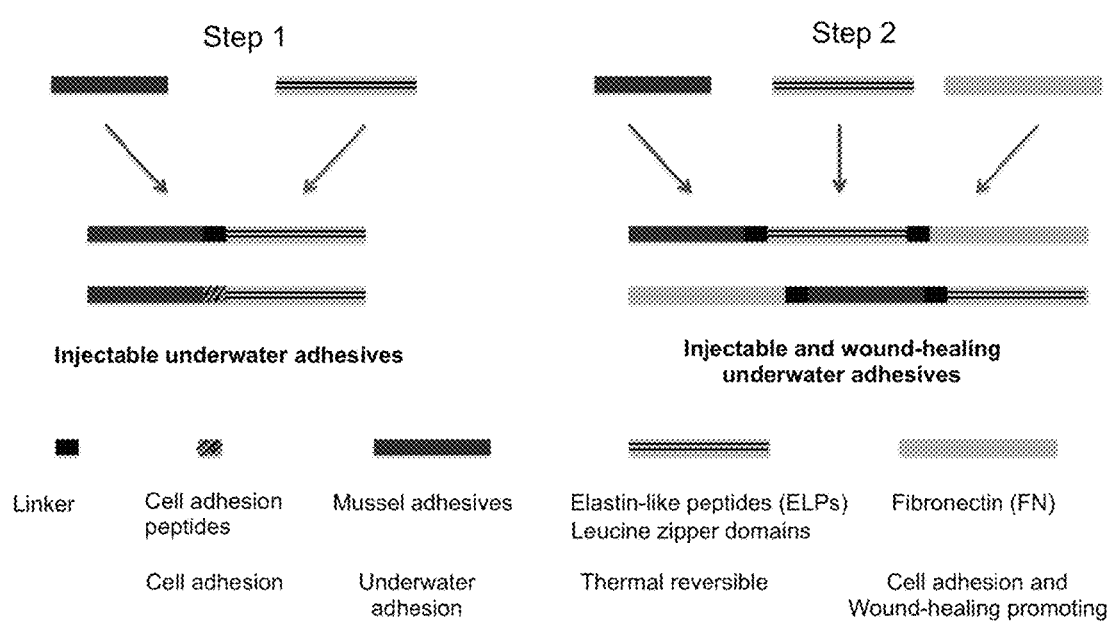
FIG. 16 depicts the use of a modular design to engineer multi-functional adhesive proteins. In this example, thermal-reversible functional domains are coupled to adhesive domains to construct injectable underwater adhesives useful in medical and marine applications (step 1). These proteins may be further modified in step 2) to include wound healing domains, such as fibronectin or cell-adhesion peptide domains.

In some embodiments, fusion proteins are provided comprising an adhesive protein and a thermal-reversible functional domain (See, e.g., FIG. 16). In some embodiments, the fusion protein further comprises an amyloid protein, as described herein. By "thermal-reversible," it is meant that the domain undergoes conformational changes in response to a change in temperature. In some embodiments, the thermal-reversible functional domain exists in an unstructured state at a certain temperature, but transitions to a structured state at a different (e.g., higher) temperature. In some embodiments, such a transition is referred to as a sol-gel transition, e.g., a transition from a liquid or solution state, to a solid or gel state. For certain biomedical applications described herein, a rapid sol-gel transition in the presence of tissue is required in order to minimize surgical delay. This can be accomplished by administration of an aqueous solution of a provided fusion protein that solidifies within seconds or tens of seconds in vivo. Such injectable wet medical adhesives capable of bonding or repairing tissues have the potential to replace stitches, staples, and screws typically used to repair damaged tissues. In some embodiments, the thermal-reversible functional domain comprises elastin-like peptides (ELPs), which are also referred to as elastin-like recombinamers (ELRs). Their inherent properties, such as biocompatibility, thermal sensitivity, and mechanical properties, make these recombinant peptide polymers suitable for numerous biomedical applications described herein. ELPs are typically 5 to 1500 amino acids in length and in some embodiments are made from the pentamer consensus sequence, VPGXG (SEQ ID NO:33), where X independently represents any amino acid. In some embodiments, the fusion protein comprises at least 2, at least 3, at least 4, at least 5, at least 10, at least 20, at least 40, at least 60, at least 80, at least 100, or at least 150 or more repeats of the sequence VPGXG (SEQ ID NO:33), where X independently represents any amino acid. ELPs exist in disordered conformations below their transition temperatures and form more ordered β-turns above their transition temperatures (See, e.g., Hassouneh et al., "Fusions of elastin-like polypeptides to pharmaceutical proteins." *Methods Enzymol.* 2012; 502:215-37; Asai et al., "Protein polymer hydrogels by in situ, rapid and reversible self-gelation." *Biomaterials.* 2012 July; 33(21):5451-8; the entire contents of each are hereby incorporated by reference). In some embodiments, provided thermal reversible fusion proteins undergo a sol-gel transition (e.g., from a liquid to a solid) at a temperature between about 20-60° C., between about 30-50° C., or between about 35-45° C. In some embodiments, a provided thermal reversible fusion protein forms a solid (e.g., hydrogel) at about (and above) 37° C. The adhesive protein component of the fusion protein can be any adhesive protein provided herein. In some embodiments, the adhesive protein is an Mfp. In some embodiments, the adhesive protein is Mfp3 or Mfp5.

In some embodiments, fusion proteins are provided that comprise an adhesive protein and one or more leucine zipper domains (See, e.g., FIG. 16). Leucine zippers form supercoils of two or more α-helical strands and are structural motifs commonly found in transcription factors. When fused with adhesive proteins described herein, they form reversible hydrogel biomaterials that undergo a sol-gel transition which is suitable for biomedical applications described herein. Methods of using leucine zippers to form hydrogel materials are known, and include those described by Wheeldon et al., "Bioelectrocatalytic hydrogels from electron-conducting metallopolypeptides coassembled with bifunctional enzymatic building blocks." *Proc Natl Acad Sci USA.* 2008 Oct. 7; 105(40):15275-80; and Banta et al., "Protein engineering in the development of functional hydrogels." *Annu Rev Biomed Eng.* 2010; 12:167-86, the entire contents of each are hereby incorporated by reference. In some embodiments, leucine zipper domains can be fused either at N or C-terminal of any provided fusion protein. In some embodiments, a leucine zipper domain comprises the sequence (or fragment thereof):

(SEQ ID NO: 36)
SGDLENEVAQLENEVRSLEDEAAELEQKVSRLKNEIEDLKAE

In some embodiments, any of the inventive fusion proteins provided herein further comprise functional domains that promote wound healing. For example, in certain embodiments, functional domains that promote wound healing include recombinant fragments of fibronectin (FN) (See, e.g., FIG. 16). FN is an extra-cellular matrix protein that can bind to many growth factors, such as vascular endothelial growth factor (VEGF), and also contains cell adhesion sites. In previous studies, a recombinant fibronectin fragment containing the seven to ten Type III repeats (FNIII7-10) was shown to enhance osteoblast adhesion strength and differentiation in vitro on modified surfaces, as well as titanium implant osseointegration in vivo when compared to RGD peptide surfaces (von der Mark et al., "Nanoscale engineering of biomimetic surfaces: cues from the extracellular matrix." *Cell and Tissue Research.* 2010; 339, 131-153; Shekaran & Garcia, et al., "Nanoscale engineering of extracellular matrix-mimetic bioadhesive surfaces and implants for tissue engineering." *Biochimica Et Biophysica Acta-General Subjects.* 2011; 1810, 350-360; the entire contents of each are hereby incorporated by reference). Thus, in some embodiments, fusion proteins are provided comprising an adhesive protein (as provided herein) and fibronectin, or a fragment thereof, e.g., RGD, PHSRN (SEQ ID NO:28), REDV (SEQ ID NO:29), and/or LDV. In some embodiments, the adhesive protein is Mfp3 or Mfp5, as described herein. In some embodiments, the functional domain of the fusion protein that promotes wound healing is histatin (or fragments thereof), and/or Epidermal Growth Factor (EGF) fragments (See, e.g., Schneider et al., "Self-assembling peptide nanofiber scaffolds accelerate wound healing." *PLoS One.* 2008; 3, e1410; Oudhoff et al., "Structure-activity analysis of histatin, a potent wound healing peptide from human saliva: cyclization of histatin potentiates molar activity 1000-fold." The *FASEB* Journal. 2009; 23, 3928-3935; Demidova-Rice et al., "Bioactive peptides derived from vascular endothelial cell extracellular matrices promote microvascular morphogenesis and wound healing in vitro."

Wound Repair and Regeneration. 2011; 19, 59-70; the entire contents of each are hereby incorporated by reference). In some embodiments, the functional domains that promote wound healing are cell-adhesion peptides described herein, for example. a cell-adhesion peptide of collagen that comprises the sequence GFOGER (SEQ ID NO:27); and/or a cell-adhesion peptide of laminin that comprises one or more of the following sequences: RGD, IKVAV (SEQ ID NO:30), YIGSR (SEQ ID NO:31), and PDSGR (SEQ ID NO:32). In some embodiments, an adhesive fusion protein is provided that does not comprise a wound healing domain as part of the fusion protein, but instead acts as a physical substrate which binds one or more wound healing peptide/proteins (e.g., those described herein).

In some embodiments, any of the inventive fusion proteins described herein may further include a purification tag, detectable label, or both. For example, the fusion protein may comprise a poly-histidine tag (e.g., a 6×His-tag) for purification purposes (e.g., nickel or cobalt affinity based purification; see Hochuli et al., *Nature Biotechnology* 1988, 6, 1321-1325). In some embodiments, the poly-histidine tag comprises 4, 5, 6, 7, 8, 9, or 10 histidines. In some embodiments, the poly-histidine tag comprises seven histidines. In some embodiments, the fusion protein may comprise a detectable label.

In some embodiments, the fusion proteins of the present invention (e.g., comprising an adhesive protein and an amyloid protein) are fused to another protein.

In some embodiments, the fusion proteins provided herein contain one or more amino acid substitutions as compared to their wild-type counterparts. For example, certain conservative amino acid substitutions are contemplated. Conservative amino acid substitutions are amino acid substitutions in which the substituted amino acid residue is of similar charge as the replaced residue and/or is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered conservative substitutions even if the residues are in different groups (e.g., replacement of phenylalanine with the smaller isoleucine).

Fusion proteins provided herein may be produced by any method known in the art. For example, the fusion proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* (4th ed., Cold Spring Harbor Laboratory Press, Cold Spring Harbor, N.Y. (2012)), the entire contents of which are incorporated herein by reference. The fusion proteins may be collected from borate buffers or acid buffers during preparation. In certain embodiments, the fusion proteins described herein comprises diol-borate bonds. In certain embodiments, the fusion proteins described herein have a molecular weight range from about 20,000 Da to about 30,000 Da. In certain embodiments, the fusion proteins described herein have a molecular weight range from about 20,200 Da to about 25,000 Da.

Provided herein are fibers comprising at least one type of amyloid protein, or a fragment thereof, and at least one type of an adhesive protein derived from a marine organism, or a fragment thereof. Any of the fusion proteins of the present invention can be co-assembled to form bundles of fibers and/or networks of filaments. In certain embodiments, the fibers comprise at least one type of fusion protein described herein. In certain embodiments, the fibers comprise only CsgA-Mfp3. In certain embodiments, the fibers comprise only Mfp5-CsgA.

In certain embodiments, the fibers comprise at least two types of fusion proteins described herein. In certain embodiments, the fibers have two types of fusion proteins present in a molar ratio of about 1:20 to 20:1. In certain embodiments, the fibers have two types of fusion proteins present in a molar ratio of about 1:15 to 15:1. In certain embodiments, the fibers have two types of fusion proteins present in a molar ratio of about 1:3 to 3:1. In certain embodiments, the fibers have two types of fusion proteins present in a molar ratio of about 1:1 to 1:1.

In certain embodiments, the fibers comprise two types of fusion proteins: CsgA-Mfp3 and Mfp5-CsgA. In certain embodiments, the fibers comprise CsgA-Mfp3 and Mfp5-CsgA present in a molar ratio of about 1:20 to 20:1 CsgA-Mfp3:Mfp5-CsgA. In certain embodiments, the fibers comprise CsgA-Mfp3 and Mfp5-CsgA present in a molar ratio of about 1:15 to 15:1 CsgA-Mfp3:Mfp5-CsgA. In certain embodiments, the fibers comprise CsgA-Mfp3 and Mfp5-CsgA present in a molar ratio of about 1:3 to 3:1 CsgA-Mfp3:Mfp5-CsgA. In certain embodiments, the fusion protein copolymer comprises CsgA-Mfp3 and Mfp5-CsgA in a molar ratio of about 1:1 CsgA-Mfp3:Mfp5-CsgA.

In certain embodiments, the fiber has a mean diameter that is about 3× to about 5× larger than the mean diameter of a CsgA only fiber. In certain embodiments, the fibers have a mean diameter of up to about 40 nm, about 50 nm, about 60 nm, about 70 nm, about 80 nm, about 90 nm, or about 100 nm. In certain embodiments, the fibers have a mean diameter from about 5 nm to about 100 nm, about 10 nm to about 80 nm, about 20 to about 50 nm, or about 20 nm to about 60 nm.

The adhesives described herein are rich in beta-sheet secondary structures. In certain embodiments, the adhesives described herein have an aromatic amino acid content ranging from about 8% to about 20%. In certain embodiments, the adhesives comprise DOPA residues. In certain embodiments, the adhesive comprises modification ("modified" version), in which some or all of the tyrosine residues are converted to DOPA residues by tyrosinase (e.g., mushroom tyrosinase). In certain embodiments, the percentage of tyrosines converted to DOPA is at least about 30%. In certain embodiments, the percentage of tyrosines converted to DOPA is at least about 40%. In certain embodiments, the percentage of tyrosines converted to DOPA is at least about 50%. In certain embodiments, the percentage of tyrosines converted to DOPA is at least about 60%. In certain embodiments, the percentage of tyrosines converted to DOPA is about 50% to about 100%. In certain embodiments, the percentage of tyrosines converted to DOPA is about 50% to about 85%. In certain embodiments, the percentage of tyrosines converted to DOPA is about 50% to about 70%. In certain embodiments, the percentage of tyrosines converted to DOPA is about 50% to about 60%. In certain embodiments, the adhesive does not comprise DOPA residues. In certain embodiments, the adhesives described herein do not comprise a modification of the tyrosines to DOPA ("unmodified" version).

In certain embodiments, the adhesives described herein have a fluorescent quantum yield that is about 2× to about 4× higher than a CsgA only adhesive. In certain embodiments, the adhesives described herein have a fluorescent quantum yield (Q (%)) that is at least about 2.0. In certain embodiments, the adhesives described herein have a fluorescent quantum yield that ranges from about 2.0 to about 10.0 or about 2.0 to about 5.0. The fluorescent quantum yield can be determined by various methods such as the Williams comparative method (Williams, A. T. R., Winfield, S. A. & Miller, J. N. Relative fluorescence quantum yields using a computer-controlled luminescence spectrometer. *Analyst* 108, 1067-1071 (1983). In certain embodiments, an adhesive prepared from an unmodified version of Mfp-CsgA has a fluorescence quantum yield of 4.2. In certain embodiments, an adhesive prepared from an unmodified version of CsgA-Mfp3 has a fluorescence quantum yield of 2.9. In certain embodiments, an adhesive prepared from an unmodified version of CsgA-Mfp3-Mfp-CsgA copolymer has a fluorescence quantum yield of 3.9. In certain embodiments, an adhesive prepared from a modified version of Mfp-CsgA has a fluorescence quantum yield of 1.9. In certain embodiments, an adhesive prepared from a modified version of CsgA-Mfp3 has a fluorescence quantum yield of 2.6. In certain embodiments, an adhesive prepared from a modified version of CsgA-Mfp3-Mfp-CsgA copolymer has a fluorescence quantum yield of 2.1.

The adhesives described herein can adhere strongly to a variety of surfaces such as inorganic, organic, ceramic, metal, and polymeric surfaces. In certain embodiments, the adhesives described herein have a normalized adhesion force (force/radius) of at least about 20 mN/m, about 30 mN/m, about 40 mN/m, about 50 mN/m, about 60 mN/m, about 70 mN/m, about 80 mN/m, about 90 mN/m, or about 100 mN/m on a silica surface, gold surface, or a polystyrene surface. In certain embodiments, the adhesives described herein have a normalized adhesion force (force/radius) of about 20 mN/m to about 250 nN/m on a silica surface, or about 20 mN/m to about 150 nN/m on a gold surface, or about 20 mN/m to about 125 nN/m on a polystyrene surface. The foregoing values are based on AFM measurements using either a silica, gold, or polystyrene AFM tip surface. In certain embodiments, the modified version of the adhesive has greater adhesion than the unmodified version of the adhesive. In certain embodiments, the adhesives described herein maintain the foregoing adhesion force values under acid, neutral, or basic conditions. In certain embodiments, the foregoing adhesion force values are maintained under acidic or neutral conditions such a pH less than about pH 7.5. In certain embodiments, the foregoing adhesion force values are maintained under basic conditions. In certain embodiments, the foregoing adhesion force values are maintained under basic conditions such as about pH 7.5 or higher. In certain embodiments, the foregoing adhesion force values are maintained under basic conditions such as about pH 10.0 or higher.

In certain embodiments, the adhesives described herein have an adhesion energy (Ead) of at least about 2 mJ/m$^2$, about 2.2 mJ/m$^2$, about 2.5 mJ/m$^2$, about 3 mJ/m$^2$, about 4 mJ/m$^2$, about 5 mJ/m$^2$, about 7 mJ/m$^2$, about 9 mJ/m$^2$, about 10 mJ/m$^2$, about 12 mJ/m$^2$, about 15 mJ/m$^2$, about 18 mJ/m$^2$, or about 20 mJ/m$^2$ on a silica surface, gold surface, or polystyrene surface. In certain embodiments, the adhesives described herein have an adhesion energy (Ead) of about 2.5 to about 25 mJ/m$^2$ on a silica surface, or about 2.5 to about 15 mJ/m$^2$ on a gold surface or on a polystyrene surface. In certain embodiments, the adhesives described herein have an adhesion energy (Ead) of about 5 to about 25 mJ/m$^2$, about 10 to about 25 mJ/m$^2$, about 15 to about 25 mJ/m$^2$ or about 18 to about 25 mJ/m$^2$ on a silica surface. In certain embodiments, adhesive is a fiber made from modified CsgA-Mfp3-Mfp-CsgA copolymer and has an adhesion energy (Ead) of about 5 to about 25 mJ/m$^2$, about 10 to about 25 mJ/m$^2$, about 15 to about 25 mJ/m$^2$, or about 18 to about 25 mJ/m$^2$ on a silica surface. The foregoing values are based on AFM measurements using either a silica, gold, or polystyrene AFM tip surface. In certain embodiments, the modified version of the adhesive has greater adhesion energy than the unmodified version of the adhesive. In certain embodiments, the adhesives described herein maintain the foregoing adhesion energy values under acid, neutral, or basic conditions. In certain embodiments, the foregoing adhesion energy values are maintained under acidic or neutral conditions such as pH 7.5 or less. In certain embodiments, the foregoing adhesion energy values are maintained under basic conditions. In certain embodiments, the foregoing adhesion energy values are maintained under basic conditions such as about pH 7.5 or higher. In certain embodiments, the foregoing adhesion force values are maintained under basic conditions such as about pH 10.0 or higher. In certain embodiments, a copolymer fiber, such as a fiber made from CsgA-Mfp3-Mfp-CsgA copolymer, has a normalized adhesion force of about 20 mN/m to about 250 nN/m and an adhesion energy (Ead) of about 8 to about 25 mJ/m$^2$ on on silica surfaces, gold surfaces, or polystyrene surfaces. In certain embodiments, the CsgA-Mfp3-Mfp-CsgA copolymer is a modified version and has a normalized adhesion force of about 20 mN/m to about 250 nN/m and an adhesion energy (Ead) of about 8 to about 25 mJ/m$^2$ on on silica surfaces, gold surfaces, or polystyrene surfaces.

Polynucleotide Encoding Inventive Fusion Proteins

In another embodiment of the invention, isolated polynucleotides encoding an inventive fusion protein are provided. For example, isolated polynucleotides encoding any of the fusion proteins described herein are provided, e.g., for recombinant expression and purification of adhesive fusion proteins. In some embodiments, an isolated polynucleotide comprises one or more sequences encoding an adhesive protein (e.g., a Mpf), an amyloid protein (e.g., CsgA), a peptide linker, and combinations thereof, as described herein. For example, an isolated polynucleotide may comprise one or more sequences that encode one or more amino acid sequences selected from SEQ ID NOs:1-9. In some embodiments, an isolated polynucleotide comprises a sequence encoding any of the fusion proteins as provided in Table 1.

In some embodiments, vectors encoding any of the fusion proteins described herein are provided, e.g., for recombinant expression and purification of adhesive fusion proteins. In some embodiments, the vector comprises or is engineered to include an isolated polynucleotide, e.g., those described herein. In some embodiments, the vector comprises one or more sequences encoding an adhesive protein (e.g., a Mpf), an amyloid protein (e.g., CsgA), a peptide linker, and combinations thereof, as described herein. For example, a vector may comprise one or more sequences that encode amino acid sequences selected from SEQ ID NOs: 1-9. In some embodiments, a vector comprises a sequence encoding any of the fusion proteins as provided in Table 1. Typically, the vector comprises a sequence encoding a provided fusion protein in frame and operably linked to a promoter, such that the fusion protein is expressed in a host cell. Methods for selecting and engineering vectors for expressing proteins (e.g., those provided herein), transforming cells, and expressing/purifying recombinant proteins are well known in the art, and are provided by, for example, Green and Sambrook, *Molecular Cloning: A Laboratory Manual* (4th ed., Cold Spring Harbor Laboratory Press, Cold Spring Harbor, N.Y. (2012)).

In some embodiments, cells are provided, e.g., for recombinant expression and purification of adhesive fusion proteins. The cells include any cell suitable for recombinant protein expression, for example, cells comprising a genetic construct expressing or capable of expressing a provided fusion protein (e.g., cells that have been transformed with one or more vectors described herein, or cells having genomic modifications, for example, those that express a fusion protein provided herein from an allele that has been incorporated in the cell's (e.g., host cell) genome). Methods for transforming cells, genetically modifying cells, and expressing genes and proteins from such cells are well known in the art, and include those provided by, for example, Green and Sambrook, *Molecular Cloning: A Laboratory Manual* (4th ed., Cold Spring Harbor Laboratory Press, Cold Spring Harbor, N.Y. (2012)) and Friedman and Rossi, *Gene Transfer: Delivery and Expression of DNA and RNA, A Laboratory Manual* (1st ed., Cold Spring Harbor Laboratory Press, Cold Spring Harbor, N.Y. (2006)).

Adhesive Compositions and Methods of Use

According to another embodiment of the invention, adhesive compositions comprising one or more adhesive fusion proteins or fibers thereof as described herein are provided. In one embodiment, medical adhesive compositions are provided. For example, because the fusion proteins and fibers thereof provided herein display strong adhesion in wet environments, and transition from an aqueous and injectable solution to a sticky fibril based plaque, they are particularly suited to medical applications. Such medical applications include, e.g., surgical or emergency treatment settings, for example, to close or help close an incision or wound. In some embodiments, a provided medical adhesive is useful as a sealant at an organ transplant or medical device implant interface, or to help set a broken or fractured bone. In some embodiments, an inventive medical adhesive is useful in orthopedic applications, e.g., as described herein. These applications have been investigated in vivo using mussel-inspired medical adhesives (e.g., PEG-catechol adhesives) in mice (Brubaker et al., Biological performance of mussel-inspired adhesive in extrahepatic islet transplantation. Biomaterials 31:420-27; 2010). This work demonstrated that mussel-inspired adhesives can be used in vivo, showing both tissue biocompatibility and integrity of the adhesive-tissue interface. In this study, rapid gelling mixtures of mussel-inspired adhesives were applied onto adipose tissue surfaces, where they formed adherent hydrogel coatings in situ. As described in the study, histological evaluation at time points up to 1 year after implantation showed minimal inflammatory cell infiltrate and little evidence of fibrotic capsule formation, indicating biocompatibility of the adhesive. Across each time points, the adhesive remained visible and present at the original deposition site, and the material-tissue interface remained intact. The surrounding adipose tissue remained healthy and well vascularized, and there was no evidence of nonspecific postsurgical adhesions. In another experiment, a more stringent test of biocompatibility consisted of transplanting mouse islets onto adipose and liver surfaces of diabetic mice using mussel-inspired adhesives (e.g., PEG-catechol hydrogel); the adhesive was designed to seal or bond the islets directly onto the tissue surface in a minimally invasive manner. The adhesive formed a hydrogel layer over the affixed islets, resulting in islet entrapment between the adhesive and tissue surface. In the study, blood glucose was used as a measure of islet graft performance and adhesive biocompatibility. Control mice and those transplanted with PEG-catechol adhesive (but no islet cells) showed no statistical difference in the mean number of days post-transplant after which normoglycemia was achieved. Histological analysis of the implant site revealed adhesive-immobilized islets to be well vascularized after several months in vivo and were actively secreting insulin. As another example, mussel-inspired adhesives have also been investigated as injectable surgical sealants for repair of gestational fetal membrane ruptures, which often occur during invasive diagnostic and therapeutic fetal surgical procedures (Bilic et al., Injectable candidate sealants for fetal membrane repair: bonding and toxicity in vitro. *Am. J. Obstet.* Gynecol. 2010; 202:85.e1-9). These studies indicate that adhesives inspired by bioadhesives found in nature are well suited for medical applications. Because the fusion protein adhesives of the present invention display superior adhesion energies compared to natural and mussel-inspired adhesives known in the art, as well as unexpected fluorescence properties, they represent a significant improvement in the field of medical adhesives.

In some embodiments, the medical adhesive composition of the present invention comprises one or more fusion protein adhesive or fibers thereof provided herein. For example, the medical adhesive composition comprises one or more the of the fusion proteins provided in Table 1 or fibers thereof. In some embodiments the medical adhesive composition comprises a fusion protein encoded by SEQ ID NO:8, SEQ ID NO:9, or both or fibers thereof. In some embodiments, the composition comprises a fusion protein comprising a functional domain, for example those that are thermal-reversible and/or promote wound healing, as described herein. In some embodiments, the medical adhesive composition comprises additional agents, for example, therapeutic agents. In some embodiments, the therapeutic agent promotes wound healing. For example, therapeutic agents contemplated by the present invention include, but are not limited to, various growth factors such as platelet-derived growth factor (PDGF), transforming growth factor alpha and beta (TGF-α, TGF-β), epidermal growth factor (EGF), hepatocyte growth factor (HGF), vascular endothelial growth factor (VEGF), fibroblast growth factor 1 and 2 (FGF-1, FGF-2), keratinocyte growth factor (KGF), and insulin-like growth factor 1 (IGF-1). In some embodiments, additional therapeutic agents include blood-clotting agents, for example, thrombin, fibrinogen, blood coagulation factor VIII, and combinations thereof. Thus, in some embodiments, the medical adhesive is used as a hemostatic material that both binds a wound and promotes clotting to prevent further loss of blood from the wound. Other agents include antibiotics or antimicrobials such as kanamycin, neomycin, polymyxin B, and bacitracin. In some aspects, other agents include components of the extracellular matrix (ECM) (e.g., glycosaminoglycans, proteoglycans, heparin sulfate, chondroitin sulfate, keratin sulfate, hyaluronic acid, collagen, elastin, fibronectin, laminin, etc.). Additional agents also include chitin, chitosan nanofibers, and gold and silver nanoparticles. In some embodiments, the medical adhesive composition is sterile, and thus intended for in vivo use. In some embodiments, the medical adhesive is a component of a pharmaceutical composition, as described herein.

In another embodiment, a method for bonding or repairing a tissue is provided. In some embodiments, the tissue to be repaired is a tissue having an incision or wound, for example, a tissue of a subject having undergone a surgical procedure, or a tissue of a subject having some trauma-induced wound. In some embodiments, the tissue is epithelial (e.g., skin), muscle, or nervous tissue. In some embodiments, the tissue is a connective tissue (e.g., loose connective tissue, collagenous fibers, elastic fibers, reticular fibers, adipose, cartilage, tendons, ligaments, etc.). In some embodiments, the tissue is bone. In some embodiments, the method involves contacting a tissue (e.g., a tissue in need thereof) with a medical adhesive composition, for example, those provided herein. Methods for applying medical adhesive compositions are known in the art, and include, for example, those described by Bruns and Worthington, *Using Tissue Adhesive for Wound Repair: A Practical Guide to Dermabond, Am. Fam. Physician.* 2000 Mar. 1; 61(5):1383-1388.

In another embodiment, adhesive compositions are provided, e.g., for forming underwater bonds, for example in marine settings. Because the provided fusion protein and fiber adhesives have strong adhesion energies under saline conditions, they are well-suited to applications involving bonding components underwater, including salt water. In some embodiments, the adhesive composition of the present invention comprises one or more fusion protein adhesives or copolymers provided herein. For example, the adhesive composition comprises one or more the of the fusion proteins provided in Table 1. In some embodiments the adhesive composition comprises a fusion protein encoded by SEQ ID NO:8, SEQ ID NO:9, or both. As discussed above, adhesives comprising two types of fusion proteins are referred to herein as copolymer or copolymer fibers. In some embodiments, the adhesive composition comprises additional agents, for example antioxidants, which are useful in preventing unwanted oxidation of the adhesive composition. Antioxidants include, but are not limited to, ascorbic acid, lipoic acid, uric acid, carotenes, polyphenols, and tocopherols.

Figure 15:
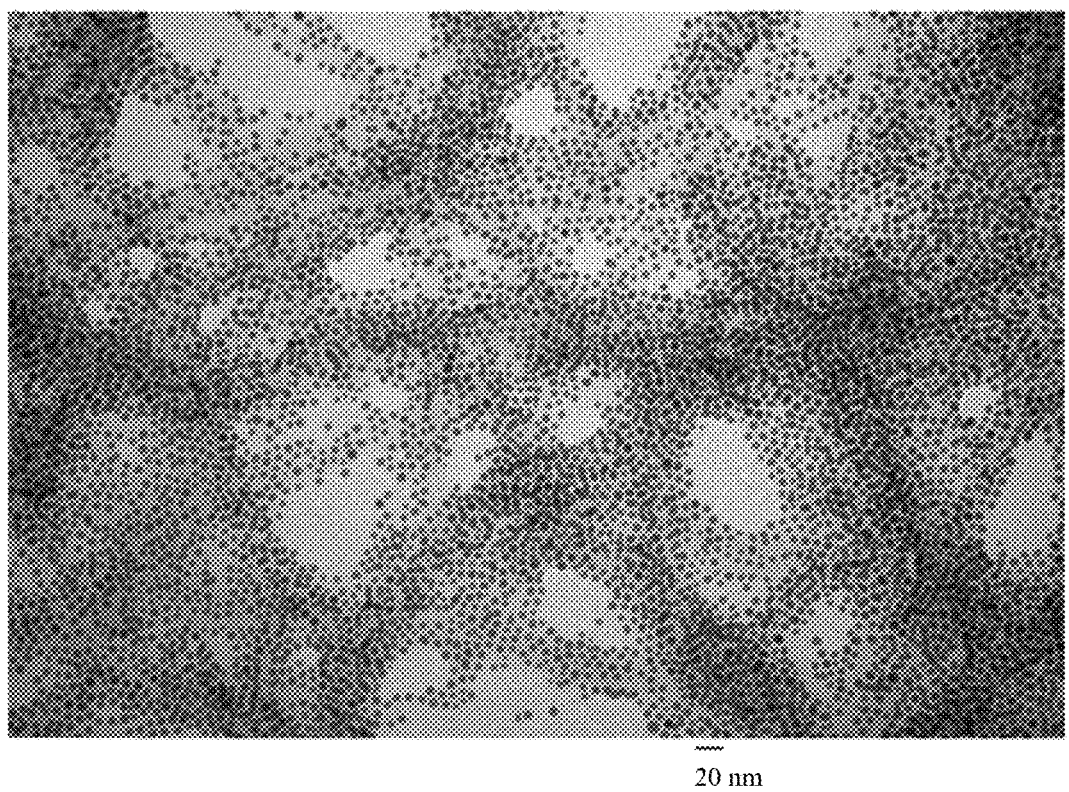
FIG. 15 is a photograph depicting gold nanoparticles bound to fibrils of Mfp-CsgA fusion protein. Droplet of Gold nanoparticles was incubated with CsgA-Mfp3 fibers in the presence of 0.487M NaCl, 80 mM imidazole, 0.2v/v % Tween for one hour, and then washed with 100 μL 1×PBS solution, and 100 μL 300 mM imidazole solution, followed by 200 μL deionized water three times, respectively. The samples were then deposited onto TEM grid for imaging.

In some embodiments, the adhesive composition is used as a template to bind gold and/or semiconductor particles/nanorods (See e.g., FIG. 15). In some embodiments, binding gold and/or semiconductor particles/nanorods is useful for generating e.g., colloidal superparticles used in applications involving polarized light emitting diodes and electrooptical modulators (See, e.g., Wang et al., "Self-Assembled Colloidal Superparticles from Nanorods." *Science.* 2012; Vol. 338 no. 6105 pp. 358-363; Yu et al., "Forming biocompatible and nonaggregated nanocrystals in water using amphiphilic polymers." *J. Am.* Chem. Soc. 2007 Mar. 14; 129(10):2871-9; and Cheng et al., *Nat. Mater.* 2009 June; 8(6):519-25; the entire contents of each are hereby incorporated by reference).

In some embodiments, the adhesive fibers are used to produce fiber-reinforced composites. A fiber-reinforced composite (FRC) is a composite building material that generally consists of three components: (i) the fibers as the discontinuous or dispersed phase, (ii) the matrix as the continuous phase, and (iii) the fine interphase region, also known as the interface. In some embodiments, the adhesive composition is used in the matrix phase, which binds the fibers to form lamina making up the FRC. Fibers can be any suitable fiber for producing FRC, including, but not limited to glass fibers, carbon (graphite) fibers, Kevlar fibers, extended chain polyethylene fibers, boron fibers, ceramic fibers, and natural fibers from e.g., cellulosic waste streams. Methods of making FRC are known, and include those described by P. K. Mallick, *Fiber-Reinforced Composites: Materials, Manufacturing, and Design.* Third Edition, CRC Press, 2004; the entire contents of which are hereby incorporated by reference.

In some embodiments, methods for bonding materials underwater are provided. In some embodiments, the methods involve contacting materials (e.g., materials to be bonded) with an adhesive composition provided herein. In some embodiments, the materials to be bonded or joined comprise one or more aspects of a watercraft, for example, aspects or components on the underside of a boat or vessel. In some embodiments, the materials to be bonded, joined, or plugged include pools, pool liners, pool toys, plumbing, and aquariums.

In some embodiments, compositions comprising one or more of the fusion protein or fiber adhesives of the present invention are useful for promoting cell and/or tissue attachment to surfaces, for example with in vitro cell culture. In some embodiments, such compositions are applied to a surface (e.g., a plastic, glass, metal, or polymer-based cell culture dish). Subsequent to applying the composition comprising one or more fusion proteins, the surface is contacted with cells and/or tissue, and because of the presence of the adhesive fusion proteins, the cells become attached to the cell culture surface. Methods for applying compositions for promoting cell/tissue attachment are known in the art, and include, for example, those described in the manual for the cell and tissue adhesive BD Cell-Tak™ (BD Biosciences, San Jose, Calif.).

In some embodiments, the adhesive compositions provided herein are treated with a chemical or enzyme prior to use. As discussed above, for example, the compositions may be treated with the enzyme tyrosinase (See Materials and Methods of Example) to convert the tyrosine residues in the Mfp component of the fusion protein into DOPA, thereby activating and/or increasing the adhesive properties of the Mfp component of the fusion protein.

Kits

According to another embodiment, kits comprising one or more of the compositions (e.g., those comprising a provided fusion protein or composition for producing same). A "kit," as used herein, typically defines a package or an assembly including one or more of the compositions of the invention, and/or other compositions associated with the invention, for example, as described herein. The kit may include isolated or purified fusion protein adhesives, polynucleotides, and/or vectors encoding provided fusion proteins, cells expressing or capable of expressing provided fusion proteins, and combinations thereof. Each of the compositions of the kit may be provided in liquid form (e.g., in solution), in solid form (e.g., a dried powder), or may be in a suspension, such as a frozen suspension of cells. In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, administering, modifying, assembling, storing, packaging, preparing, mixing, diluting, and/or preserving the compositions components for a particular use, for example, to a sample and/or a subject. In some embodiments, the kit includes a material or surface to which an inventive fusion protein or adhesive is applied. For example, for certain orthopedic application-based kits, the kit may further include one or more components for joint replacement. For certain marine or plumbing based applications, the kit may further include a pipe or fitting to which an inventive adhesive is applied.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, activation, mixing, diluting, preserving, administering, assembly, storage, packaging, and/or preparation of the composition and/or other compositions associated with the kit. In some cases, the instructions may also include instructions for the delivery and/or administration of the compositions, for example, for a particular use, e.g., to a material and/or a subject.

vector and appropriate PCR products were mixed and incubated with Gibson Assembly Master Mix (New England Biolabs, Ipswich, Mass.) at 50° C. for 1 hour, then transformed into DH5a E. coli cells. PCRs were carried out with primer oligos (Supplementary Table 1) from Integrated DNA Technologies and Kapa Hifi Hotstart from Kapa Biosystems (Woburn, Mass.). A Bio-Rad S1000 Thermal Cycler with Dual 48/48 Fast Reaction Modules (Bio-Rad) was used to perform PCRs, ligations and Gibson Assembly. Gel extractions were carried out with QIAquick Gel Extraction Kits (Qiagen). All constructs were sequence verified by Genewiz (Cambridge, Mass.).

SUPPLEMENTARY TABLE 1

Primers for constructing the genetic fusions in this study.

| Primer sequences | Template | Construct |
|---|---|---|
| Forward: (SEQ ID NO: 37) TTTAACTTTAAGAAGGAGATATACCATGGGTGTTGTTCCTCAG | pET-11d/CsgA | CsgA-Mfp3 |
| Reverse: (SEQ ID NO: 38) ACTGCCACCGCCACCGCTACCGCCACCGCCGTACTGATGAGCGGTCG | | |
| Forward: (SEQ ID NO: 39) GGCGGTGGCGGTAGCGGTGGCGGTGGCAGTGCTGATTATTATGGTCCAAAGTA | Mfp3 | |
| Reverse: (SEQ ID NO: 40) TTTCGGGCTTTGTTAGCAGCCGGATCCTTAATGGTGATGGTGATGGTGATGATAATACTTTCGTCCCCATCG | | |
| Forward: (SEQ ID NO: 41) TTTAACTTTAAGAAGGAGATATACCATGAGTTCTGAAGAATACAAAGGTG | Mfp5 | Mfp5-CsgA |
| Reverse: (SEQ ID NO: 42) GGAACAACACCACTGCCACCGCCACCGCTACCGCCACCGCCACTGCTACCACCTCCA | | |
| Forward: (SEQ ID NO: 43) GGTGGCGGTGGCAGTGGTGTTGTTCCTCAGTACG | pET-11d/CsgA | |
| Reverse: (SEQ ID NO: 44) GCTTCCTTTCGGGCTTT | | |

EXAMPLES

In order that the invention described herein may be more fully understood, the following examples are set forth. It should be understood that these examples are for illustrative purposes only and are not to be construed as limiting this invention in any manner.

Materials and Methods

Plasmid construction. Mfp constructs and CsgA/Mfp fusion constructs were created using basic molecular cloning techniques and isothermal Gibson assembly. Recombinant genes combining CsgA, mussel foot protein-3 or -5 (from *Mytilus galloprovincialis*) with appended C-terminal (His)6 tags were constructed using isothermal Gibson assembly and fusioned into plasmid pET-11d with a T7 promotor. PCRs were carried out with primer oligos from Integrated DNA Technologies (Coralville, Iowa) and Kapa Hifi Hotstart from Kapa Biosystems (Woburn, Mass.). The pET-11d vector was cleaved at BamHI and NcoI sites. The genes for csgA, mfp3, and mfp5 were separately amplified by PCR with introduced compatible overhangs for Gibson assembly. The cleaved Protein purification, characterization and post-modification with enzyme tyrosinase. The recombinant genes were individually expressed in the NEB C3016 strain and the recombinant proteins were purified under combined denaturing/nondenaturing conditions by cobalt-affinity chromatography. Post-modification via enzyme tyrosinase was carried out under nondenaturing conditions before eluting proteins from the cobalt resin column. The purified proteins were confirmed with SDS-PAGE and Western Blot. The recombinant genes including pET11d/CsgA, pET11D/CsgA-Mfp3 and pET11d/Mfp5-CsgA were transformed in the NEB C3016 E. coli strains. The strains were grown to OD600 0.9 in LB broth containing 50 mg/mL ampicillin at 37° C. The expression of proteins was induced with 0.5 mM IPTG and induction proceeded at 37° C. for 1 h. Cells were collected by centrifugation, and the pellets were stored at −80° C. The cells were resuspended and lysed by extraction solution (8 M GdnHCl, 50 mM K2HPO4/KH2P04, pH 7.2). A total of 50 mL of extraction solution was used for cell pellets from a 1500 mL culture. The lysate was incubated at 4° C. for 24 h. The insoluble portion of the lysate was removed by centrifuging at 10,000 g, and the supernatant was incubated with 6 mL Tylon cobalt resin (Clontech) for 2 h at room temperature. Protein purification was carried out under combined denaturing/non-denaturing conditions by cobalt-affinity chromatography. In vitro post-translational modification by tyrosinase (Sigma) was carried out under non-denaturing conditions before eluting proteins from the cobalt resin column. Beads that bound His-tagged CsgA, CsgA-Mfp3 and Mfp5-CsgA were loaded on the column, and lysis supernatant passed through the column. GdnHCl was washed away by 12 mL potassium phosphate buffer (50 mM K2HPO4/KH4P04, pH 7.2). Washing buffers with 40 mM imidazole and 50 mM potassium phosphate buffer (pH 7.2) were passed through the column to remove contaminated proteins before post-modification. Post-modification by enzyme tyrosinase (Sigma, mushroom tyrosinase) was carried out following a typical protocol reported in literature before[37]. Specifically, after removing imidazole with 50 mM K4HP04/KH2P04 (pH 7.2), 4 mL 0.5 mg/mL mushroom tyrosinase solution (20 mM sodium borate, 100 mM PBS, ascorbic acid 100 mM, pH=7.0) was added and seated on a shaker for 2h at room temperature. Finally, after washing with 50 mM K2HP04/KH2P04 (pH 7.2) twice to remove tyrosinase, modified proteins were eluted from the column by 0.3 M imidazole and 50 mM potassium phosphate buffer (pH 7.2). The purified proteins were then confirmed with SDS/PAGE and Western Blot, or further dialyzed against PBS solution (pH=5.0) for 2 days for further characterization. To collect proteins with higher purity for further characterization, the eluted proteins were either dialyzed against PBS solutions (pH=5.0 or 2.5) for 2 days or were incubated at 4° C. under acidic conditions for 3 days to promote the formation of amyloid fibers, followed by redissolving in hexafluoro-2-propanol (HFIP) solvent. To compare unmodified and modified proteins, we also purified proteins without postmodification. In this case, the washing steps described above for removing tyrosinase were not included in corresponding purification procedures. Purified proteins were assayed with SDS/PAGE, Western blotting, matrix-assisted laser desorption ionization (MALDI)—time-of-flight (TOF) mass spectrometry and amino acid analysis (AAA). The general amyloid features of all adhesive fibers were detected with a Congo Red (CR) assay. Dopa residues in modified proteins were qualitatively detected by Nitro Blue Tetrazolium (NBT) staining and quantitatively analysed with acid-borate difference spectrum (ABDS) analysis, supported by amino acid analysis (AAA). Kinetics of amyloid fiber formation was assessed with a Thioflavin T (ThT) assay using a BioTek Synergy H1 Microplate Reader (with BioTek GEN5 software) set to 438 nm excitation and 495 nm emission with a 475-nm cutoff.

SDS/PAGE and Western Blot SDS/PAGE. Small amount of washing solutions and elutions collected during purification process were used for SDS/PAGE. Samples were electrophoresed on a 12% SDS-polyacrylamide gel and stained with commassie blue following the standard staining protocols. After destaining with destaining solutions, the gels were imaged using the Bio-Rad ChemIDoc™ MP system.

Western Blot. Samples were electrophoresed on a 12% SDS-polyacrylamide gel and blotted onto polyvinylidene difluoride membrane using iblot (Invitrogen). Western blots were probed by anti-his polyclonal antibody and was used at a dilution of 1:10,000. The secondary antibody was anti-rabbit antibodies conjugated to horseradish peroxidase (Sigma) and was used at a dilution of 1:5,000. The blots were developed using the Pierce SuperSignal detection system and imaged using Bio-Rad ChemIDoc™ MP system.

Preparation of Adhesive Fibers

Based on initial concentrations determined by the Pierce BCA Protein Assay, purified monomer proteins dissolved in phosphate solutions (pH=7.2) were adjusted to slightly acidic conditions (pH=5.0), with final molar concentrations of 30 µM. Protein solutions sealed in tubes were stored in a 4° C. fridge overnight or for several days before characterizing their properties. To prepare copolymer fibers containing two monomer proteins (CsgA-Mfp3 vs Mfp5-CsgA) with different molar ratios, we incubated the two monomers at fixed molar concentration ratios of 3:7, 5:5 and 7:3, respectively, with a total monomer protein concentration of 30 µM.

Preparation of Adhesive Proteins/Hexafluoro-2-propanol (HFIP) Solutions for MALDI-TOF Eluted protein solutions were mixed with 1/5 volume of 5% (v/v) acetic acid concentration to prevent auto-oxidation and then incubated at 4° C. for 3 days to promote the formation of amyloid fibers. The amyloid aggregates were centrifuged at 12,000 rpm and then resuspended in 1% acetic acid (three times) to remove contaminated proteins or small molecules. The amyloid aggregates were collected by carefully removing the upper solutions and then resuspended in 2 mL of HFIP to depolymerize the amyloid aggregates into monomer proteins. For modified samples, the above solutions were diluted either in 100 mM hydrochloride acid solution or 100 mM borate buffer solution to protect the Dopa residues from auto-oxidation. Droplets of monomer protein solutions were then directly used for MALDI-TOF analysis.

MALDI-TOF Mass Spectroscopy Analysis of Unmodified and Modified Adhesive Proteins Protein samples in HFIP (approximately 10 pmol) were briefly speed-vacuum-dried and reconstituted in sinapinic acid matrix (10 mg/mL in 70% MeCN/0.1% TFA) and analyzed on a Bruker model MicroFlex MALDI-TOF instrument using standard linear mode, positive polarity protein MW method parameters, and laser power.

Congo Red (CR) and Nitro Blue Tetrazolium (NBT) assays. Dopa-containing proteins can be specifically stained by nitroblue tetrazolium (NBT) and glycinate solutions because they can catalyze redox-cycling reactions at an alkaline pH[9]. The NBT assay was thus used to confirm the successful post-translational modification of tyrosine into Dopa in modified proteins. In parallel, Congo red (CR) staining was used as an amyloid detection assay to confirm the general amyloid features for both unmodified and modified proteins. For Nitro Blue Tetrazolium Staining, 60 µL of 50 µg/mL adhesive protein samples were spotted onto Protran BA83 nitrocellulose membranes (Whatman) with a dot blot manifold (Schleicher & Schuell Minifold-I Dot-Blot System). The membranes spotted with protein solutions were incubated in 20 mL freshly made 0.6 mg/mL NBT solution in 2 M potassium glycinate buffer (pH=10.0) at room temperature in the dark (covered with aluminum foil) for 45 mins. The membranes were washed with 10 mL 0.16 M sodium borate solution twice and soaked in another 20 mL sodium borate solution overnight. Imaging of the stained membranes was carried out with a scanner. For Congo Red Staining, 60 µL of 50 µg/mL adhesive protein samples were spotted onto Protran BA83 nitrocellulose membranes (Whatman) with a dot blot manifold (Schleicher & Schuell Minifold-I Dot-Blot System). The membranes spotted with protein solutions were immersed in 20 mL of 0.0025 (m/v %) Congo red solution at room temperature for 1 hour. The membranes were then taken out and washed with copious amounts of deionized water for 3 times, and incubated in deionized water overnight. The stained membranes were imaged with a scanner.

Acid-borate Difference Spectrum for Quantitative Analysis of Dopa in Modified Adhesive Proteins Acid-borate difference spectrum analysis was used to quantitatively assess the amount of Dopa residues in modified adhesive proteins following the classic method reported by Waite et al. At least 3 repeats were carried out for each adhesive protein. Brief descriptions of the mechanism, special sample preparation, experimental procedures, and calculations are presented below.

Mechanism.

Dopa absorbs maximally in aqueous acid at about 280 nm. At pH 7-10 in the presence of borate, this maximum is shifted to higher wavelengths (286-287 nm) due to the formation of a diol-borate complex with a concomitant increase in absorptivity. This diol-borate complex is unique as borate forms no complex with the other UV-absorbing amino acids, phenylalanine, tyrosine, or tryptophan. The acid-borate difference spectrum of Dopa-containing samples has a concentration-dependent maximum absorptivity at $\lambda$max ~292-294 nm, thus enabling quantitative analysis of Dopa residues in the samples. This approach, however, requires Dopa-containing proteins to be soluble in both buffers.

Sample preparation. Modified adhesive proteins in soluble format were prepared as follows: concentrated adhesive proteins in HFIP solutions were diluted 10 times in slightly acidified solutions. The concentration of these solutions was then quickly measured with a BCA assay. The protein solutions were then equally divided into two parts, and each part was diluted 1:4 in 100 mM HCl buffer or 100 mM sodium tetraborate (pH=8.0). These solutions were labeled as "adhesive protein in acid buffer" or "adhesive protein in borate buffer".

Figure 23A:
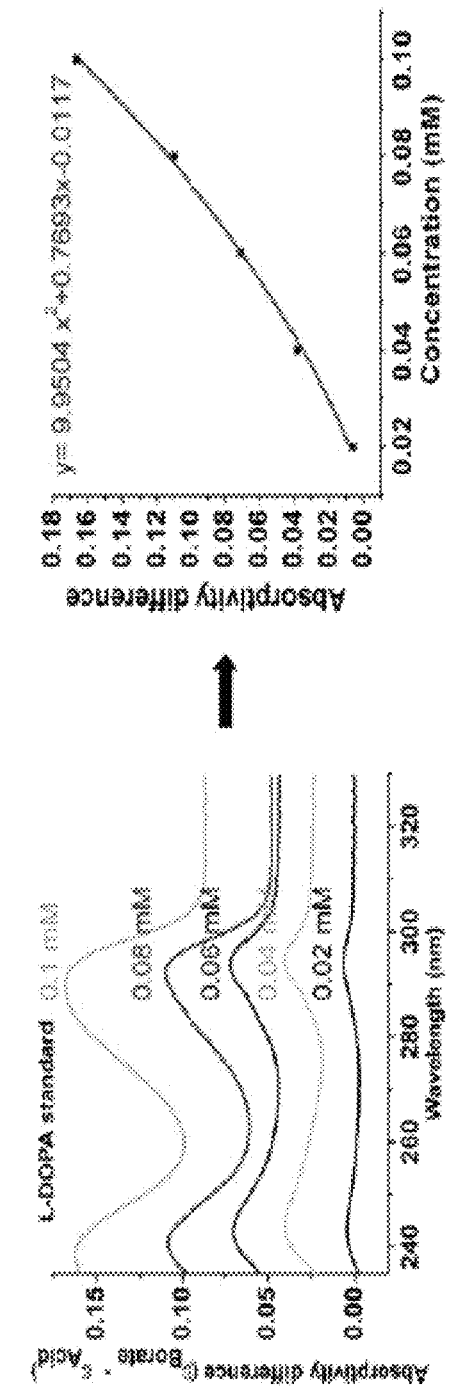
FIGS. 23A-23C show acid-borate difference spectra (ABDS) for quantitative analysis of Dopa amounts in modified adhesive proteins.
Figure 23C:
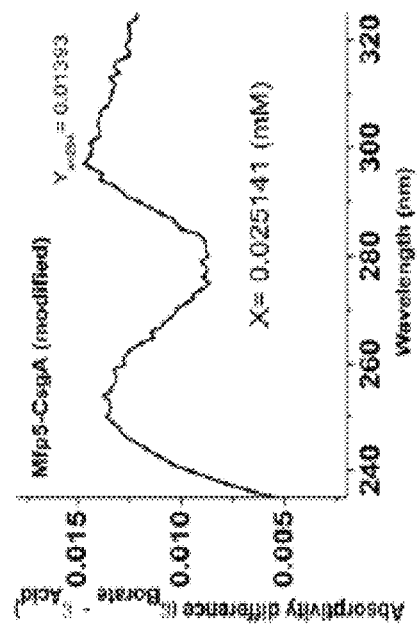
Figure 23B:
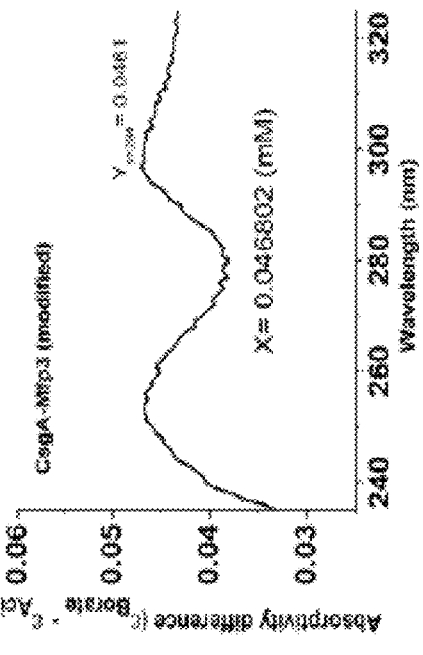

Experimental procedures. 40, 80, 120, 1600, and 200 µL of the 1.0 mM L-Dopa standard solution (freshly prepared by dissolving 197.2 mg of L-Dopa (Sigma) in 1 liter of distilled water acidified with 1 mL of concentrated HCl) were dispensed into two sets of five labelled tubes for the acid and the borate series. The final volume of each tube was adjusted to exactly 2 mL with 0.1 M HCl for the acid series or 0.1 M sodium tetraborate for the borate series. At 292-294 nm, zero absorbance was set by adjusting the slit width with the first acid-Dopa sample in the light path. Then, Ultraviolet-Visible (UV-Vis) absorption spectra for the same concentration of Dopa in borate buffer was recorded at room temperature with a CARY-6000i spectrophotometer. We carried out repeats of this protocol for the Dopa standards with different concentrations and for the adhesive proteins in acid and borate buffers as well (FIGS. 23b and 23c). We determined the Dopa content of samples from the standard curve (FIG. 23a): $\varepsilon=\Delta A/C*L$, where $\Delta A$ is the absorbance difference, C is the Dopa concentration in moles per liter, and L is the cuvette light path (1 cm).

Calculations for Dopa quantification based on the acid-borate spectrum for modified CsgAMfp3 (FIG. 23b) and modified Mfp5-CsgA (FIG. 23c):

Step 1. Based on the BCA assay, we obtained protein concentrations for both CsgAMfp3 (modified) and Mfp5-CsgA (modified) solutions:

$$C_{(CsgA-Mfp3(modified))}=0.409035\pm0.043 \text{ (mg/mL)};$$

$$C_{(Mfp5-CsgA(modified))}=0.1751\pm0.027 \text{ (mg/mL)};$$

For unmodified proteins, the theoretical molar concentration of total tyrosine in each proteins is equal to:

$$M_{(tyrosine\ in\ CsgA-Mfp3(unmodified))} = 14 * C_{(CsgA-Mfp3(unmodified))} / MW_{(CsgA-Mfp3(unmodified))}$$
$$= 14 * 409.035 * 10^{-3} / 20385.6$$
$$= 0.28091 \pm 0.0295 \text{ (mM)}$$

(Note: theoretically, each CsgA-Mfp3 molecule has 14 tyrosines)

$$M_{(tyrosine\ in\ Mfp5-CsgA(unmodified))} = 24 * C_{(Mfp5-CsgA(unmodified))} / MW_{(Mfp5-CsgA(unmodified))}$$
$$= 24 * 175.1 * 10^{-3} / 23539.1$$
$$= 0.17853 \pm 0.02753 \text{ (mM)}$$

(Note: theoretically, each Mfp5-CsgA molecule has 24 tyrosine residues)

Step 2. The above solutions were mixed with 3 volumes of acid or borate buffer solutions (1:4 sample dilution), and then were used for acid-borate difference spectrum analysis.

Based on the acid-borate difference spectrum for both CsgA-Mfp3 (modified) and Mfp5-CsgA (modified) solutions (FIG. 23), we derived the measured Dopa concentrations for the two proteins:

$$M_{(Dopa\ in\ CsgA-Mfp3(modified))}=0.046802 \text{ (mM)};$$

$$M_{(Dopa\ in\ Mfp5-CsgA(modified))}=0.025141 \text{ (mM)};$$

Since the solutions assayed were 4 times diluted from the original solutions, we thus obtained the conversion percentage of tyrosine into Dopa as follows:

$$\text{Conversion percentage of } Dopa_{(CsgA-Mfp3(modified))}(\%) = 0.046802/$$
$$((1/4)*$$
$$0.28091)*$$
$$100\%$$
$$= 66.6\%$$

$$\text{Conversion percentage of } Dopa_{(Mfp5-CsgA(modified))}(\%) = 0.025141/$$
$$((1/4)*$$
$$0.17853)*$$
$$100\%$$
$$= 56.3\%$$

Step 3. Following the same protocol, we carried out three replicate tests for each sample, and we obtained the mean conversion percentage of Dopa for each sample as follows:

Mean conversion percentage of $Dopa_{(CsgA-Mfp3(modified))}(\%)=64.8\pm3.7\%$

Mean conversion percentage of $Dopa_{(Mfp5-CsgA(modified))}(\%)=56.0\pm4.1\%$

Note: the above data are presented in FIG. 18d.

Amino acid analysis (AAA). AAA was used to confirm the amino acid content of the adhesive proteins and as an alternative assay to quantitatively assess Dopa amounts in adhesive proteins. Adhesive proteins in HFIP solutions (slightly acidified with dilute hydrochloride acid) were used for AAA. Hydrolysis and pre-column derivatization of samples were performed in a Waters Pico Tag workstation. Analysis of free and hydrolysate amino acids were performed in an Alliance HPLC from Waters. Data were recorded by the HPLC machine and analysed with Amino Acid Analysis Software afterwards. All the experiments and data analysis relevant to AAA were performed in the Molecular Biology Core Facilities (MBCF) proteomics core at the Dana Farber Cancer Institute (North Campus). For each protein, at least 3 replicates were carried out for AAA, with all reports passing the internal standards within tolerance. These results confirmed that the analysed samples were identical to the desired adhesive proteins with the correct amounts of amino acids. To assess the elution time of Dopa residues in modified proteins, we ran the hydrolysed adhesive protein samples along with additional L-Dopa control residues. Based on two runs of Dopa standard samples, we found that Dopa residues eluted with IBA (internal standard), with enormous peaks resulting when the same volume was used for all samples. Since only Dopa residues overlapped with peaks of IBA and tyrosine residues did not, and significant decreases in tyrosine residues were found only in modified proteins (compared with very slight changes in unmodified proteins), we, determined that it was reasonable to calculate the number of Dopa residues based on the following equations:

Number of Dopa in one modified CsgA-Mfp3 molecule=(14−Number of tyrosines in modified CsgA-Mfp3);

Number of Dopa in one modified Mfp5-CsgA molecule=(24−Number of tyrosines in modified Mfp5-CsgA).

Note: 14 and 24 are the total number of tyrosine residues in a single CsgA-Mfp3 (unmodified) and Mfp5-CsgA (unmodified) protein, respectively.

Three replicate HPLC runs were performed for each sample. Based on the three runs, we obtained the mean number of Dopa residues in each molecule as follows:

The mean number of DOPA residues$_{(CsgA-Mfp3(modified))}$=7.3±1.3

The mean number of DOPA residues$_{(Mfp5-CsgA(modified))}$(%)=14.7±1.6

Thus, we have:

Mean conversion percentage of Dopa$_{(CsgA-Mfp3(modified))}$(%)=52.1±9.3%

Mean conversion percentage of Dopa$_{(Mfp5-CsgA(modified))}$(%)=61.3±6.7%

Note: the above data are presented in FIG. 18d.

Circular Dichroism (CD)

10 µM Eluted Proteins were dialyzed against 50 mM KPi, pH=5.0 solution for 3 days, the dialyzed protein at 0.10 mg/ml concentration was assayed in an Aviv 62 DS model circular dichroism spectrometer from 190 to 260 nm in a quartz cell with a I-mm path length at 25° C.

Transmission Electron Microscopy (TEM) and Atomic Force Microscopy (AFM) Imaging.

The morphology of self-assembled adhesive fibers was assessed with Transmission Electron Microscopy (TEM) and Atomic Force Microscopy (AFM) imaging. TEM: Bright-field TEM images were collected on a FEI Tecnai G2 F20 S/TEM operated at an accelerating voltage of 200 kV after staining the samples with uranylacetate or gold nanoparticles. Samples of mature fibers were collected after aging overnight or for 3 days. Specifically, 10 µL of protein solution was directly deposited on carbon film-supported 400 mesh copper grids (Ted Pella, Inc.). Excess solution was quickly wicked away with a piece of filter paper and the sample dried. Once dried, samples were negatively stained with 2 µL 2 wt % uranyl acetate or PBS solution containing 1 wt % gold nanoparticles. AFM: Tapping mode (TM) AFM was performed on Asylum MFP-3D AFM (Asylum Research, Santa Barbara, Calif., USA) using Veecoprobes Sb-doped Si cantilevers ($\rho$=0.01-0.025 Ω-cm, k=40 N/m, $\upsilon$~300 kHz).

Thioflavin T (ThT) Assay.

Purified proteins were loaded on a 96-well black plate with transparent bottom. ThT was added to a concentration of 20 µM. Fluorescence was measured every 5 min after shaking 5 sec by a BioTek Synergy H1 Microplate Reader using BioTek GEN5 software set to 438 nm excitation and 495 nm emission with a 475-nm cutoff. ThT fluorescence for the polymerization of proteins was normalized by (Fi−F0)/(Fmax−F0). Fi was the ThT intensity (fluorescence arbitrary unit) of samples, and F0 was the ThT background intensity. $F_{max}$ was the maximum ThT intensity of samples.

Fluorescence Imaging.

All fluorescence images (including fluorescence microscopy, fluorescence spectra and fluorescence quantum yields) were recorded on a home built fluorescence microscopy platform based on a Nikon Ti-E PFS coupled with an Olympus IX70 inverted microscope frame (Olympus UK, Essex, UK). Ultraviolet-Visible (UV-Vis) absorption spectra were recorded at room temperature with a CARY-6000i spectrophotometer. Specific fluorescence filters were applied to show that proteins can exhibit intrinsic fluorescence under a wide range of visible spectrum. Acquisition of fluorescence images was controlled using the using Nikon Elements imaging software.

Spectrofluorometer Assays:

Excitation and emission spectra were measured at 25° C. using a fluorolog 3 spectrofluorometer (Horiba Jobin Yvon). The excitation spectra were measured with the detection wavelength fixed at 375 nm. The emission spectra were measured with the excitation wavelength fixed at 300 nm. For all measurements, excitation and emission slit widths were 2 nm and 4 nm respectively; the PMT voltage was 750 V; the scan speed was 120 nm min$^{-1}$.

Figure 13A:
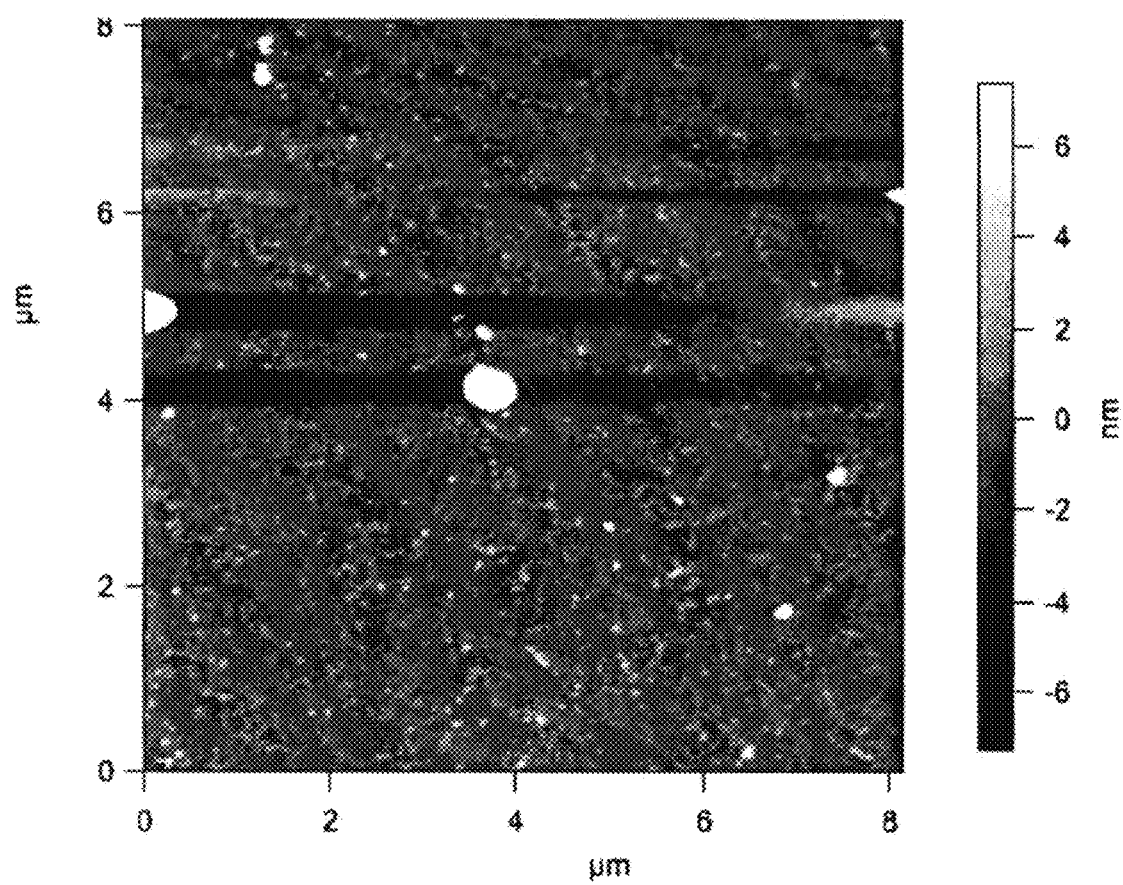
FIGS. 13A-13B depict a series of images.
Figure 13B:
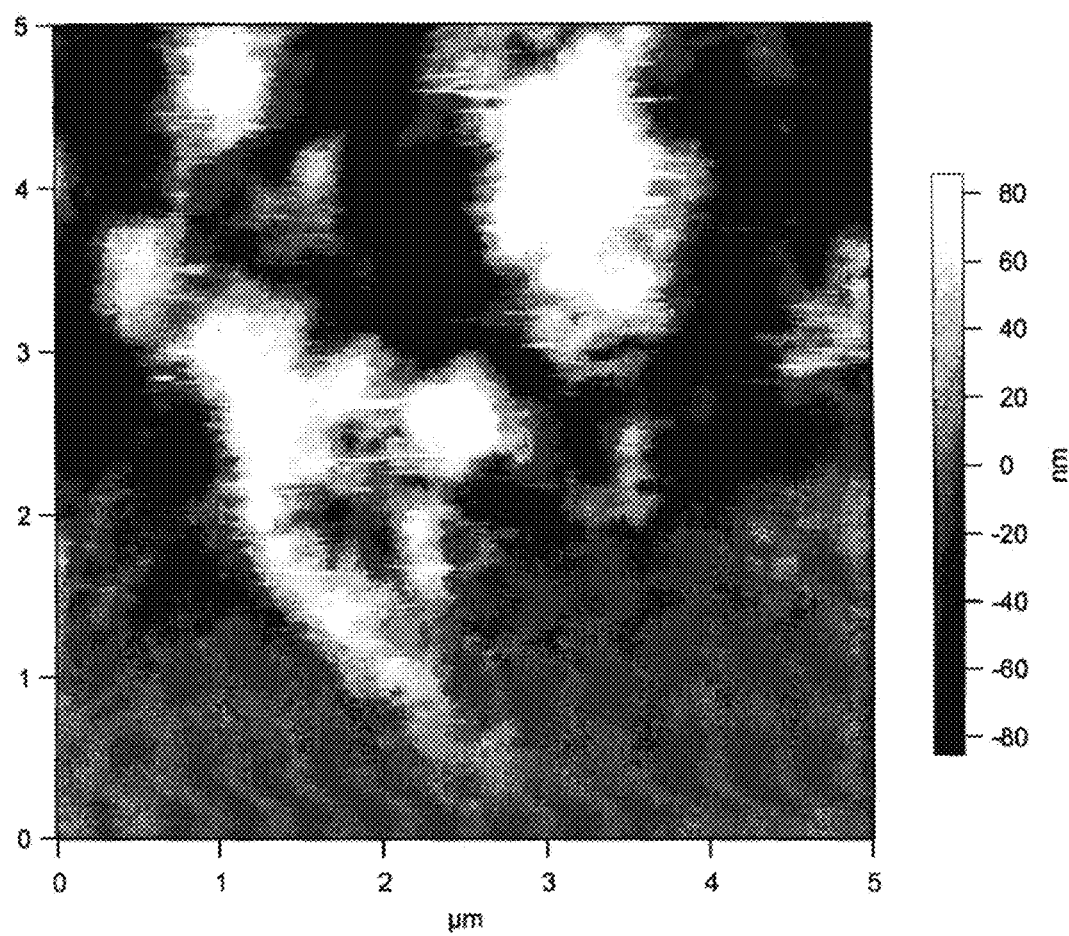

Fluorescence Quantum Yield: The fluorescence quantum yields (Q (%)) of adhesive fibers, defined as the ratio of photons absorbed to photons emitted through fluorescence, were assessed with the Williams comparative method28 using a standard blue fluorophore (Coumarin 102) with a known quantum yield of Q=76.4% in ethanol. For fluorescence quantum yield measurements, all the excitation wavelengths were fixed at 325 nm, and the emission spectra were recorded between 350 to 550 nm. Both the excitation and emission slits width were fixed at 1.5 nm. The integration time was 0.2 seconds. Detailed procedures for the determination of fluorescence quantum yields is described below. Atomic force microscopy (AFM) colloidal probe technique was used for adhesion force and adhesion energy assessment. This technique is based upon quantification of the adhesion interaction between a colloidal sphere (with well-defined size) and adhesive fibers (pre-absorbed on a planar surface, mica surface in the experiments). AFM force measurements were made at room temperature in buffered solution adjusted pH=2.5, 5.0, 7.0 and 10.0 using an Asylum MFP-3D AFM (Asylum Research, Santa Barbara, Calif., USA) mounted on top of an Olympus IX51 inverted optical microscope for visualizing and manually positioning regions to be probed. Force measurements (forcedistance curves) were made at a rate of 0.3 to 2.0 Hz, using Si3N4 or Si cantilevers modified with a glass sphere with a radius of 10 µm (Novascan) with calibrated spring constants between 0.6 and 14 N/m. The corresponding tips above refer to silica, Au, and PS tips in this study. Image processing and analysis of the force curve were performed using IGOR PRO (Wavemetrics, Lake Oswego, Oreg., USA) data analysis software and Origin 8.0 software (OriginLab Corporation, USA). All force measurements were made on three adhesive samples, with at least 200 force-extension curves taken for different regions of each adhesive sample. For sample preparation, proteins of interest with (10 μL solution with a concentration of 20 μM) were deposited and absorbed on a clean mica surface under buffered aqueous conditions (pH=2.0, 5.0, 7.0, or 10.0). Fibrous structures were typically found covering the mica surface after one-hour absorption (FIG. 13A). After force measurement, AFM contact mode tips were applied in wet condition to confirm that the measured sites contain fibrous structures (FIG. 13B). For each measurement, control test were also applied by directly measuring adhesion on a clean mica surface under the same conditions. These procedures thus ensured that all the presented force curves were measured on real samples rather than contaminated surfaces. Typical force curves measured on one spot (60 μm area) of a clean mica surface and a mica surface absorbed with fibrous structures were both shown in FIG. 13B and FIG. 14A. Finally, measured adhesion forces, Fad, taken at the point of the maximum force during retracting curve, are related to the adhesion energy per area (Ead) according to JKR theory for deformable surfaces, (Fad=1.5πREad, for a similar sphere/sphere system; For a dissimilar sphere/flat system, which was the case in the study, Fad=3πREad), where R is the radius of contact.

Molecular Dynamics Simulations and Modeling.

Construction of initial models. A model for the CsgA moiety was constructed by threading the CsgA amino acid sequence onto the solid-state NMR structure of the Abeta42 amyloid fibril (PDB ID code 2BEG)[33] using Modeller. The Abeta42 fibril strands were used as templates for the five repeating units of the CsgA sequence, such that the sidechains were oriented according to the model proposed by Collinson et al[31,32]. The linker and Mfp3/5 sequences were then joined to the CsgA using CHARMM. Fibril structures composed of five monomers each were constructed in CHARMM by fixing the relative motions of individual monomers and minimizing the H-bond distances between monomers such that they stacked in a non-staggered, in-register conformation. CHARMM parameters for DOPA residue hydroxyls were obtained from electrostatic calculations performed on Dopamine[34].

Unrestrained molecular dynamics simulations. Simulations were performed using a polar hydrogen model in the CHARMM19 forcefield and implicit EEF1 solvent (Lazaridis, T. & Karplus, M. Effective energy function for proteins in solution. *Proteins: Structure, Function, and Bioinformatics* 35, 133-152 (1999)). Each system was linearly heated to a temperature of 293.15K over 100 ps and then coupled to a Nose thermostat at the same temperature. They were then equilibrated for a further 100 ps before beginning the production runs. Monomers were simulated for a total of 1 microsecond, and fibrils for a total of 200 ns.

Replica exchange molecular dynamics simulations. Models for the CsgA-Mfp3 and Mfp5-CsgA fibrils (with and without DOPA modification) were subjected to replica exchange molecular dynamics (REMD) simulations. In the interest of computational tractability, all atoms in the CsgA residues were fixed in space, such that only the linker and Mfp residues were allowed to move. Sixteen replicas were used for each model, with temperatures exponentially spaced between 286.71K and 400.00K, such that the second replica corresponded to room temperature (293.15K). This temperature schedule was selected to ensure a swapping probability of as close to 20% as possible between adjacent temperature streams[35].

Secondary structure assignments. Secondary structure was assigned using STRIDE[36]. A residue was assigned to the class of 'helix' if it was assigned as ALPHA-helix, PI-helix or 3-10 helix by STRIDE. Similarly, a residue was assigned to the class of 'strand' if it was assigned as a bridge or extended by STRIDE.

Determination of Fluorescence Quantum Yields

Mechanism: The fluorescence quantum yield is an intrinsic property of a fluorophore and is defined as the ratio of photons absorbed to photons emitted through fluorescence. In this study, we adopted the Williams comparative method to determine the relative quantum yield of adhesive fibers. This approach involves the use of multiple well-characterized references with known fluorescence quantum yields. It is more time-consuming than a single-point method, but provides much higher accuracy by calculating the slope of the line generated by plotting the integrated luorescence intensity against the absorption for multiple concentrations of fluorophore.

Experimental procedures: The standard fluorophore used in the experiments was C102 (Coumarin 102), which has a quantum yield (Q)=0.764 in ethanol. Standard 10 mm path length quartz fluorescence cuvettes were used for all measurements. Ultraviolet-Visible (UV-Vis) absorption spectra were recorded at room temperature with a CARY-6000i spectrophotometer. Fluorescence and fluorescence excitation spectra were measured at room temperature using a FluoroLog 3 spectrometer manufactured by HORIBA Jobin Yvon. For fluorescence quantum yield measurements, the excitation wavelength was fixed at 325 nm, and the emission spectra were recorded between 350 to 550 nm. Both the excitation and emission slits width were fixed at 1.5 nm. The integration time was 0.2 seconds.

The UV-vis absorbance spectrum of the solvent background was first recorded for the chosen sample. The fluorescence spectrum of the same solution in the 10 mm fluorescence cuvette was correspondingly recorded. The integrated fluorescence intensity based on the area of the fluorescence spectrum from the fully corrected fluorescence spectrum was calculated. Following the same procedures, both UV-vis and fluorescence spectra were recorded for five solutions with increasing concentrations of the chosen samples; these samples had absorbances between 0.01 and 0.10 (at 325 nm). Graphs of integrated fluorescence intensities (between 350 nm and 550 nm) versus absorbances were plotted based on the data collected above. The results should follow a straight line with slope m, and intercept=0. The slopes are proportional to the quantum yields of the different samples. Absolute values were calculated using the standard samples, which have a fixed and known fluorescence quantum yield value, according to the equation:

$$Q = Q_R * (m/m_R) * (\eta^2/\eta^2_R)$$

Where, the subscript R denotes the reference sample,
m=slope from the plot of integrated fluorescence intensity vs absorbance for the adhesive proteins samples,
η=refractive index (η=1.33 was used for aqueous buffer, while η=1.36 was used for the ethanol solution in which the C102 dye was dissolved.)

Final results from data processing for determination of fluorescence quantum yield of adhesive fibers are presented in FIG. 9.

Detailed Procedures for Adhesion Force Measurements.

The AFM colloidal probe technique[13] was used for adhesion force and adhesion energy measurements. This technique is based upon quantification of the adhesion interactions between adhesive fibers (pre-absorbed on a planar surface, mica surface in the experiments) and a colloidal sphere (with well-defined size). It essentially measures the asymmetric adhesion of fibers, which pre-bind firmly to mica and bind to the AFM tip surface temporarily during measurement. AFM force measurements were made at room temperature in buffered solutions adjusted to pH=2.5, 5.0, 7.0 and 10.0 using an Asylum MFP-3D AFM (Asylum Research, Santa Barbara, Calif., USA) mounted on top of an Olympus IX51 inverted optical microscope for visualizing and manually positioning regions to be probed. Force measurements (force-displacement curves) were made at a rate of 0.3 to 2.0 Hz, using $Si_3N_4$ or Si cantilevers modified with a glass sphere (with a radius of 10 μm) or glass sphere coated with gold layers (with a radius of 10 μm) or polystyrene (PS) sphere (with a radius of 12.5 μm) (Novascan) with calibrated spring constants between 0.6 and 14 N/m. The corresponding tips above refer to silica, Au, and PS tips in this study. Image processing and analysis of force curves was performed using IGOR PRO (Wavemetrics, Lake Oswego, Oreg., USA) data analysis software and Origin 8.0 software (OriginLab Corporation, USA). For each type of adhesive fiber tested, we performed at least 64 measurements; specifically, we measured at 16 random fiber spots in force mapping mode with a scanning diameter ~20-100 μm in at least 4 different groups. After each group measurement operated under force mapping mode, we also applied continuous measurement mode in our study by performing adhesion tests at a specific fiber spot with a total of 20 continuous measurements to ensure that data obtained through both measurement modes were consistent with each other. Only data from force mapping mode were used for all statistic assessment in this study.

Figure 14A:
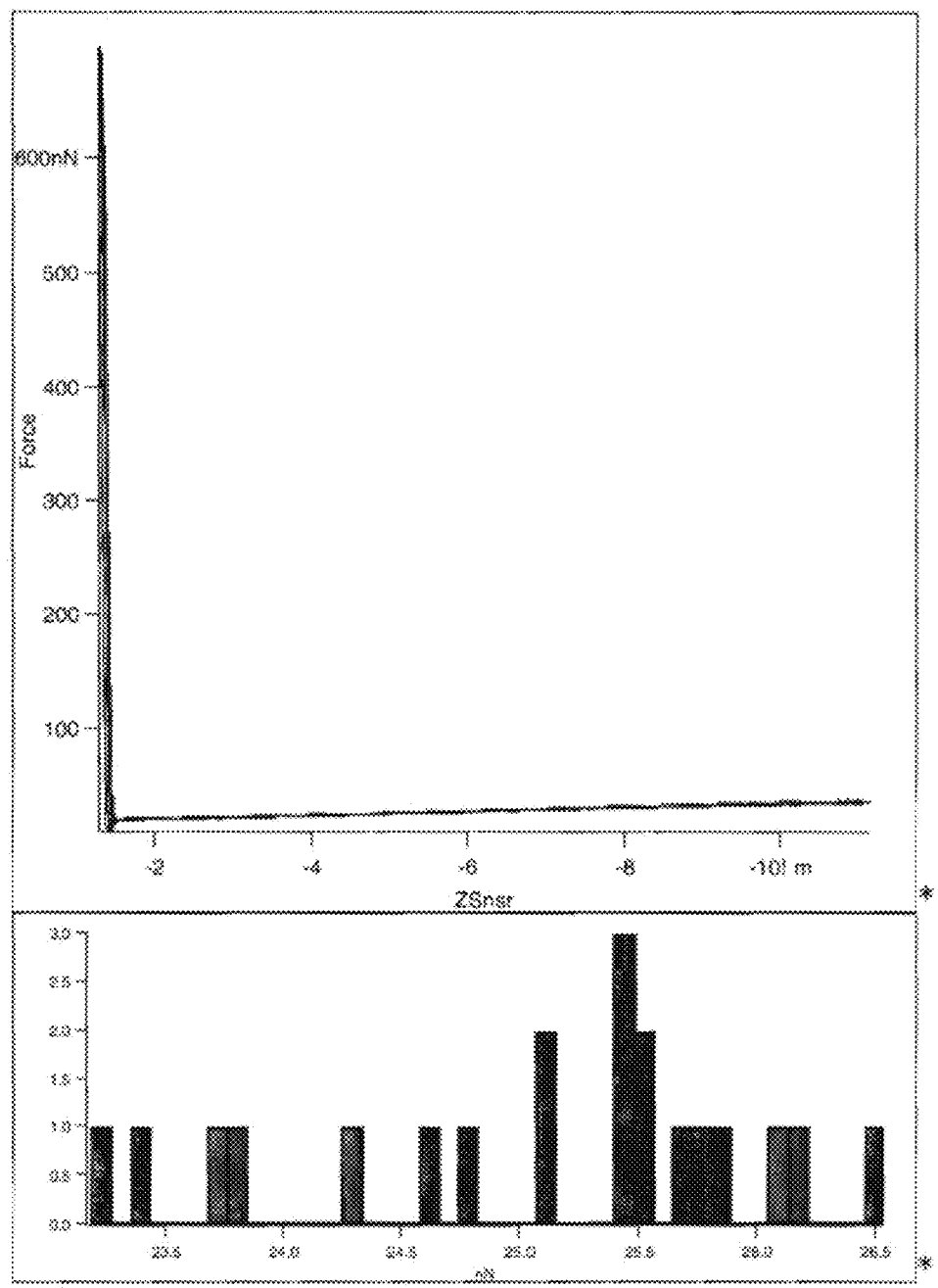
FIGS. 14A-14B depict a series of data sets.
Figure 14B:
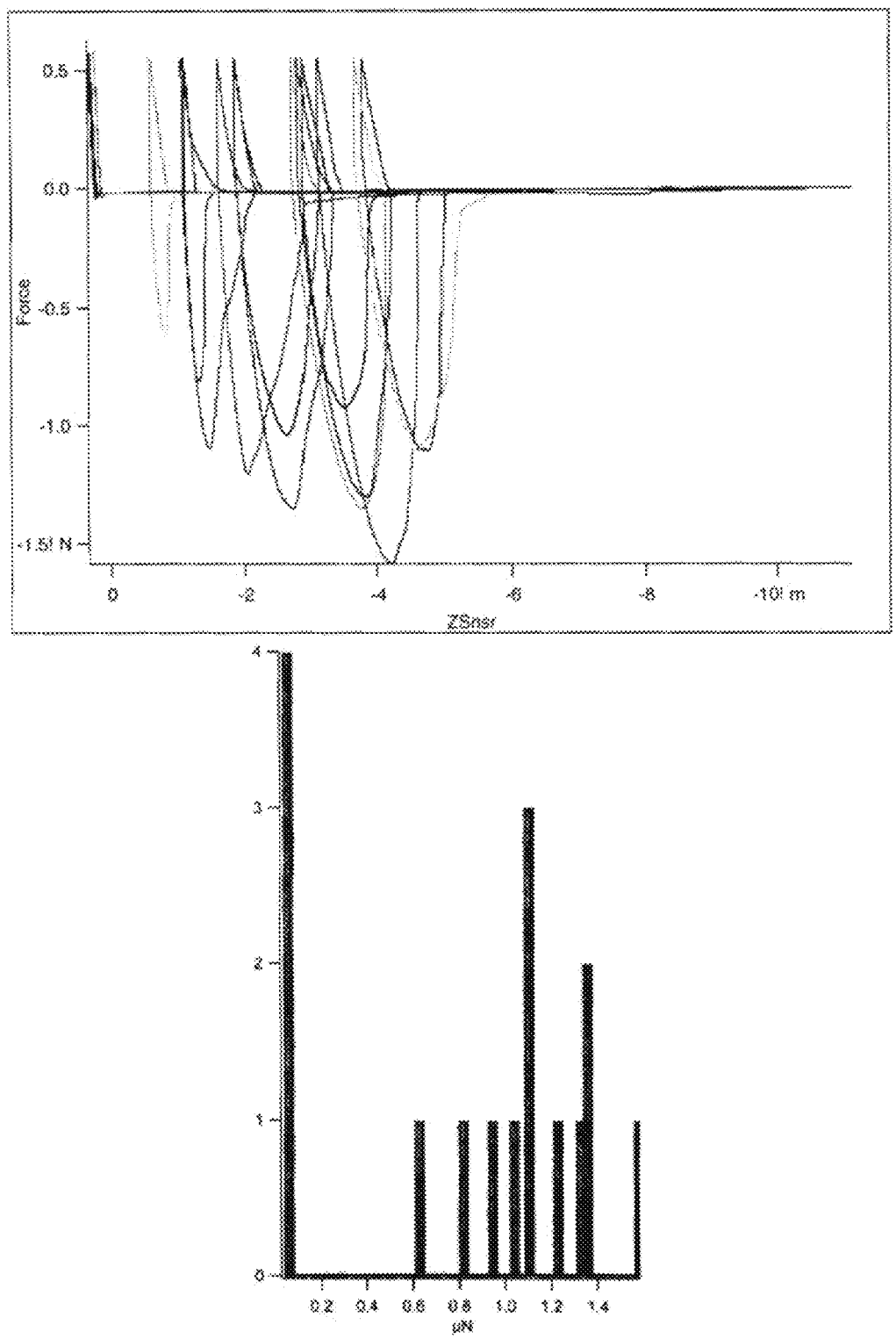

For sample preparation, 10 μL of 20 μM protein solutions were deposited and adsorbed on a clean mica surface under buffered aqueous conditions (pH=2.5, 5.0, 7.0 or 10.0). Fibrous structures were typically found covering the mica surface after one hour of adsorption. After force measurements, we applied AFM contact mode tips in wet conditions to confirm that the measured sites contained fibrous structures. For each sample measurement, we also applied control tests by directly measuring adhesion on a clean mica surface under the same conditions. These procedures thus ensured that all the presented force curves were measured on real samples rather than contaminated surfaces. Typical force curves measured on a clean mica surface (as a negative control) are shown in FIG. 14a.

Finally, measured adhesion forces, Fad, taken at the point of maximum force on the retraction curves, were related to the adhesion energy per area (Ead) according to the Johnson-Kendall-Roberts (JKR)14 theory for deformable surfaces.

For a similar sphere/sphere system:

$$F_{ad}=1.5 7\pi RE_{ad};$$

For a dissimilar sphere/flat system, which is the case in our study:

$$F_{ad}=3\pi RE_{ad};$$

where R is the radius of contact.

The reported forces and adhesion energies in this paper are given as absolute values.

Statistics.

Data are presented as mean±SD (standard deviation). SD was calculated based on at least 3 replicates (for force measurements, this refers to at least 4×16=64 force curves for each type of proteins). A Student's t test was used to compare data sets and a P value less than 0.01 and 0.05 was considered statistically significant between two marked groups or samples.

Example 1

Introduction. In the research reported here, self-assembling hybrid adhesives were produced that recapitulate adhesive features of two independent natural adhesion systems: DOPA-based adhesives and amyloid-like adhesives. The research was based upon a rational modular design utilized in synthetic biology which reassembles standardized biological components in a systematic and rational manner,[18] and has produced self-assembling nanostructures,[19,20] muscle-mimic biomaterials[21] and biological designer devices with useful and novel functions.[22] As illustrated in FIG. 1, this process was leveraged to produce a new generation of underwater adhesives. CsgA (a representative of amyloid-like adhesives) and Mfp3 and Mfp5 (representatives of DOPA-based adhesives) were recombined to form novel fusions (FIG. 1A). Two representative fusion constructs, CsgA-Mfp3 (C-terminal fusion of Mfp3) and Mfp5-CsgA (N-terminal fusion of Mfp5), were selected from 24 proposed designs predicted to self-assemble into fibril structures (Table 1). Because CsgA domain is of amyloidogenic feature, it was reasoned that both CsgA-Mfp3 and Mfp5-CsgA would form hierarchical fibrous bundles or films following a typical self-assembling pathway for amyloidogenic proteins[23] (FIG. 1D).

Figure 6:
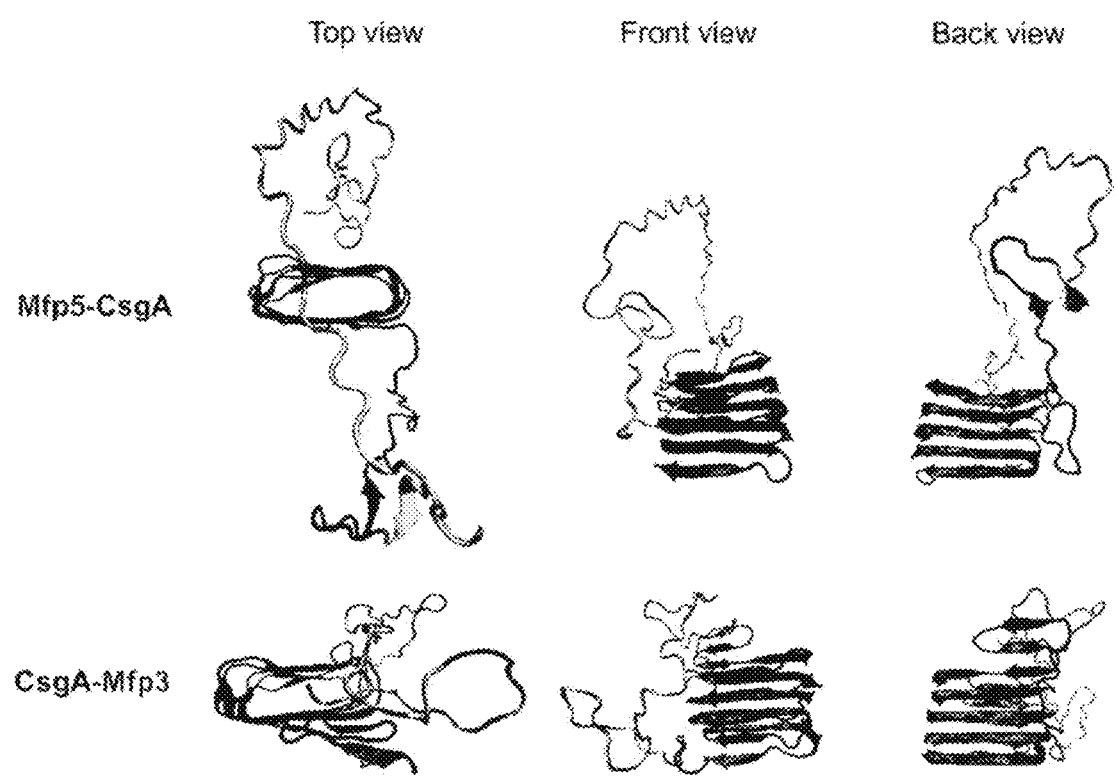
FIG. 6 depicts the predicted structures of monomer models constructed for Mfp5-CsgA and CsgA-Mfp3.

Production of Self-Assembling Hybrid Adhesives. To evaluate whether CsgA-Mfp3 and Mfp5-CsgA form hierarchical fibrous bundles or films that would allow for a self-assembling pathway, molecular dynamics simulation was used to predict the stability of the CsgA amyloid cores and to assess the secondary structures of the Mfp domains in constructed models representing both monomeric and fibriliar states (FIG. 2 and FIG. 6). For amyloid stability assessment, the backbone C-α RMSD of CsgA domain of the final simulated structures was compared with the initial models (FIG. 2 and Table 2). The CsgA residues within both monomers deviated by less than 5 Angstroms from the initial models over microsecond long simulations, whereas CsgA alone gave a deviation of 5.73 Angstroms (Table 2). Furthermore, the CsgA residues within both fibril models deviated by less than 4 Angstroms over 200 nanosecond long simulations (Table 2). Replica exchange molecular dynamics simulations (REMDS) were adopted to assess secondary structures of the Mfp domains in fibril models. Over 200 nanosecond long simulations, 0% helical content, and 23% and 30% strand contents were found in the Mfp3 and Mfp5 domains, respectively (FIG. 2E). Collectively, these results showed that both CsgA Mfp3 and Mfp5-CsgA form stable amyloid structures dominated by CsgA domains, with a highly disordered nature of the Mfp domains displaying external to the amyloid core.

Figure 3A:
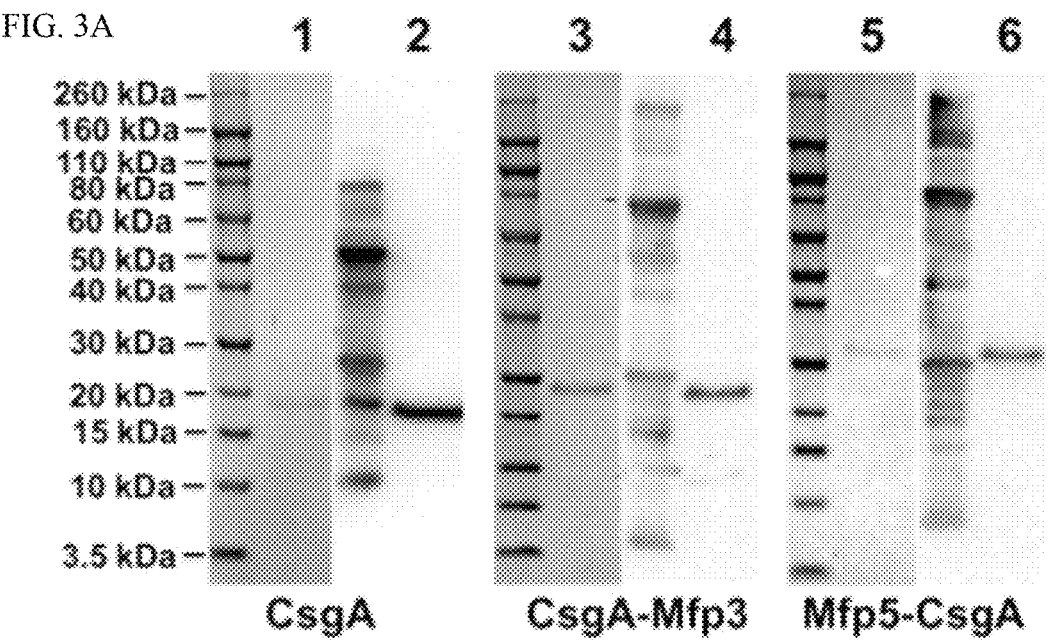
Figure 3B:
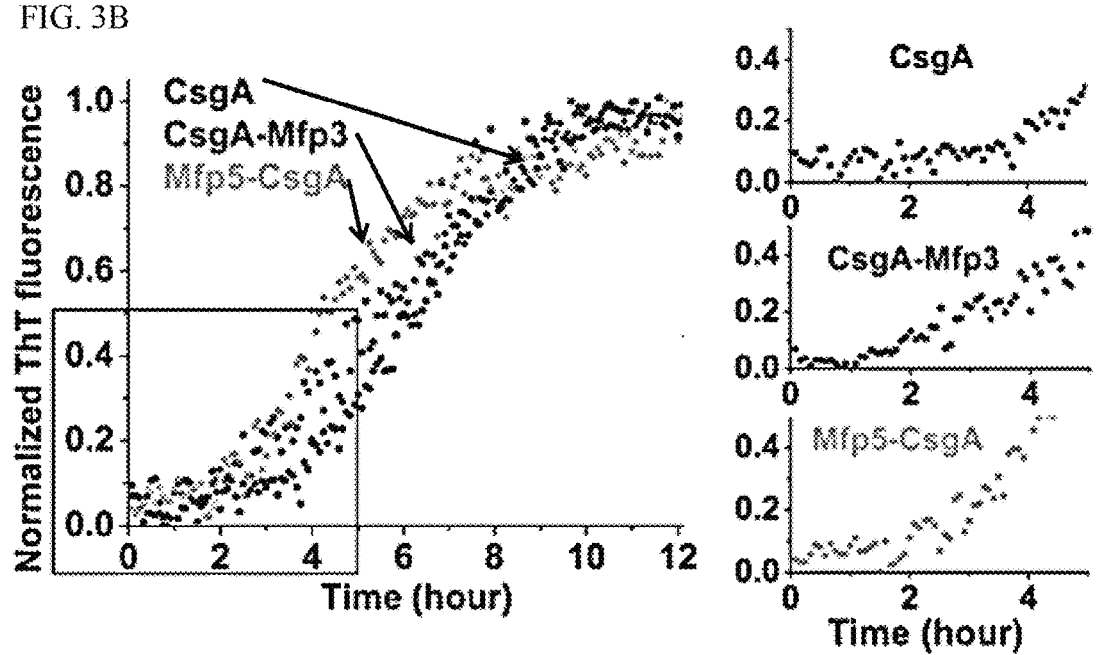
Figure 7:
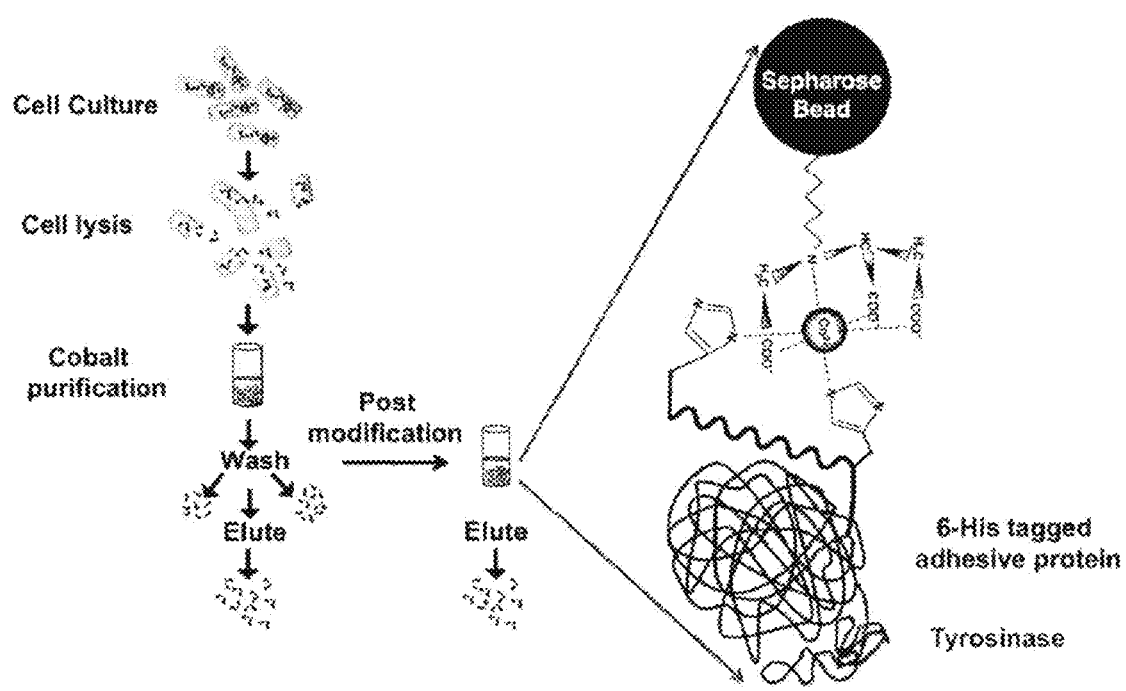
FIG. 7 depicts a schematic diagram of purification and post-modification of target adhesion proteins by mushroom tyrosinase during protein purification process. Right: Sepharose bead in TALON resin bearing the tetradentate chelator of the $Co^{2+}$ metal ion. The 6 histidine-tagged recombinant adhesive protein in monomer form binds to the resin with tyrosine residues exposed for modification by tyrosinase.
Figure 8:
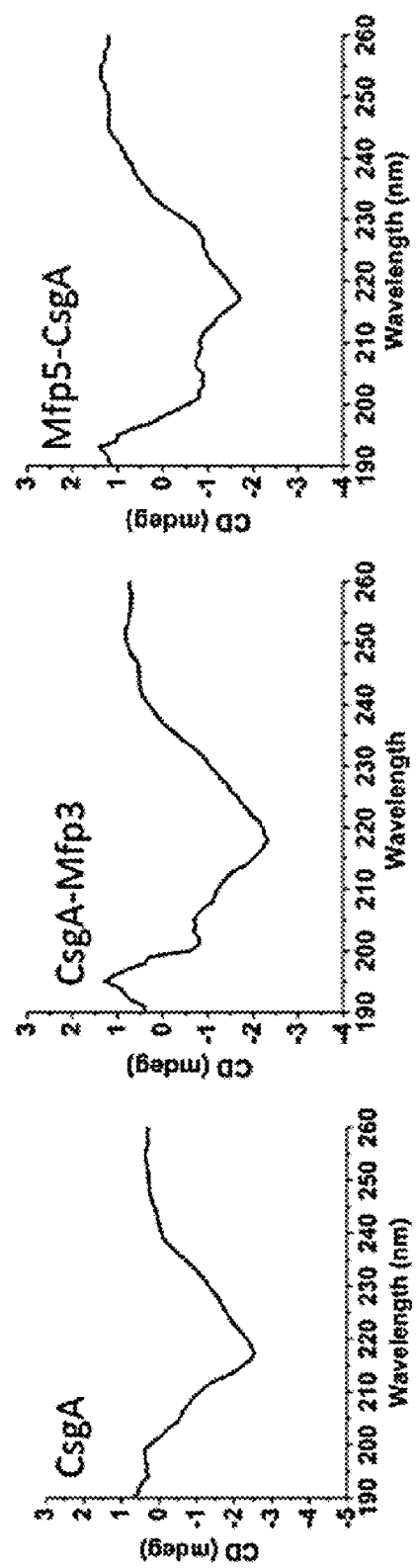
FIG. 8 depicts circular dichroism spectra showing that both CsgA-Mfp3 and Mfp5-CsgA exhibit a strong beta-sheet profile with a minima at a wavelength 216 nm. The curve shapes for both proteins are slightly different from CsgA, likely arising from the unstructured features of Mfp domains displaying external to the amyloid core.

Genes encoding the designed proteins with appended C-terminal (His)$_6$ tags were constructed and cloned into an expression vector. The designed proteins expressed in E. coli were then purified under combined denaturing/non-denaturing conditions by cobalt-affinity chromatography. An additional in vitro post-modification step (by enzyme tyrosinase) was carried out under non-denaturing condition before eluting proteins from the cobalt resin column (FIG. 7). CsgA-Mfp3 and Mfp5-CsgA migrated as single band at 28.5 KD and 32 KD respectively under SDS-polyacrylamide gel electrophoresis (PAGE), in contrast with the single band at 17 KD for CsgA. All bands were further recognized by antibodies to His tag (anti-His) (FIG. 3A). Immediately after elution from the cobalt resin column, solutions containing CsgA-Mfp3 and Mfp5-CsgA were clear with no evidence of aggregation. However, after about 2-hour prolonged incubation at ambient conditions the solutions became opaque and noticeably viscous and sticky. Such transition of soluble proteins to insoluble aggregates can be monitored using Thioflavin T (THT), an amyloid-specific dye commonly used to assay amyloid formation[24]. The THT fluorescence of all samples followed a sigmoidal curve with distinguishable lag, growth, and stationary phases (FIG. 3B). However, the polymerization lag phase for CsgA-Mfp3 and Mfp5-CsgA was typically shorter than CsgA, suggesting that the fusion of Mfp domain into CsgA sped up amyloid formation. Such observation can be explained by the fly-casting mechanism, which postulates that a relatively unstructured protein can have a greater "capture radius" and thus enhance intermolecular recognition and binding rate[25,26]. The formation of long fibers was confirmed for both CsgA-Mfp3 and Mfp5-CsgA under TEM, with no apparent difference in morphology and fiber size. However, the average diameter of the modified fibers was three times that of CsgA. Collectively this evidence, along with circular dichroism (CD) analysis (FIG. 8), showed that both designed proteins were rich in β-sheet secondary structure in solution, in agreement with molecular dynamic modeling. Interestingly, both proteins, either upon incubation of freshly made soluble proteins over existing nanofiber seeds or upon direct incubation at high solution concentration, assembled into larger fiber bundles and even thick hierarchical films composed of fibril features (FIG. 9 and FIG. 10).

Figure 3I:
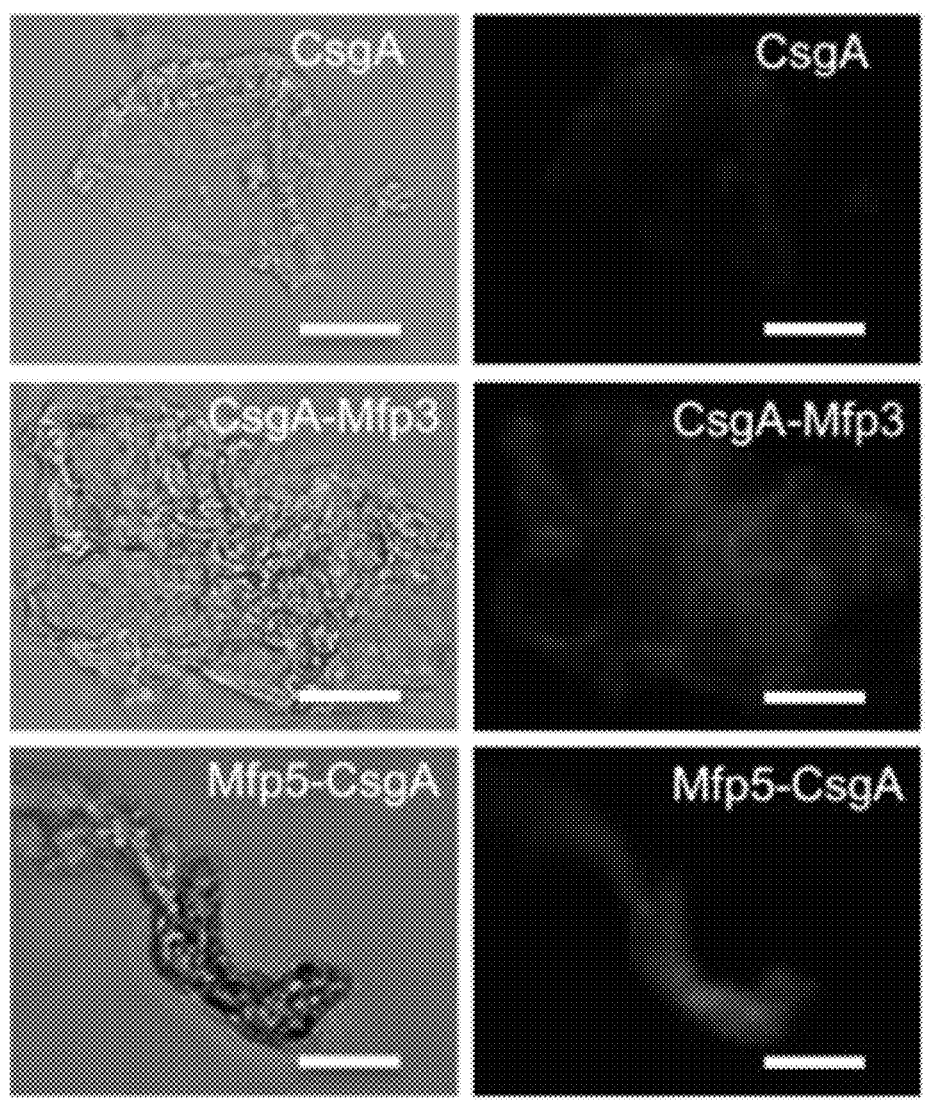
Figure 11:
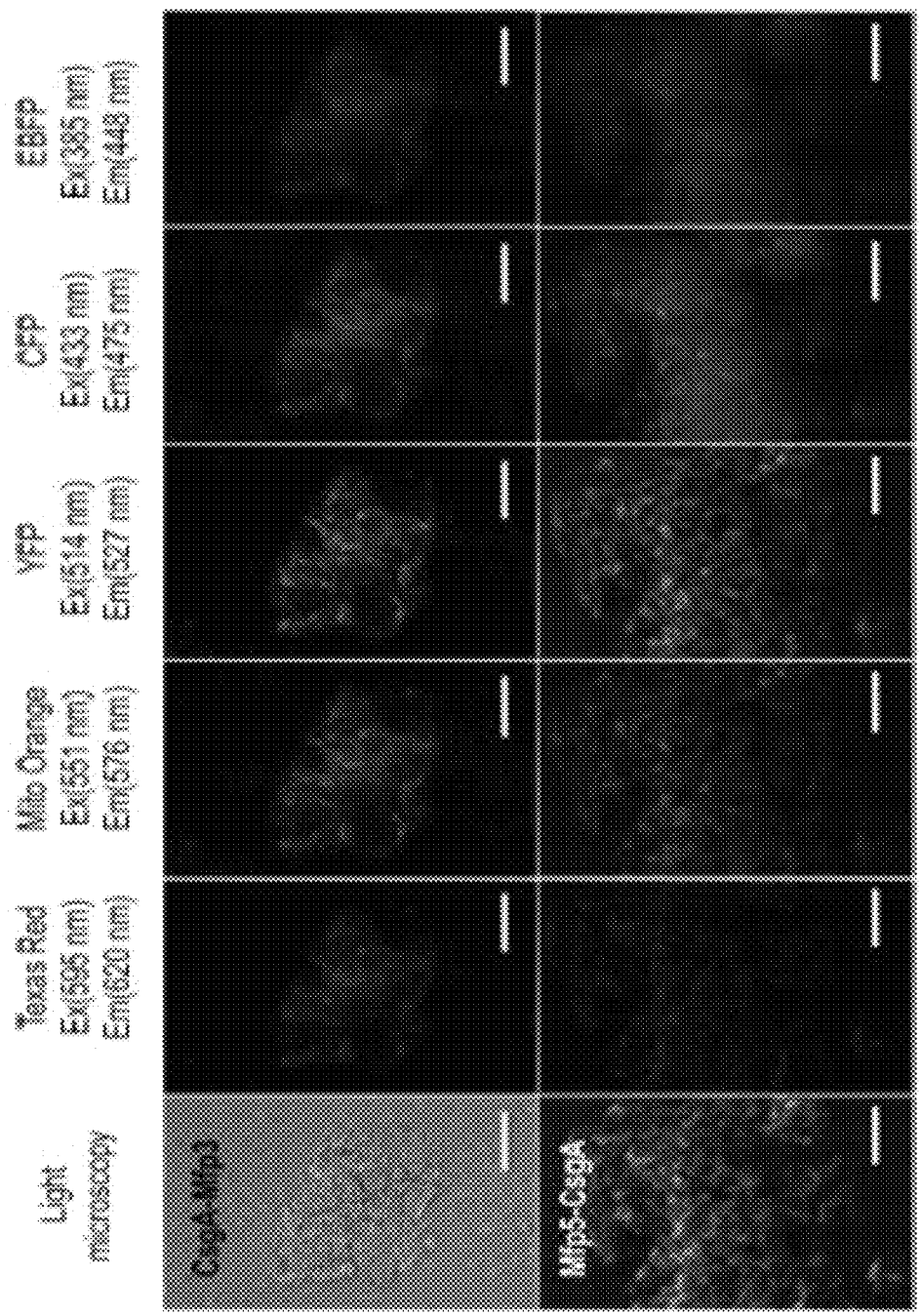
FIG. 11 depicts a series of fluorescence images of modified CsgA-Mfp3 and Mfp5-CsgA proteins detected with standard imaging system, excited at different wavelength by applying five different fluorescence filters. Scale bar 30 μm. The term "modified" means some or all of the tyrosine residues of the proteins are converted to DOPA residues.

A remarkable feature of both proteins is their intrinsic fluorescence signatures in the visible spectrum range (FIG. 3I). Fluorescence was detected in aged solutions, but not in freshly made solutions, showing that fiber formation is a precondition for fluorescence detection. Furthermore, spectra analysis indicated that for Mfp5-CsgA, CsgA-Mfp3 and CsgA the excitation maxima are near 318, 312, and 306 nm, respectively, while the emission maxima are all close to 378 nm (FIG. 3G). Mfp5-CsgA displayed higher fluorescence intensity than both CsgA-Mfp3 and CsgA when measured in solutions of almost the same concentrations as well as in bulk fiber bundles (FIGS. 3G and 3I). The higher fluorescence intensity may arise from higher percentage of aromatic residues in Mfp5-CsgA (12.5%), in contrast with 10.8% and 5.8% for CsgA-Mfp3 and CsgA, respectively. In addition, when excited at different wavelengths, Mfp5CsgA and CsgA-Mfp3 both emit different fluorescent colors from blue to red (FIG. 11), in agreement with the spectrum results (FIG. 3H).

Although the specific mechanism is unknown, these results suggest that the formation of β-sheet structures and high percentage of aromatic side-chains both contribute to the intrinsic fluorescence signatures of adhesive proteins. It is relevant that intrinsic fluorescence feature was also discovered in human disease-related peptide amyloid-β (1-40) and other non-functional amyloid structures. It has been suggested that this arises from the electron delocalisation via hydrogen bonds in β-sheet structure.[27,28] Because photoluminescent biomaterials have particular applications in medical fields[29], these adhesive biomaterials with intrinsic fluorescence are suitable for medical applications. For example, they could be used as fluorescence probes to monitor implant interface of medical devices.

TABLE 2

Backbone C-α RMSD of residues 22:131 on CsgA (strand residues)

| | RMSD average (Angstroms) | RMSD final (Angstroms) |
|---|---|---|
| CsgA alone | 5.59 | 5.73 |
| CsgA (with Mfp3, monomer) | 4.37 | 4.75 |
| CsgA (with Mfp3, fibril form) | 2.27 | 2.88 |
| CsgA (with Mfp5, monomer) | 3.66 | 3.87 |
| CsgA (with Mfp5, fibril form) | 4.01 | 3.81 |

Evaluating Underwater Adhesion Properties

Figure 4A:
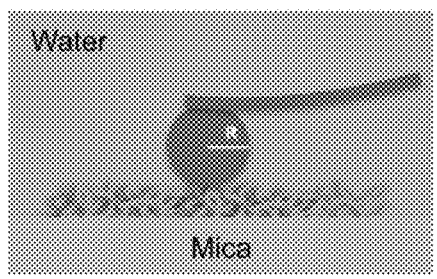
FIGS. 4A-4D depicts the adhesion force measurement of adhesive proteins by atomic force microscopy (AFM) colloidal probe technique.
Figure 4B:
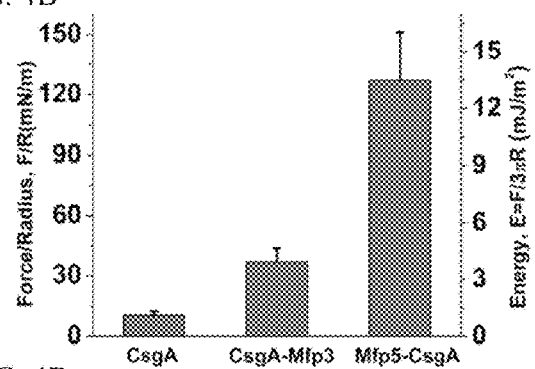
Figure 4C:
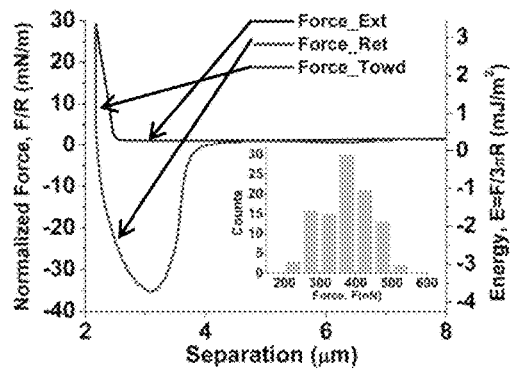
Figure 4D:
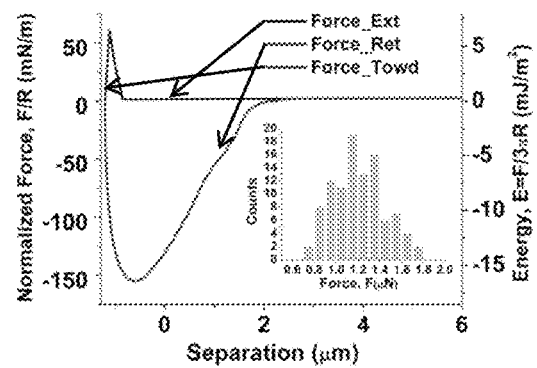
Figure 12A:
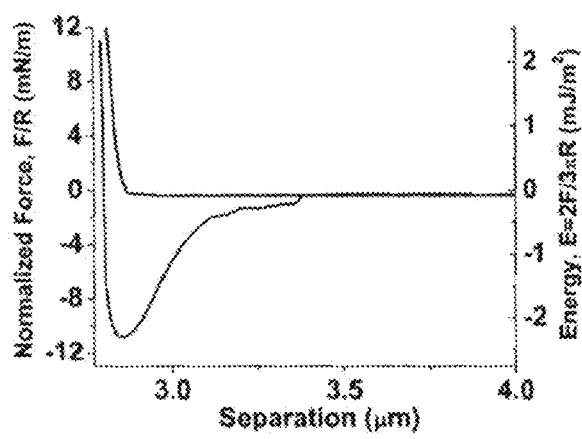
FIGS. 12A-12B depict a data set.
Figure 12B:
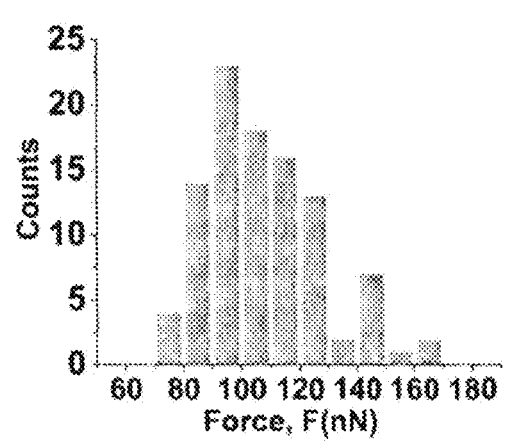

Atomic force microscopy (AFM) colloidal probe technique[30] (FIG. 4A) was used to assess the underwater adhesion performance of the adhesive proteins. Proteins were deposited and absorbed on a clean mica surface under buffered aqueous conditions (pH=5.0 or 2.0). Fibrous structures were typically found covering the mica surface after one-hour absorption. (FIG. 13). Among the three proteins tested, Mfp5-CsgA displayed the best underwater adhesion, with normalized adhesion force (F/R) and adhesion energy ($E_{ad}$) about 127 mN/m and 13.7 mJ/m$^2$, respectively (FIG. 4D). These values are about three-fold higher than CsgA-Mfp3 and ten times higher than CsgA measured under the same conditions (FIG. 4B and FIG. 12). The adhesive function of Mfp5-CsgA was better than CsgA-Mfp3, which is consistent with previous findings showing that Mfp5 displays better adhesion than Mfp3[11]. The adhesion energy of Mfp5-CsgA was also four times higher than the reported recombinant Mfp5, a soluble protein displaying non-fibrous morphologly[8]. These results suggest that fiber morphology and the adhesive Mfp domains synergistically contribute to adhesive functions. Amyloid fiber structures may provide more surface area for contact because of the large fiber surface feature while endowing materials with greater cohesive strength. The disordered Mfp domains exposed on the fiber surface can further serve as adhesive residues for increased adhesive strength.

Notably, the adhesion energy of Mfp5-CsgA (measured under pH=5.0) is comparable to the most adhesive protein Mefp5 (*Mytilus edulis* foot protein-5) reported so far-despite lacking of additional post-modification such as phosphorylation on serine residues that likely contribute to adhesion in naturally produced Mfp5[11]. Furthermore, the proteins seem to tolerate oxidation at higher pH values (up to pH 5.0). This was inferred from the observation that both Mfp5-CsgA and CsgA-Mfp3 displayed similar level of adhesion in buffer solutions at pH values of 2.0 and 5.0.

Collectively, the engineered adhesives with strong wet bonding strengths, material robustness and intrinsic fluorescence have many advantages over current biomimetic and natural adhesives. There are broad applications for both technical and medical applications.

REFERENCES

1 Stewart, R. J., Ransom, T. C. & Hlady, V. Natural Underwater Adhesives. *Journal of Polymer Science Part B—Polymer Physics* 49, 757-771, doi: 10.1002/polb.22256 (2011).

2 Lee, B. P., Messersmith, P. B., Israelachvili, J. N. & Waite, 1. H. in *Annual Review of Materials Research Vol. 41* 99-132 (2011).

3 Anika S. Mostaert, S. P. J. in *The Functional Fold: Amyloid Structures in Nature* (ed Suzi Jarvis; Anika Mostaert) Ch. 8, 131-146 (Pan Stanford, 2012).

4 Chapman, M. R. et al. Role of *Escherichia coli* curli operons in directing amyloid fiber formation. *Science* 295, 851-855 (2002).

5 Stewart, R. J. Protein-based underwater adhesives and the prospects for their biotechnological production. *Applied Microbiology and Biotechnology* 89, 2733, doi: 10.1007/s00253-010-2913-8 (2011).

6 Yin, M., Yuan, Y, Liu, C. S. & Wang, J. Development of mussel adhesive polypeptide mimics coating for in-situ inducing re-endothelialization of intravascular stent devices. *Biomaterials* 30, 2764-2773, doi:10.1016/j.biomaterials.2009.01.039 (2009).

7 Sedo, J., Saiz-Poseu, J., Busque, F. & Ruiz-Molina, D. Catechol-Based Biomimetic Functional Materials. *Advanced Materials* 25, 653-701, doi: 10.1002/adma.201202343 (2013).

8 Hwang, D. S., Yoo, H. J., Jun, 1. H., Moon, W. K. & Cha, H. J. Expression of functional recombinant mussel adhesive protein Mgfp-5 in *Escherichia coli*. *Applied and Environmental Microbiology* 70, 3352-3359, doi: 10.1128/aem.70.6.3352-3359.2004 (2004).

9 Hwang, D. S., Gim, Y., Yoo, H. J. & Cha, H. J. Practical recombinant hybrid mussel bloadhesive fp-151. *Biomaterials* 28, 3560-3568 (2007).

10 Lee, H., Dellatore, S. M., Miller, W. M. & Messersmith, P. B. Mussel-inspired surface chemistry for multifunctional coatings. *Science* 318, 426-430, doi: 10.1126/science.1147241 (2007).

11 Danner, E. W., Kan, Y. J., Hammer, M. 0., Israelachvili, 1. N. & Waite, J. H. Adhesion of Mussel Foot Protein Mefp-5 to Mica: An Underwater Superglue. *Biochemistry* 51, 6511-6518, doi: 10.1021/bi3002538 (2012).

12 Brubaker, C. E. & Messersmith, P. B. The Present and Future of Biologically Inspired Adhesive Interfaces and Materials. *Langmuir* 28, 2200-2205, doi: 10.1021/la300044v (2012).

13 Hwang, D. S. & Waite, J. H. Three intrinsically unstructured mussel adhesive proteins, mfp-1, mfp-2, and mfp-3: Analysis by circular dichroism. *Protein Science* 21, 1689-1695 (2012).

14 Shafiq, Z. et at. Bioinspired Underwater Bonding and Debonding on Demand. *Angewandte Chemie-International Edition* 51, 4332-4335, doi: 10.1002/anie.201108629 (2012).

15 Knowles, T. P. 1. & Buehler, M. J. Nanomechanics of functional and pathological amyloid materials. *Nature Nanotechnology* 6, 469-479, doi: 10.1038/nnano.2011.102 (2011).

16 Knowles, T. P. et al. Role of intermolecular forces in defining material properties of protein nanofibrils. *Science* 318, 1900-1903, doi: 10.1126/science.1150057 (2007).

17 Barlow, D. E. et al. Characterization of the Adhesive Plaque of the Barnacle *Balanus amphitrite*: Amyloid-Like Nanofibrils Are a Major Component. *Langmuir* 26, 6549-6556, doi: 10.102111a9041309 (2010).

18 Weber, W. & Fussenegger, M. Emerging biomedical applications of synthetic biology. *Nature Reviews Genetics* 13, 21-35, doi:10.1038/nrg3094 (2012).

19 Padilla, J. E., Colovos, C. & Yeates, T. O. Nanohedra: Using symmetry to design self assembling protein cages, layers, crystals, and filaments. *Proceedings of the National Academy of Sciences of the United States of America* 98, 2217-2221, doi: 10.1073/pnas.041614998 (2001).

20 Sinclair, J. c., Davies, K. M., Venien-Bryan, C. & Noble, M. E. M. Generation of protein lattices by fusing proteins with matching rotational symmetry. *Nature Nanotechnology* 6, 558-562, doi: 10.1038/nnano.2011.122 (2011).

21 Lv, S. et al. Designed biomaterials to mimic the mechanical properties of muscles. *Nature* 465, 69-73, doi: 10.1038/nature09024 (2010).

22 Cheng, A. A. & Lu, T. K. in *Annual Review of Biomedical Engineering, Vol 14* Vol. 14 *Annual Review of Biomedical Engineering* (ed M. L. Yarmush) 155-178 (2012).

23 Knowles, T. P. J., Oppenheim, T. W., Buell, A. K., Chirgadze, D. Y. & Weiland, M. E. Nanostructured films from hierarchical self-assembly of amyloidogenic proteins. *Nature Nanotechnology* 5, 204-207, doi: 10.1038/nnano.2010.26 (2010).

24 Wang, X., Zhou, Y., Ren, J.-J., Hammer, N. D. & Chapman, M. R. Gatekeeper residues in the major curlin subunit modulate bacterial amyloid fiber biogenesis. *Proceedings of the National Academy of Sciences of the United States of America* 107, 163-168, doi: 10.1073/pnas.0908714107 (2010).

25 Shoemaker, B. A., Portman, J. J. & Wolynes, P. G. Speeding molecular recognition by using the folding funnel: The fly-casting mechanism. *Proceedings of the National Academy of Sciences of the United States of America* 97, 8868-+, doi: 10.1073/pnas.160259697 (2000).

26 Sugase, K., Dyson, H. J. & Wright, P. E. Mechanism of coupled folding and binding of an intrinsically disordered protein. *Nature* 447, 1021-UI011, doi: 10.1038/nature05858 (2007).

27 Chan, F. T. S. et al. Protein amyloids develop an intrinsic fluorescence signature during aggregation. *Analyst* 138, 2156-2162, doi:10. 1039/c3an36798c (2013).

28 del Mercato, L. L. et al. Charge transport and intrinsic fluorescence in amyloidlike fibrils. *Proceedings of the National Academy of Sciences of the United States of America* 104, 18019-18024, doi: 10.1073/pnas.0702843104 (2007).

29 Yang, J. et al. Development of aliphatic biodegradable photoluminescent polymers. *Proceedings of the National Academy of Sciences of the United States of America* 106, 10086-10091, doi:10.1073/pnas.0900004106 (2009). 30 Leite, F. & Herrmann, P. Application of atomic force spectroscopy (AFS) to studies of adhesion phenomena: a review. *Journal of adhesion science and technology* 19, 365-405 (2005).

30 Leite, F. & Herrmann, P. Application of atomic force spectroscopy (AFS) to studies of adhesion phenomena: a review. *Journal of adhesion science and technology* 19, 365-405 (2005).

31 Collinson, S. K, Parker, J. M. R., Hodges, R. S. & Kay, W. W. Structural predictions of AgfA, the insoluble fimbrial subunit of *Salmonella* thin aggregative fimbriae. *Journal of Molecular Biology* 290, 741-756, doi: 10.1006/jmbi.1999.2882 (1999).

32 Barnhart, M. M. & Chapman, M. R. in *Annual Review of Microbiology* Vol. 60 *Annual Review of Microbiology* 131-147 (2006).

33 Luhrs, T. et al. 3D structure of Alzheimer's amyloid-beta (1-42) fibrils. *Proceedings of the National Academy of Sciences of the United States of America* 102, 17342-17347, doi: 10.1 073/pnas.0506723102 (2005).

34 Urban, J. J. & Famini, G. R. THEORETICAL-STUDIES OF THE CONFORMATION OF DOPAMINE AND STRUCTURAL ANALOGS. *Abstracts of Papers of the American Chemical Society* 205, 210-0RGN (1993).

35 Kone, A. & Kofke, D. A. Selection of temperature intervals for parallel tempering simulations. *Journal of Chemical Physics* 122, doi: 10. 1063/1.1917749 (2005).

36 Heinig, M. & Frishman, D. STRIDE: a web server for secondary structure assignment from known atomic coordinates of proteins. *Nucleic Acids Research* 32, W500-W502, doi: 1O.1093/nar/gkh429 (2004).

37 Taylor, S. W. Chemoenzymatic synthesis of peptidyl 3,4dihydroxyphenylalanine for structure-activity relationships in marine invertebrate polypeptides. *Analytical Biochemistry* 302, 70-74, doi: 10.1006/abio.2001.5522 (2002).

Example 2

Figure 1C:
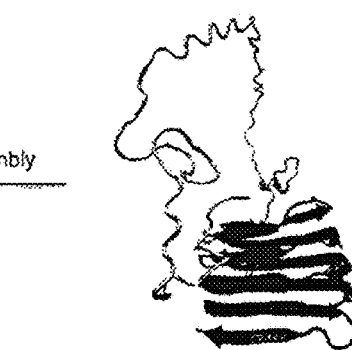
Figure 1F:
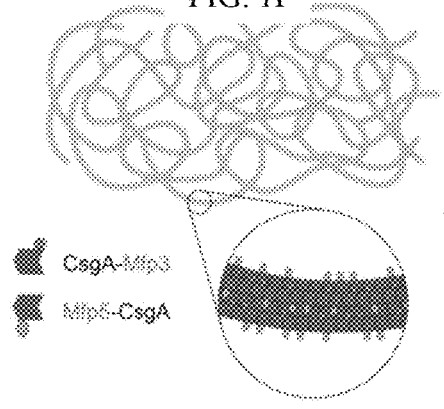
Figure 1E:
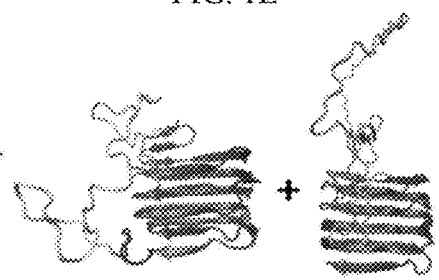

A listing of references cited in this example is provided at the end of example 2. We used rational design and synthetic-biology techniques to create a new generation of bio-inspired adhesives that combine two independent natural adhesion systems: Dopa-based adhesives and amyloid-based adhesives (FIG. 1). To achieve strong interfacial underwater adhesion, we selected Mfp3 and Mfp5 (representatives of Dopa-based mussel adhesives originating from *M. galloprovincialis*$_2$) and CsgA (an amyloidogenic protein which constitutes the major subunit of adhesive curli fibers in *E. coli*[19]) (FIG. 1a) from an inventory of adhesive biomolecules and genes compiled over decades of molecular biology and functional genomics research. Two genetic fusion constructs, CsgA-Mfp3 and Mfp5-CsgA, were constructed using isothermal one-step Gibson DNA assembly (FIG. 1b). Because CsgA is amyloidogenic, we reasoned that both CsgA-Mfp3 and Mfp5-CsgA would self-assemble into fibrous bundles or films with adhesive properties[20] by displaying the mussel adhesion domains on the surface of amyloid scaffolds. We further hypothesized that the co-assembly of the two fusion proteins together would lead to hierarchically assembled copolymer structures that could integrate synergistic features from the two different types of adhesive modules and potentially recapitulate the intermolecular interactions between Mfp3 and Mfp5 found in natural adhesion systems[2] (FIG. 1c-d).

Figure 17A:
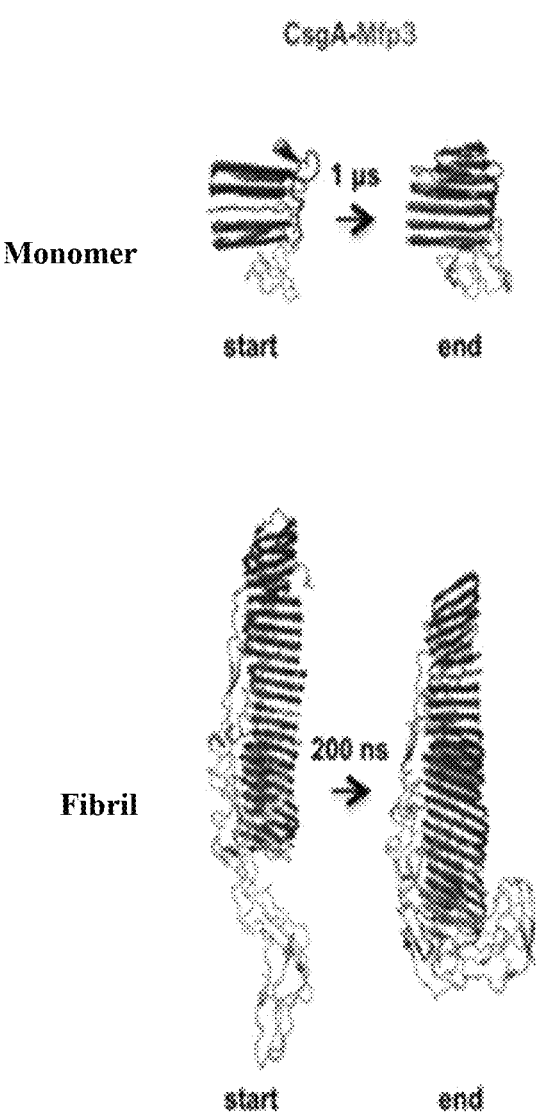
FIGS. 17A-17C are a comparison of monomer, individual fibril and co-assembled fibril structures before and after molecular-dynamics simulations for modified CsgA-Mfp3, Mfp5-CsgA, and (CsgA-Mfp3)-(Mfp5-CsgA) copolymer constructs.
Figure 17B:
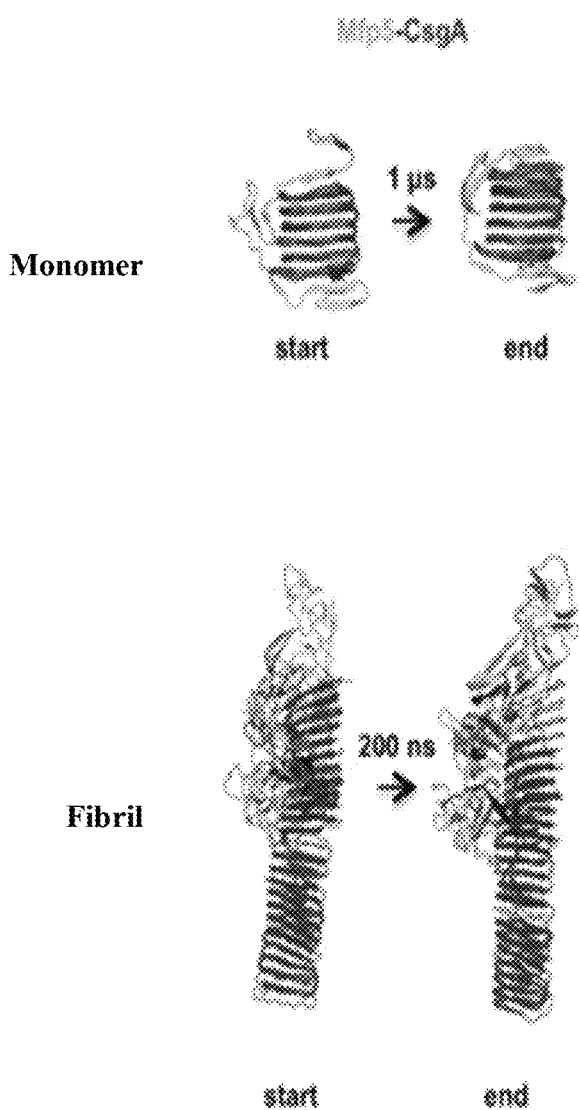
Figure 17C:
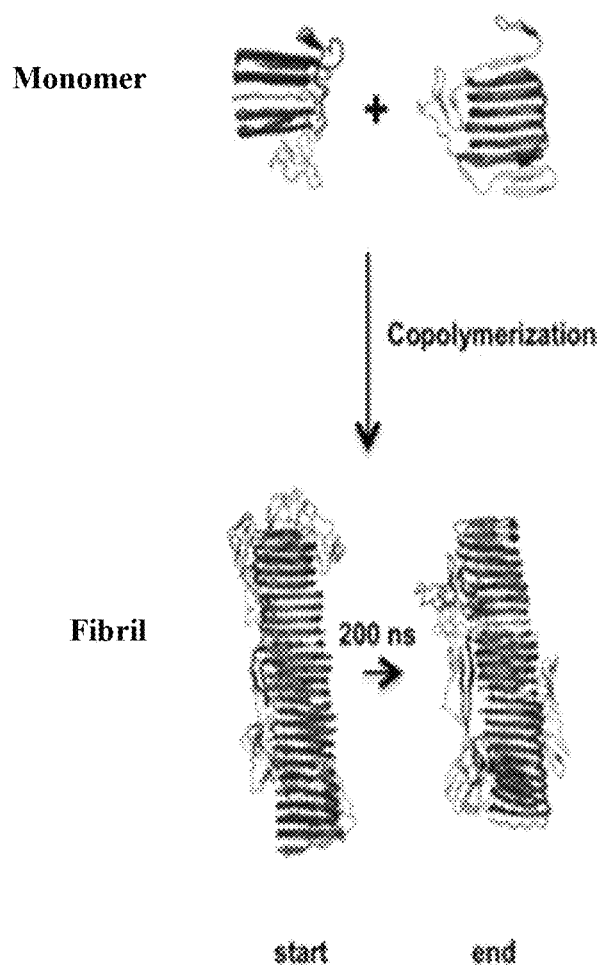

To investigate whether the presence of a disordered Mfp domain would affect the overall structure of CsgA amyloid cores, we built molecular-dynamics models representing both monomeric and fibrillar states of the CsgA-Mfp3, Mfp5-CsgA and (CsgA-Mfp3)-co-(Mfp5-CsgA) copolymer constructs (FIG. 17). Simulations of the monomeric proteins (1 μs) and the fibrillar states (200 ns) indicated that the core amyloid structure does not significantly diverge from that of a prototypical amyloid structure when the disordered domains are present (FIG. 17). These results suggest that CsgA-Mfp3 alone, Mfp5-CsgA alone and copolymers of the two fusion proteins should form stable amyloid structures dominated by the CsgA domains, with the highly disordered Mfp domains displayed external to the amyloid core in all cases (FIG. 17a-c) and potentially interacting with each other in the copolymer construct (FIG. 17c).

Figures 18A, 18B:
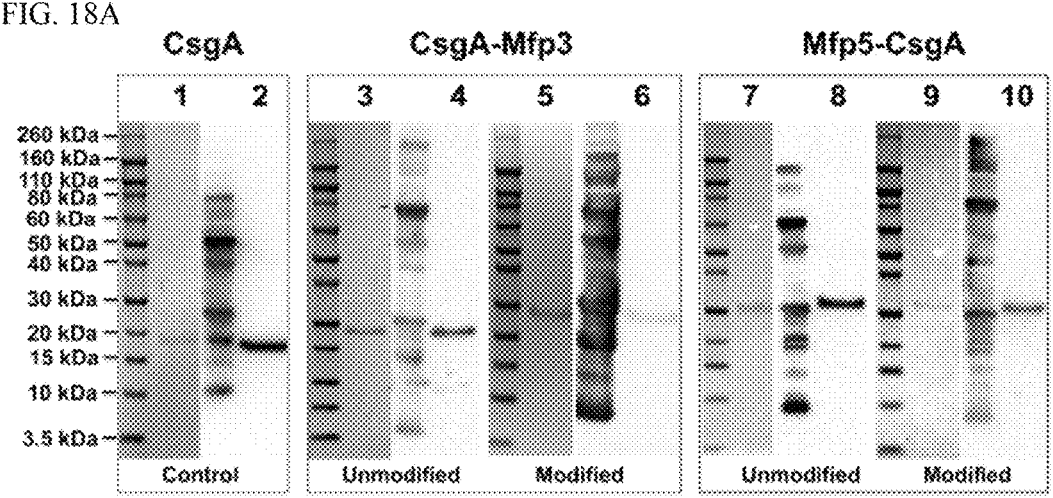

Genes encoding the designed proteins were appended with C-terminal polyhistidine tags and then expressed in *E. coli*, followed by purification under combined denaturing/non-denaturing conditions by cobalt-affinity chromatography. An additional modification step (conversion of tyrosine to Dopa by the enzyme tyrosinase) was carried out under non-denaturing conditions before eluting proteins from the cobalt resin column. For comparison, we also purified the adhesive proteins without the additional modification step. CsgA-Mfp3 (unmodified and modified) and Mfp5-CsgA (unmodified and modified) migrated as single bands at ~28.5 kDa and ~32 kDa, respectively, under SDS-polyacrylamide gel electrophoresis (SDSPAGE), in contrast with the single band at ~17 kDa for CsgA (FIG. 18a). All bands were specifically recognized by anti-His antibodies (FIG. 18a). No clear differences were detected between the band positions of the unmodified and modified versions of the same protein based on SDS-PAGE and Western blotting (FIG. 18a). However, more accurate molecular weight (MW) assessment by matrix-assisted laser desorption ionization (MALDI)-time of-flight (TOF) showed higher molecular weights in the modified adhesive proteins (compared with their unmodified counterparts), which we attribute to the conversion of tyrosine residues into Dopa with tyrosinase modification (FIG. 18b and FIG. 22a-f). Furthermore, based on MALDI-TOF spectra, we found that adhesive proteins collected from borate buffer had higher MWs than those collected from acid solutions, likely due to the formation of diol-borate bonds between Dopa and borate[22], thus confirming successful modification of the adhesive proteins (FIG. 22a-f). In addition, Dopa residues were detected in mature hybrid amyloid fibers with nitroblue tetrazolium (NBT) staining assay (FIG. 18c). Specifically, we found that only the modified samples turned purple with the NBT assay due to redox-cycling of Dopa residues[23] (FIG. 18c). Further quantitative analysis by acid-borate difference spectrum (ABDS) analysis[22] revealed conversion percentages from tyrosine to Dopa of 64.8% and 56.0% for modified CsgA-Mfp3 and Mfp5-CsgA, respectively (FIG. 18d and FIG. 23), in close agreement with results obtained from amino acid analysis (FIG. 18d).

Figure 18E:
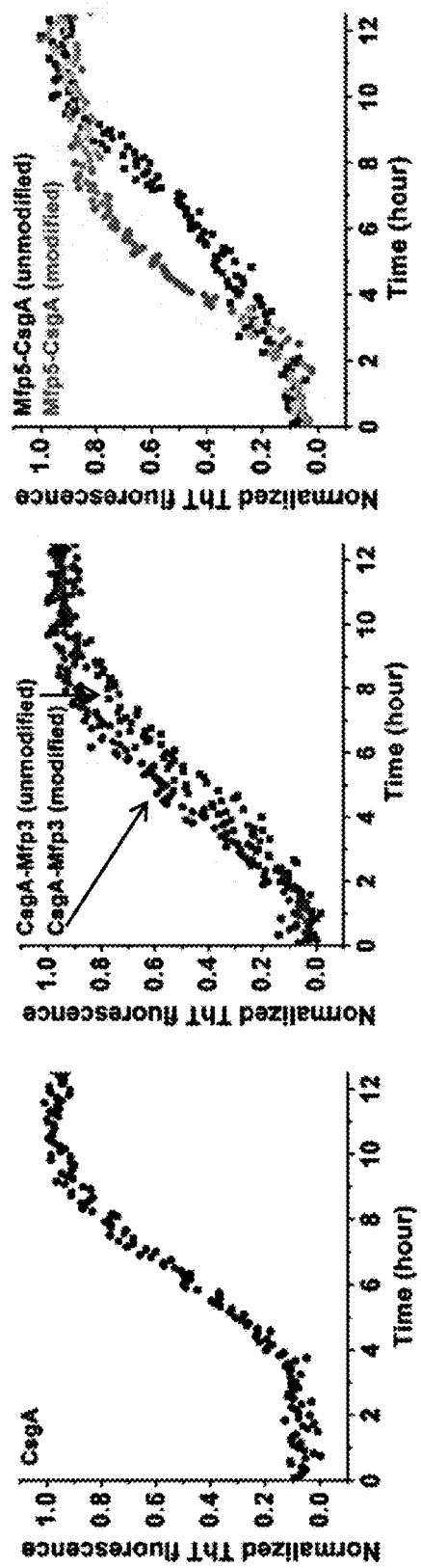

Our hybrid adhesive proteins formed hierarchically self-assembled structures (FIG. 1d). Immediately after elution from cobalt resin columns, solutions containing CsgA-Mfp3 (unmodified or modified) or Mfp5-CsgA (unmodified or modified) were clear with no evidence of aggregation. However, after about two hours of incubation at ambient conditions, the solutions became opaque and noticeably viscous. Transitions of soluble proteins to insoluble amyloid aggregates can be monitored using Thioflavin T (ThT), an amyloid-specific dye commonly used to assay amyloid formation[24]. The ThT fluorescence of all samples followed a sigmoidal curve with distinguishable lag, growth, and stationary phases (FIG. 18e). However, the polymerization lag phases for CsgA-Mfp3 (unmodified or modified) and Mfp5-CsgA (unmodified or modified) were typically shorter than that for CsgA, suggesting that the fusion of Mfp domains to CsgA accelerates amyloid formation. This observation is consistent with the fly-casting mechanism, which postulates that a relatively unstructured protein can have a greater "capture radius" and thus enhance the rate of intermolecular association[25,26]. In addition, partial conversion of tyrosine residues into Dopa residues in tyrosinase-modified proteins shortened the time required to reach stationary phase, implying a higher fiber formation rate in modified proteins (FIG. 18e).

Figure 18F:
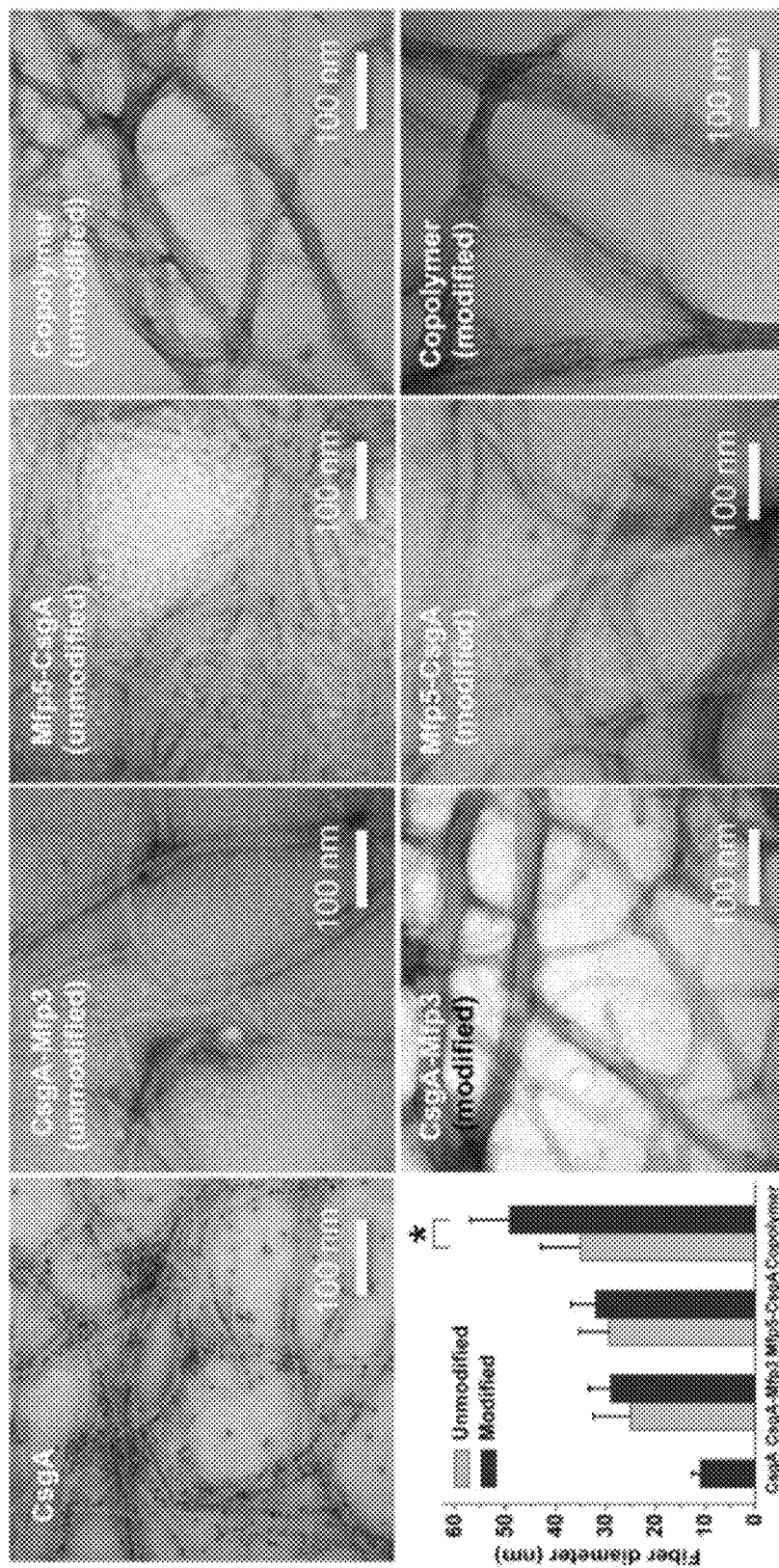

The formation of long fibers was confirmed for all proteins under transmission electron microscopy (TEM), with no apparent differences in general morphology and fiber length (FIG. 18f). However, the mean diameters of the three types of functionalized fibers in both unmodified and modified forms were three to five times larger than that of CsgA (FIG. 18f). In particular, the mean diameter of modified (CsgA-Mfp3)-(Mfp5-CsgA) copolymer fibers reached as high as ~50 nm, which was noticeably larger than fibers composed of the unmodified copolymer as well as both unmodified and modified samples of CsgA-Mfp3 and Mfp5-

CsgA. Note that all instances of the (CsgA-Mfp3)-co-(Mfp5-CsgA) copolymer described from here on were assembled from 1:1 molar ratios of CsgA-Mfp3 to Mfp5-CsgA, unless otherwise noted. We believe that this increased diameter likely arises from additional intermolecular associations between the Mfp3 and Mfp5 domains in the copolymer construct. Circular dichroism (CD) studies indicated that the fibers were generally rich in beta-sheet secondary structure in solution, in agreement with molecular-dynamics modeling (FIG. 17). Interestingly, all of the unmodified or modified proteins, either upon incubation of freshly made soluble proteins over existing nanofiber seeds or upon incubation at high solution concentrations, assembled into larger fiber bundles and even thick hierarchical films composed of fibrils.

One remarkable feature of the adhesive fibers is that they all exhibited intrinsic fluorescence signatures in the visible spectrum range (FIG. 19a). Adhesive biomaterials that display intrinsic fluorescence may be useful for biological and imaging applications, similar to photoluminescent materials[27]. The unmodified adhesive fibers displayed higher fluorescence intensities than their tyrosinase-modified counterparts when measured in bulk fiber bundles (FIG. 19a). These observations were in agreement with fluorescence quantum yields (Q (%)) determined by the Williams comparative method[28] (FIG. 19a). Among the unmodified adhesive fibers, Mfp5-CsgA had the highest Q value (4.2), followed by 3.9 for the (CsgA-Mfp3)-(Mfp5-CsgA) copolymer and 2.8 for CsgA-Mfp3. However, for the modified fibers, the Q values followed an opposite trend, with 1.9, 2.1 and 2.6 for Mfp5-CsgA, (CsgA-Mfp3)-(Mfp5-CsgA) copolymer and CsgA-Mfp3, respectively. Both unmodified and modified hybrid adhesive fibers had ~2-4 fold higher Q values than CsgA control fibers. Spectral analysis revealed that the excitation maxima for Mfp5-CsgA (unmodified or modified), CsgA-Mfp3 (unmodified or modified), (CsgA-Mfp3)-co-(Mfp5-CsgA) copolymer (unmodified or modified) and CsgA fibers was near 318, 312, 315 and 306 nm, respectively, while the emission maxima was close to 378 nm for all constructs (FIG. 4b). Interestingly, when excited at different wavelengths, the adhesive fibers emitted fluorescence that could be detected with a wide range of filters with fluorescence microscopy, ranging from blue to red (FIG. 11), in agreement with the spectral results (FIG. 4c). In addition, fluorescence was detected in aged solutions, but not in freshly made solutions, implying that fiber formation is a precondition for fluorescence (FIG. 19d).

Collectively, we suggest that electron delocalization via hydrogen bonds within ordered β-sheet structures[29] and the high percentage of aromatic side-chains may both contribute to the intrinsic fluorescence signatures of our hybrid adhesive fibers. The higher fluorescence intensity of unmodified Mfp5-CsgA may arise from its higher fluorescent aromatic residue content (12.5%) compared with CsgA-Mfp3 (10.8%) and CsgA (5.8%), respectively. Furthermore, the decrease in fluorescence intensity within modified fibers versus their unmodified counterparts might be associated with partial conversation of tyrosine residues to Dopa, as the fluorescence quantum yield of Dopa residue (0.09)[30] is lower than that of tyrosine (0.14)[31] in acid-neutral solutions and is further substantially reduced in conjugate base forms (for example, with deprotonation of the phenolic hydroxyl group)[30]. Decreased fluorescence in modified fibers might be also relevant to fluorescence quenching due to auto-oxidation or potential cross-linking[32].

Figure 20A:
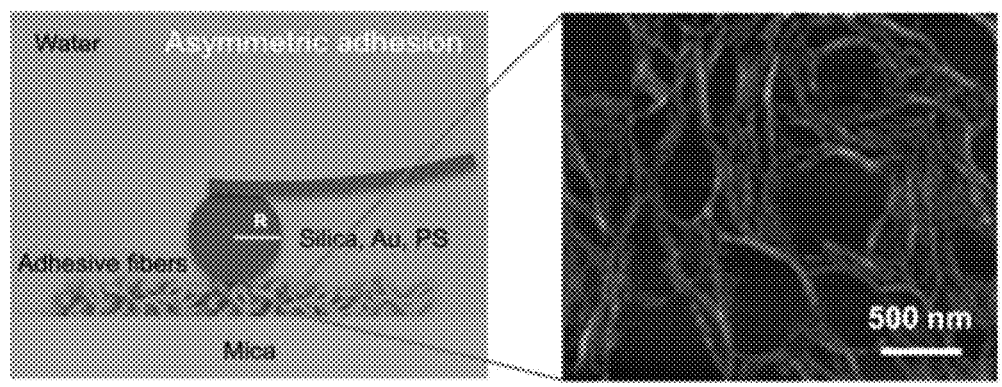

To assess the underwater adhesion performance of our engineered adhesive fibers, we used the atomic force microscopy (AFM) colloidal probe technique[33] (FIG. 20a). This technique essentially measures the asymmetric adhesion of fibers, which pre-bind firmly to mica and bind to the AFM tip surface temporarily during measurement. The AFM tips used in this study included silica, gold, and polystyrene (PS) surfaces, which were chosen as representative inorganic, metal and polymeric surfaces. Proteins were deposited and adsorbed on clean mica surfaces under buffered aqueous conditions with a wide range of pH values. Fibrous structures were found covering the mica surfaces after one hour of adsorption (FIG. 20a).

Figure 20B:
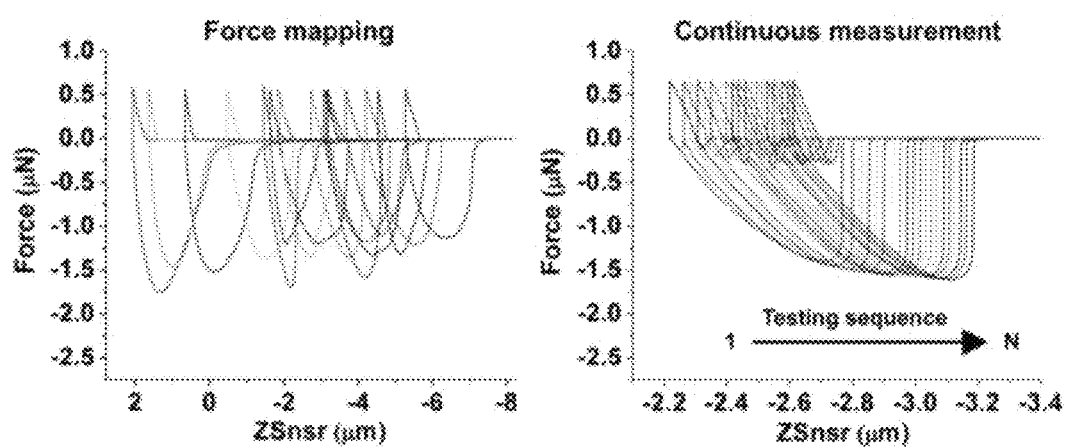
Figure 20C:
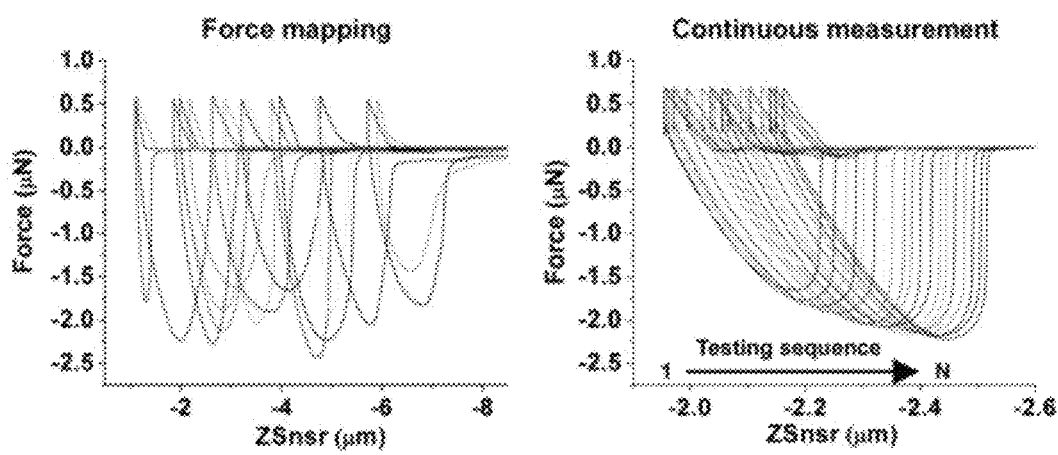

To provide a comprehensive understanding of the adhesive behavior of our fibers, we performed both force mapping mode and continuous measurement mode studies. The mapping mode was based on measuring adhesion at random fiber spots on the mica surface with a scanning range of ~20-100 μm, thus providing a diverse dataset (FIGS. 20b and 20c). The continuous measurement mode enabled us to assess the cyclic behaviors of contacts between fibers and AFM tip surfaces by performing adhesion tests at a specific fiber spot with a total of 20 continuous measurements (FIGS. 20b and 20c). Data obtained through both measurement modes were consistent with each other; thus, we concluded that our adhesion fibers exhibited repeatable adhesion properties (rather than just a single adhesion event) and that the adhesion characteristics were indeed dependent on the specific adhesive fibers studied (FIGS. 20b, 20c and 21).

The stability of adhesion was assessed by performing adhesion measurements on unmodified and modified Mfp5-CsgA fibers under aqueous conditions with different pH values (pH=2.5, 5.0, 7.0, and 10.0) (FIG. 20d). Both unmodified and modified Mfp5-CsgA fibers maintained adhesion under acidic and neutral conditions (pH 2.5-7.0). Surprisingly, both modified and unmodified Mfp5-CsgA fibers still exhibited considerable levels of adhesion even under basic conditions (pH=10.0). Similar trends were observed for the other types of fibers (data not shown). These data contrast with previous findings that reported soluble and non-fibrous *Mytilus edulis* foot protein-5 (Mefp5) had a 3-fold lower adhesion energy[34] at pH=5.5 versus pH=2.6 as well as studies showing that adhesion by Mfp3 and Mfp5 is almost completely abolished when exposed to slightly basic conditions (pH≥7.5)[34,35]. These results suggest that our adhesive fibers generally exhibit better tolerance to auto-oxidation compared with previous reports on Mfps alone, possibly arising from the protective effects of hydrophobic aromatic residues as well as the general hydrophobic features of amyloid fibers[36,37]. In particular, partial conversion (~50%-70%) of tyrosine to Dopa in our adhesive proteins may resemble the so-called Mfp3 "slow" variant, which is comprised of both Dopa and more hydrophobic tyrosine residues and was recently reported to preserve significant levels of adhesion even at pH 7.0 due to hydrophobicity compensation for Dopa oxidation[35].

We further compared the adhesive behaviours of different functionalized adhesive fibers (FIG. 21). For the same protein, tyrosinase-modified fibers always displayed higher adhesion (at least a 2-3 fold increase) compared with unmodified fibers (FIG. 21a), independent of the AFM tips (silica, gold and PS) that were applied. These data suggest that Dopa residues in the self-assembled nanofibers contribute significantly to underwater adhesion. However, unmodified fibers also displayed higher adhesion than the CsgA control, implying that features of Mfp domains other than Dopa are able to participate in underwater adhesion (FIG. 21a). Further comparison of different modified adhesive fibers measured under the same conditions with the same type of tips indicated that adhesion performance followed the general trend of (CsgA-Mfp3)-(Mfp5-CsgA) copolymer>Mfp5-CsgA>CsgA-Mfp3>CsgA, independent of the AFM tips that were used. Among the three tips, the most obvious trend was observed with silica. Testing with silica tips showed very high underwater adhesion for modified Mfp5-CsgA and (CsgA-Mfp3)-co-(Mfp5-CsgA) copolymer fibers (FIGS. 20b, 20c and 21a). Specifically, modified Mfp5-CsgA fibers had a normalized adhesion force (Force/Radius, F/R) and adhesion energy ($E_{ad}$) of 136 mN/m and 14.4 mJ/m$^2$, respectively. Of note, the adhesion energy of Mfp5-CsgA fibers was 3-fold greater than the reported adhesion energy for recombinant Mfp5 alone under the same conditions[10], and was 3-fold higher than Mefp5 (*Mytilus edulis* foot protein 5), the most adhesive mussel protein reported so far, at pH~5.0[34].

Figure 21A:
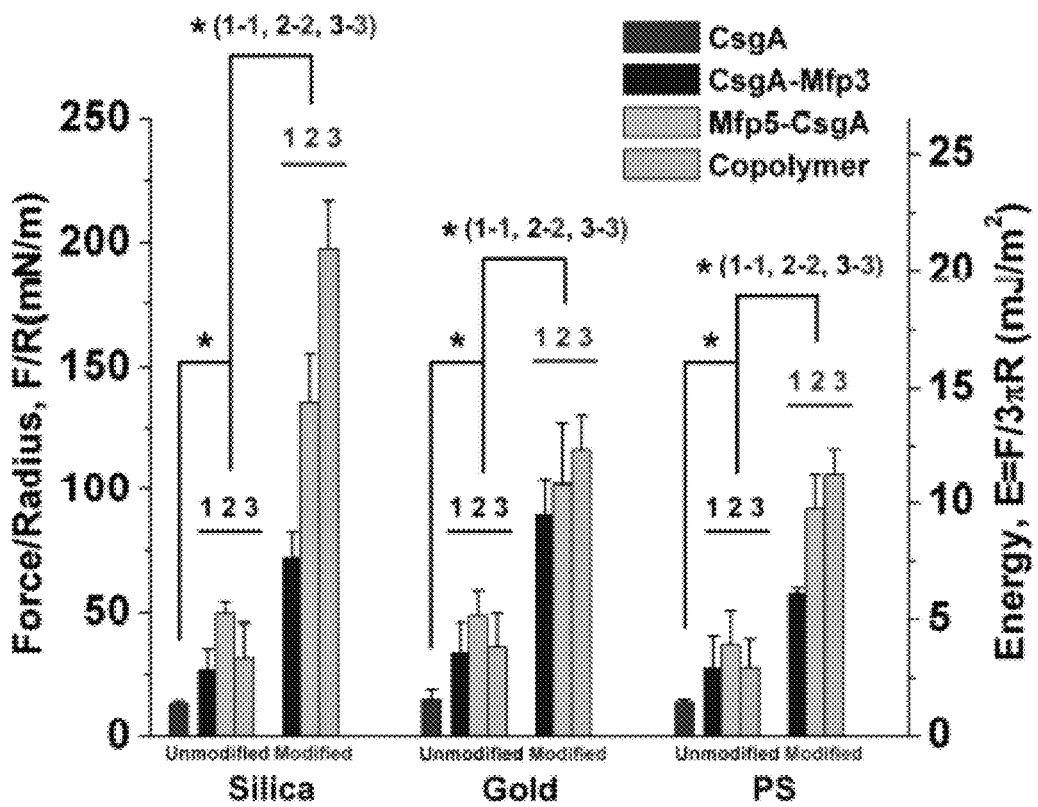
FIGS. 21A-21J show the comparison of the adhesion performances of different functionalized adhesive fibers with different AFM tips.
Figure 25B:
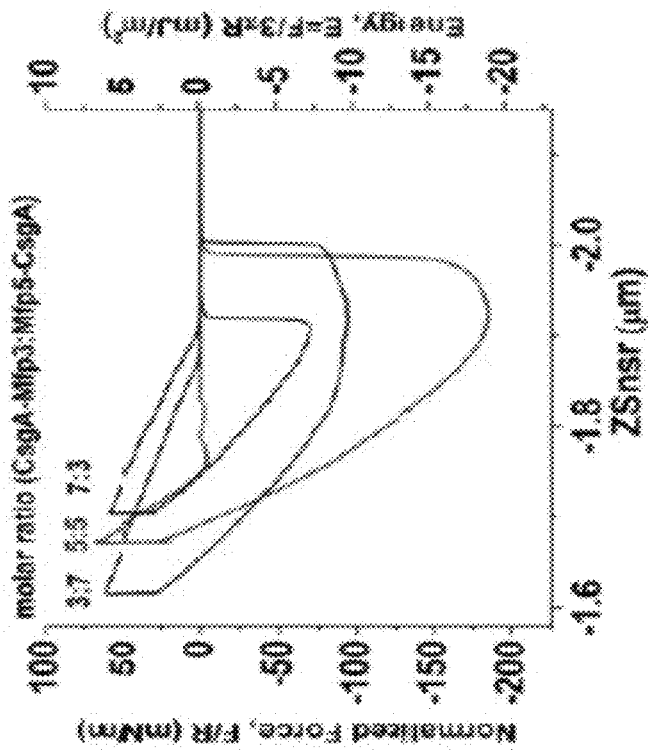
FIGS. 25A-25B show an adhesion performance comparison between copolymer fibers composed of the two monomer proteins (CsgA-Mfp3 and Mfp5-CsgA) with various molar ratios.
Figure 25A:
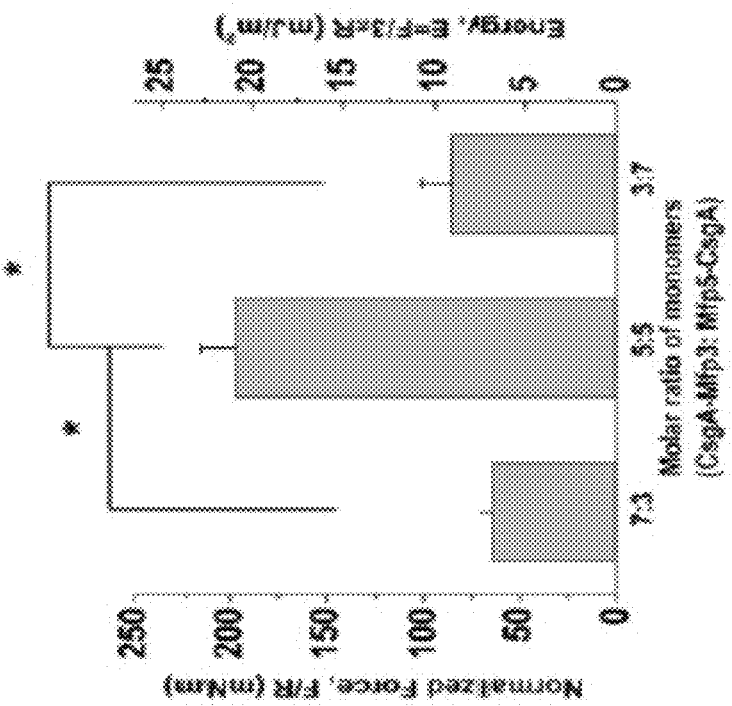
Figure 26C:
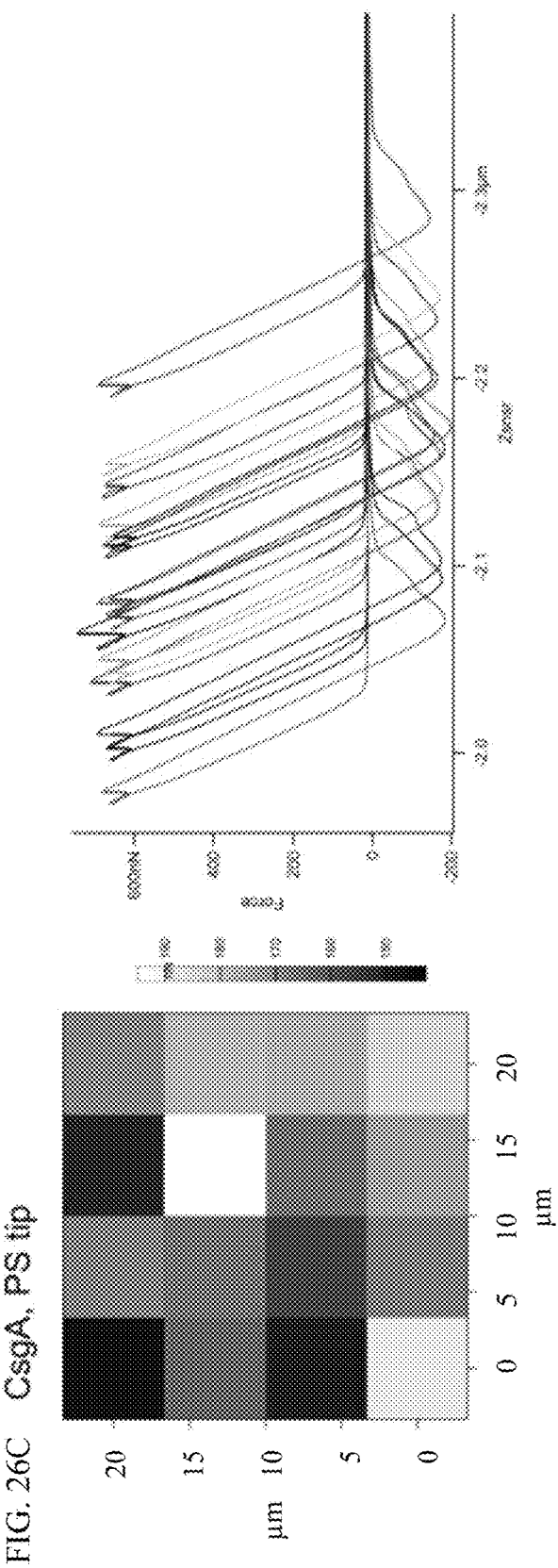
Figure 29C:
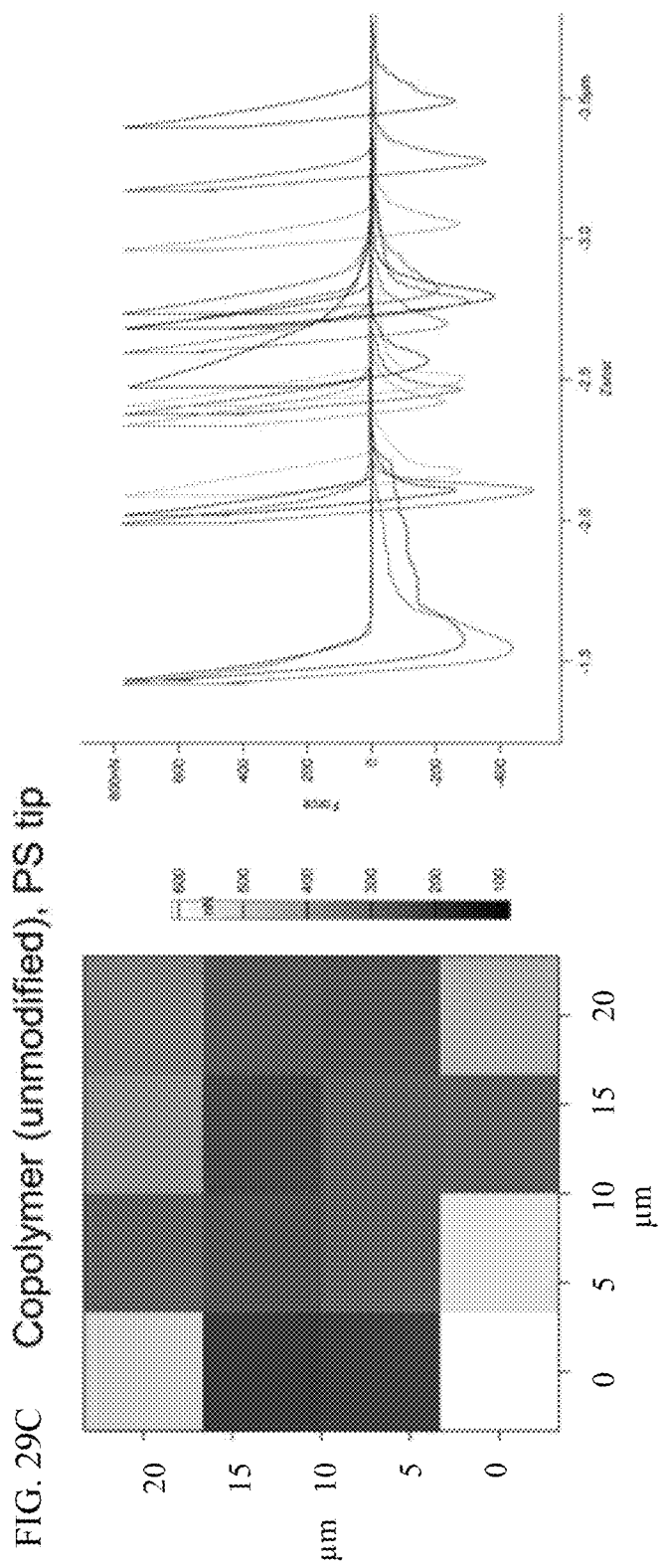
Figure 30B:
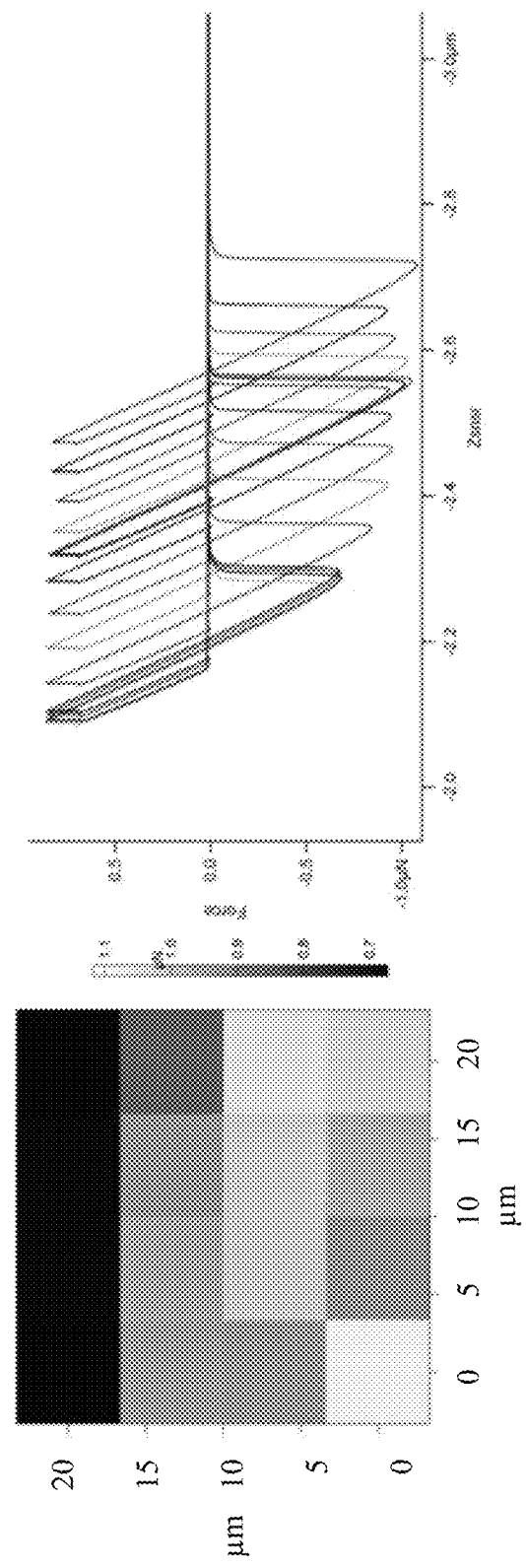

Interestingly, the (CsgA-Mfp3)-co-(Mfp5-CsgA) copolymer (1:1 ratio) had significantly higher adhesion than Mfp5-CsgA and CsgA-Mfp3 when measured with silica tips (P<0.01), Specifically, (CsgA-Mfp3)-co-(Mfp5-CsgA) copolymer fibers had F/R=197.5 mN/m and Ead=20.9 mJ/m$^2$. These values were ~2-3-fold higher than modified CsgA-Mfp3 measured under the same conditions (FIG. 21a). Moreover, copolymers with a CsgA-Mfp3:Mfp5-CsgA monomer ratio of 1:1 displayed higher adhesion than copolymers assembled from CsgA-Mfp3:Mfp5-CsgA monomer ratios of 3:7 or 7:3 (Supplementary FIG. 25). To our knowledge, (CsgA-Mfp3)-co-(Mfp5-CsgA) copolymer (1:1 ratio) fibers exhibited the strongest underwater adhesion among all known bio-derived and bio-inspired protein-based underwater adhesives reported to date2,5,34,38. We hypothesize that amyloid fiber structures enable large surface areas for contact, with multiple disordered Mfp domains on fiber surfaces likely interacting to achieve enhanced ultra-strong underwater adhesion. This hypothesis is supported by the larger mean fiber diameters of copolymer based fibers compared with fibers assembled from the individual proteins, as noted earlier (FIG. 18f).

Figure 21B:
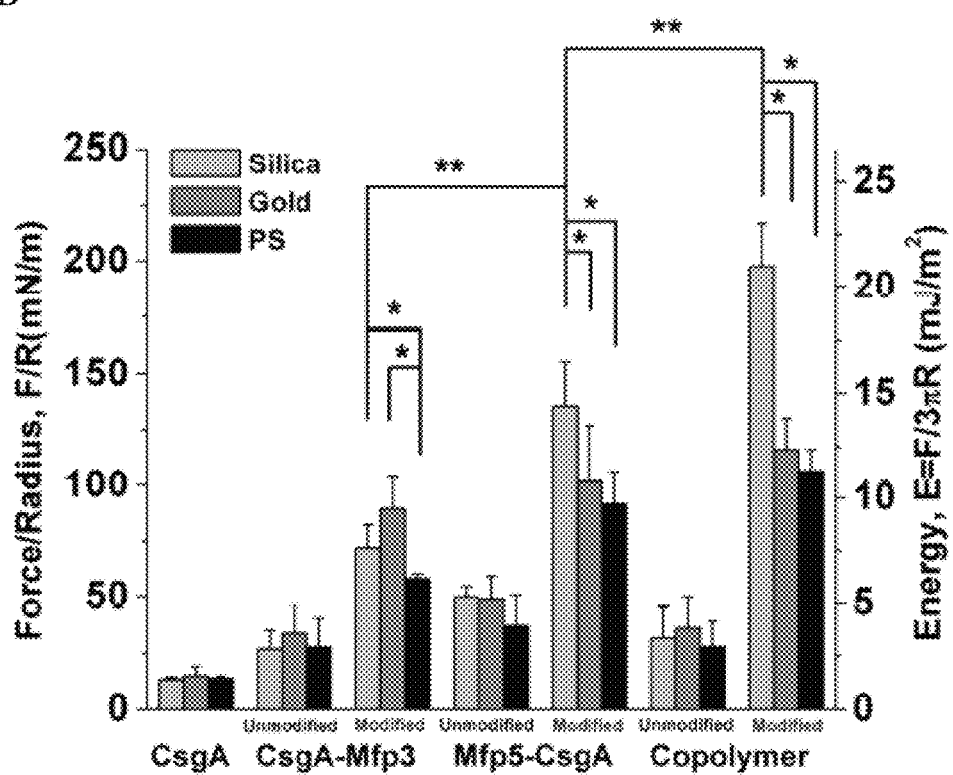
Figure 21D:
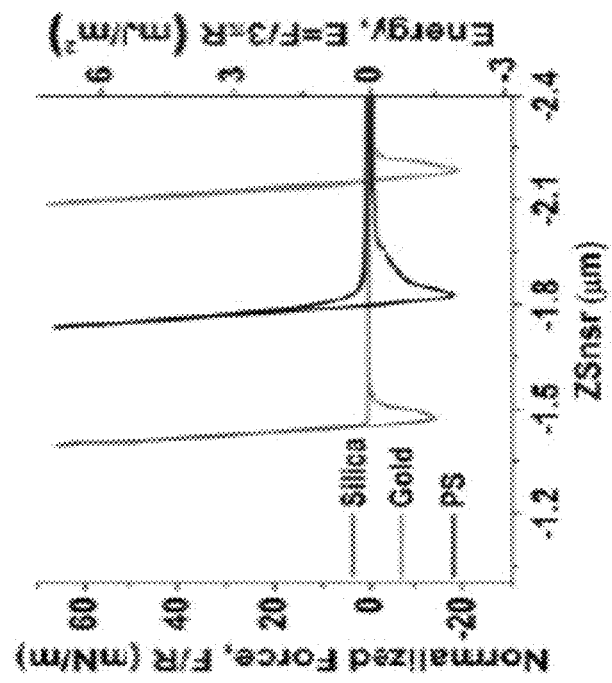
Figure 21C:
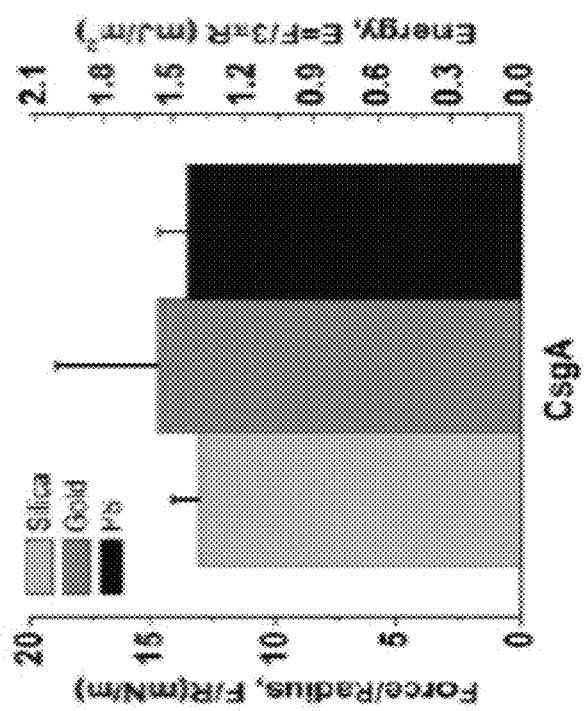
Figures 21E, 21F:
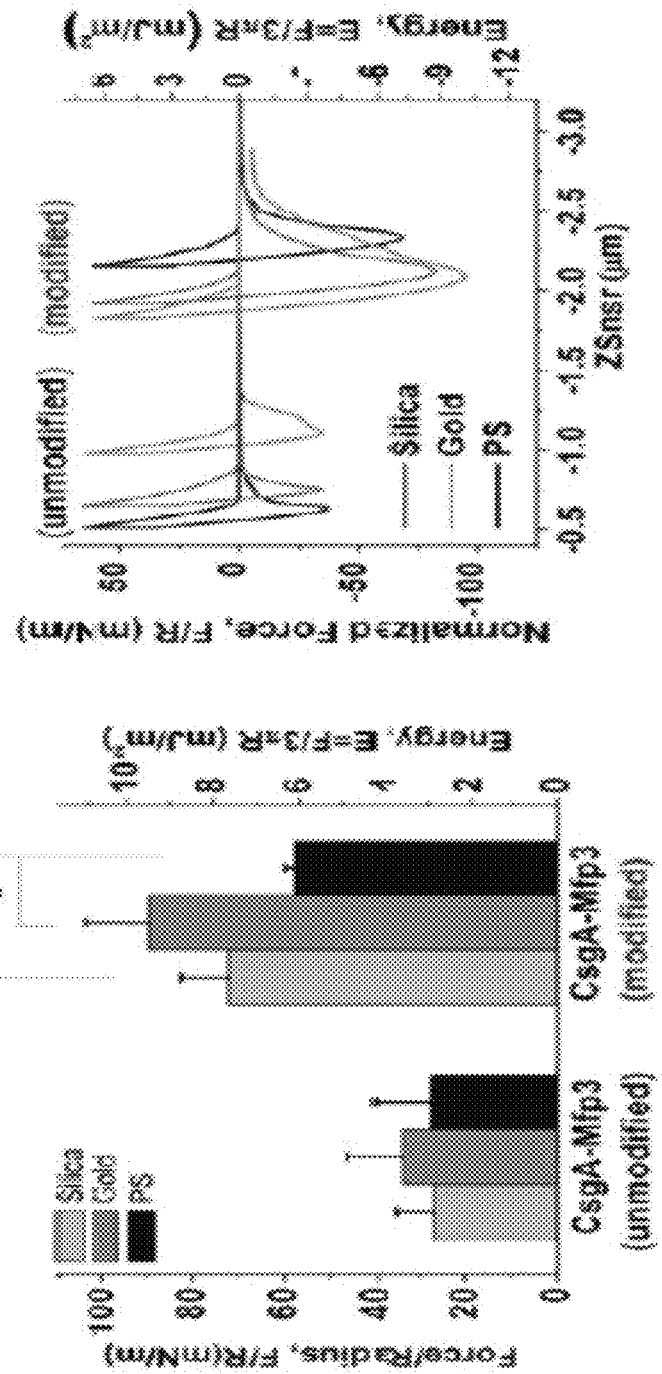
Figure 21H:
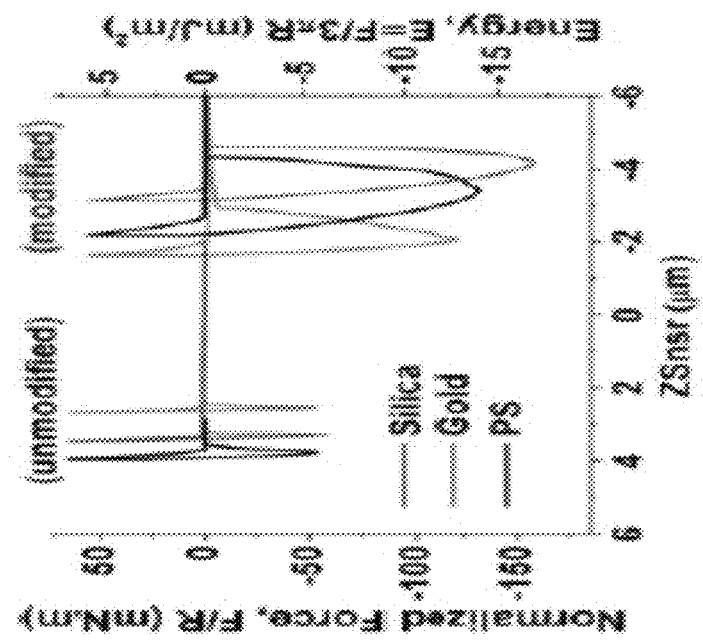
Figure 21G:
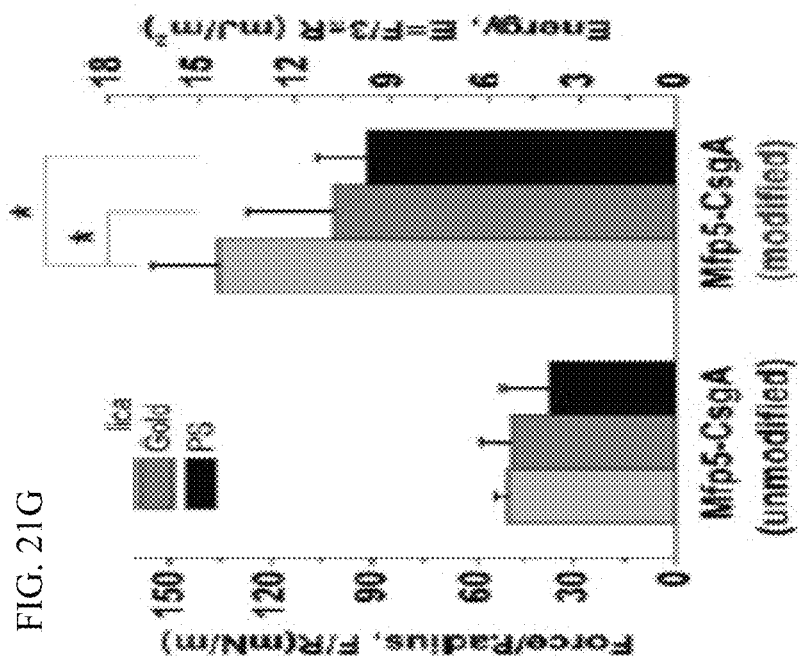
Figure 21J:
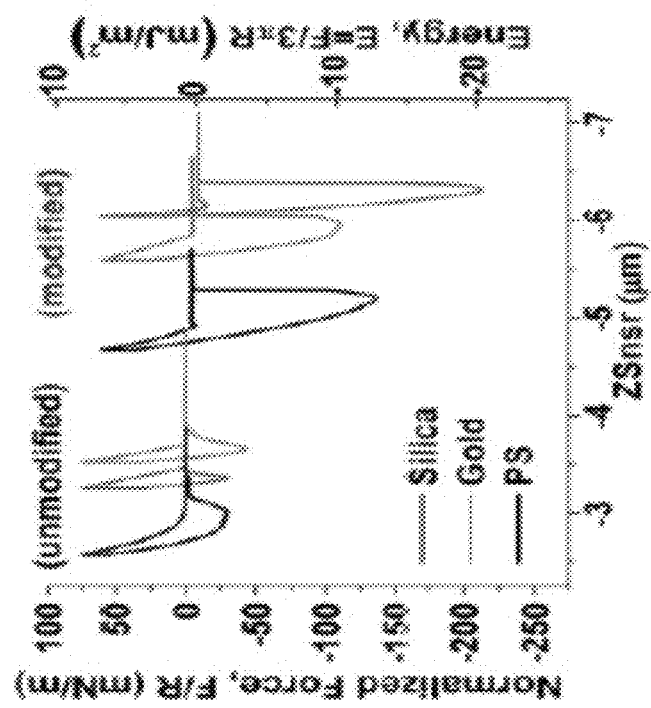
Figure 21I:
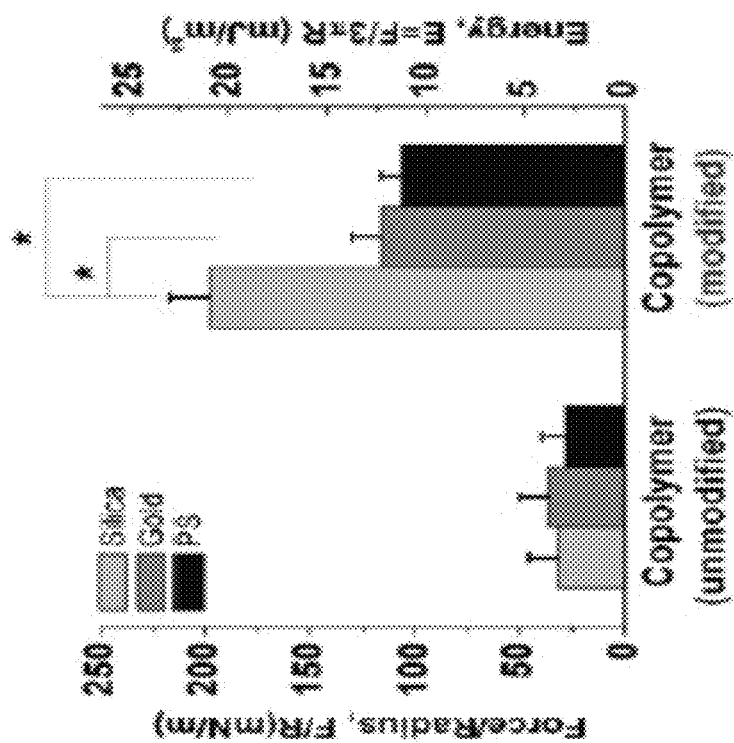
Figure 22A:
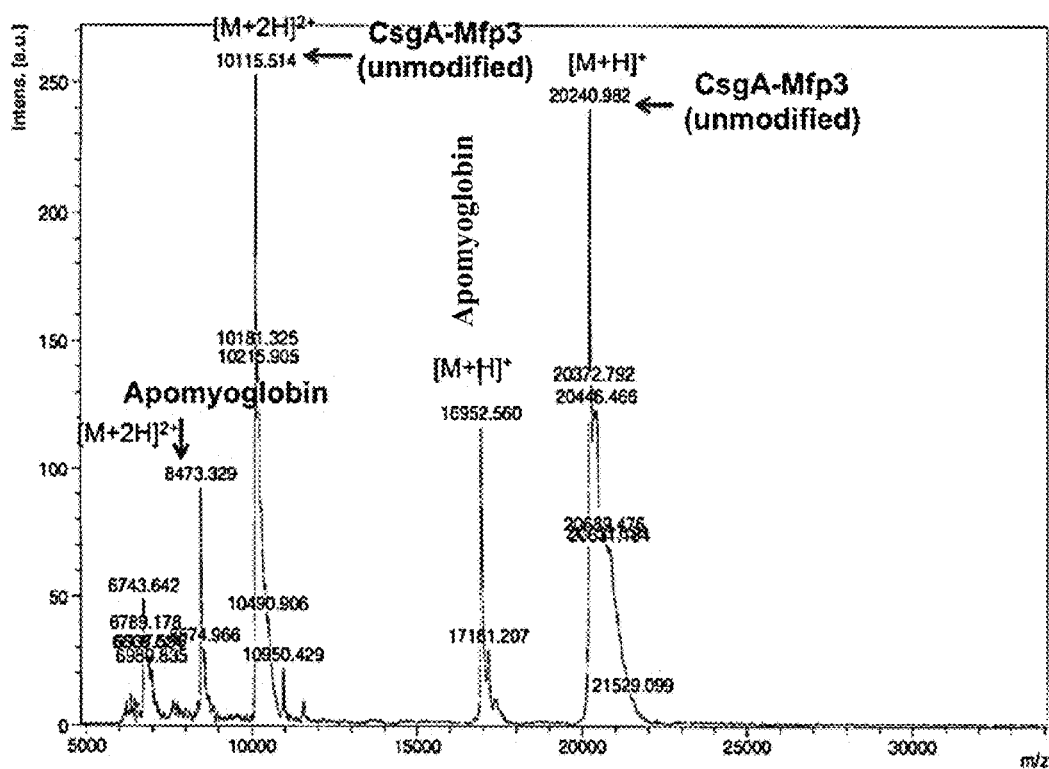
FIGS. 22A-22F show the molecular weight (MW) of adhesive proteins determined by MALDI-TOF mass spectrometry analysis.
Figure 22B:
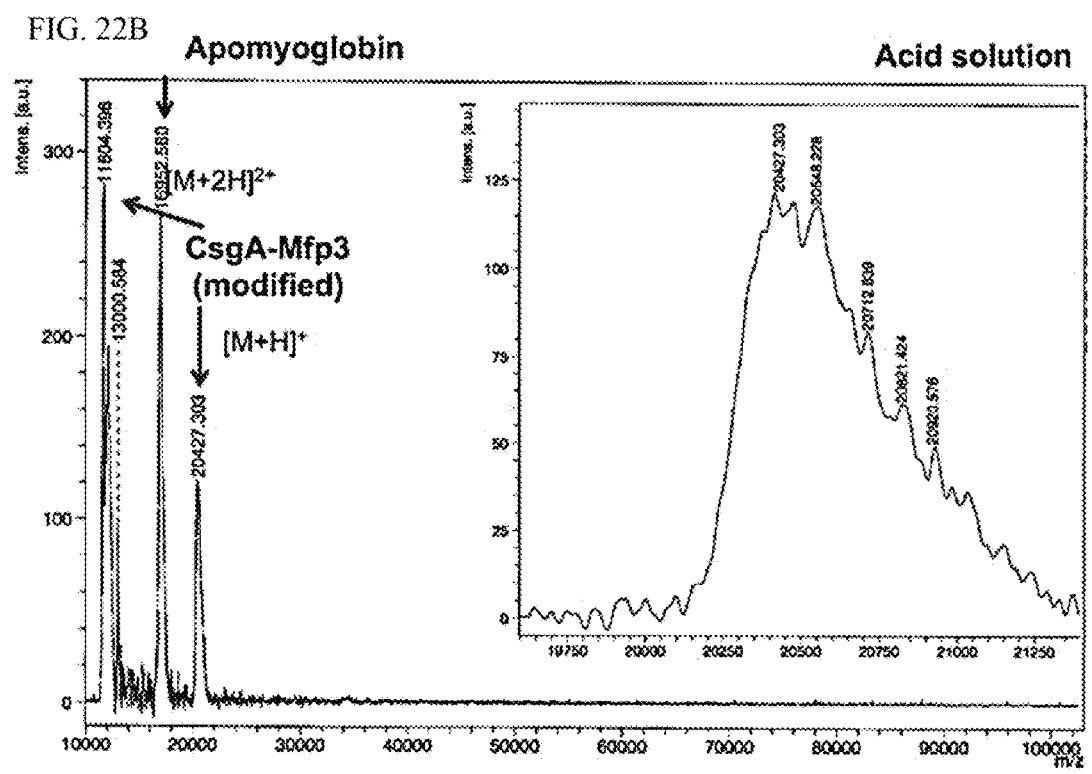
Figure 22C:
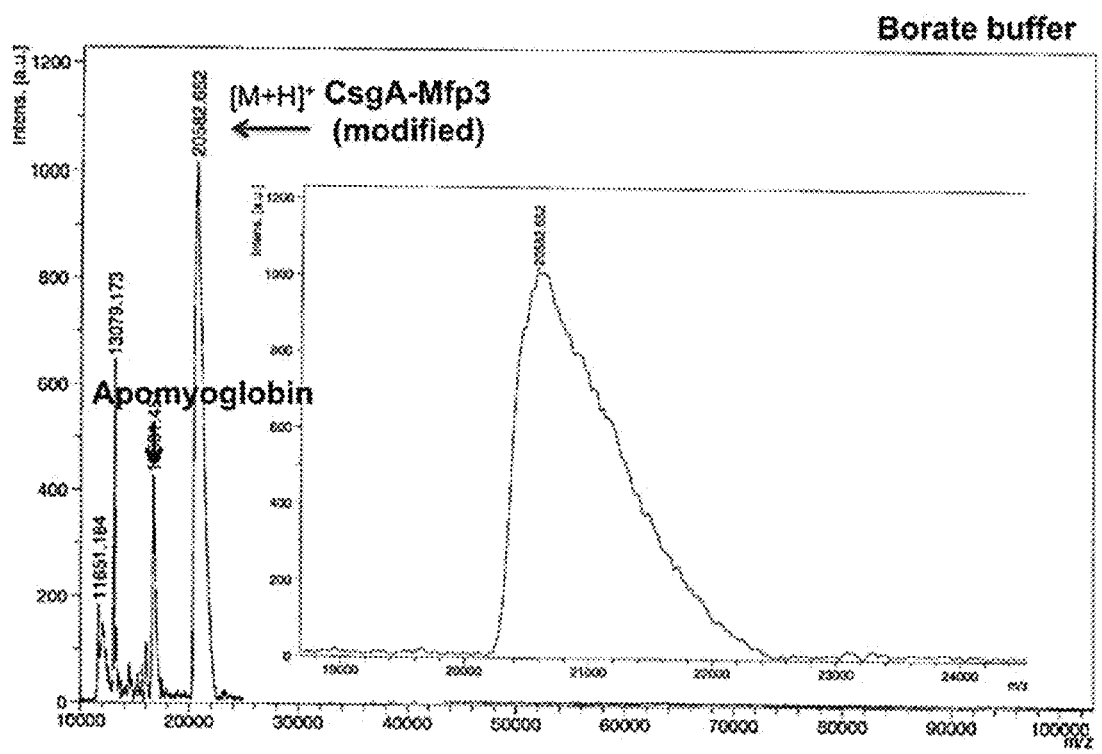
Figure 22D:
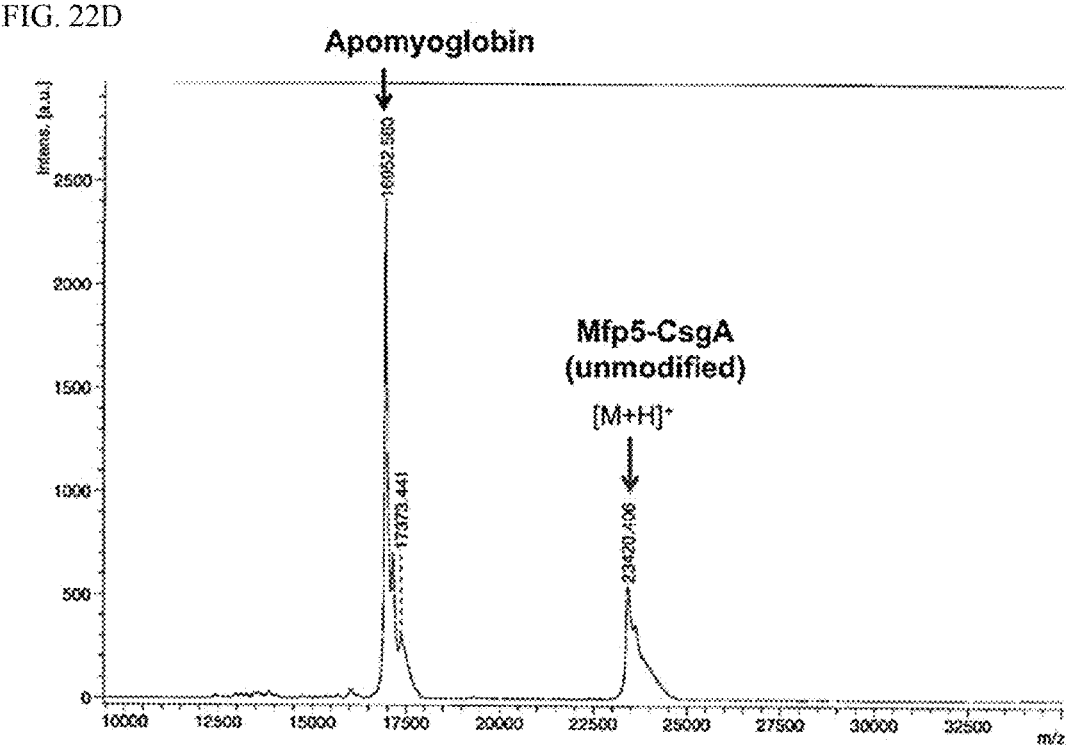
Figure 22E:
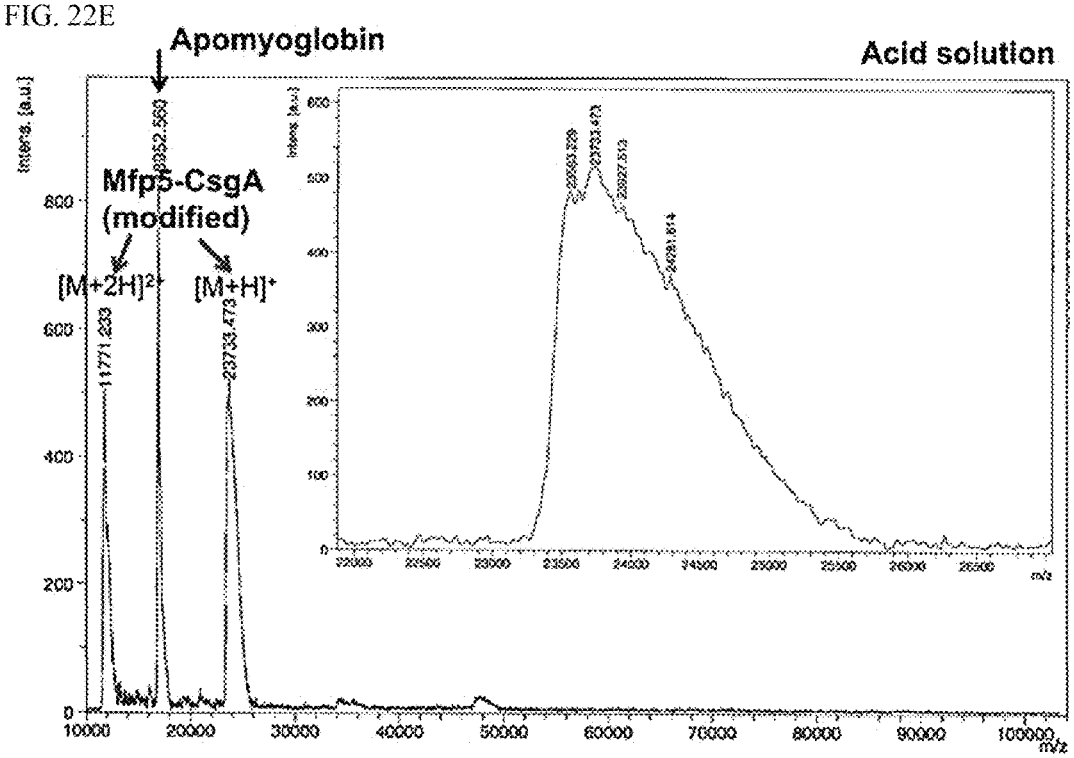
Figure 22F:
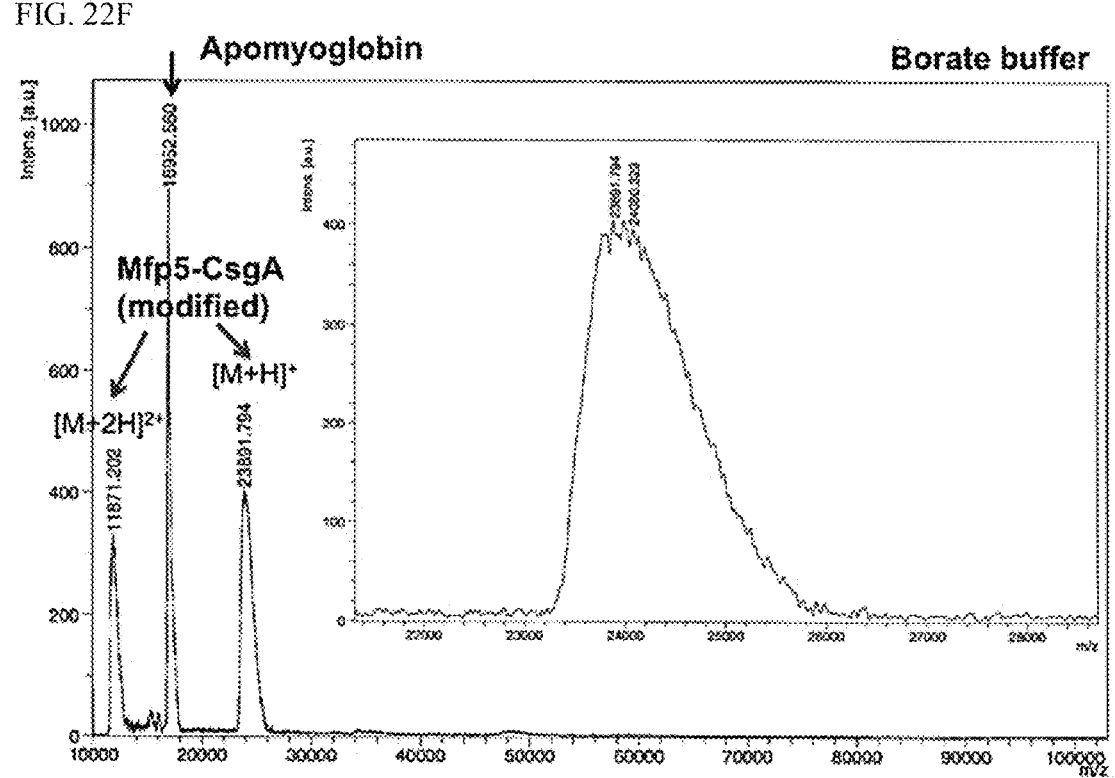

We compared how different AFM tips with varied surface energies affect the adhesive behaviours of the same type of proteins (FIG. 21b). Among all of the adhesive proteins studied, significant adhesion differences between tips were only found in tyrosinase-modified samples of CsgA-Mfp3, Mfp5-CsgA and (CsgA-Mfp3)-co-(Mfp5-CsgA) copolymer (1:1 ratio) (FIG. 21b and Supplementary FIG. 21). Specifically, for modified CsgA-Mfp3, the general trend of adhesion was silica≈gold>PS (P<0.05). For modified Mfp5-CsgA and (CsgA-Mfp3)-co-(Mfp5-CsgA) copolymer (1:1 ratio), the trend was silica>gold≈PS (P<0.05). Both CsgA-Mfp3 and Mfp5-CsgA have basic pIs (~9.0-9.4) and are therefore positively charged at acidic and neutral conditions and can effectively bind to negatively charged SiO2 surfaces. Hydrogen bonding (between hydroxyl or amine groups on proteins and the oxygen atoms on $SiO_2$), bidentate Hbonding by Dopa, or hydrogen bonds coupled with coordinate bonds between Dopa and silica could contribute to the strong adhesion of fibers towards $SiO_2$ surfaces[38-40]. In contrast, the adhesion of fibers to polystyrene and gold surfaces could be mainly due to hydrophobic interactions, with additional cation-π interactions or π-π interactions likely associated with PS surfaces[38,40]. Previous studies in which adhesion was measured with a surface force apparatus (SFA) revealed that non-fibrous Mfp3 and Mfp5 molecules exhibited the highest adhesion to PS among four substrates (silica, PS, mica and PMMA) with short contact times and had the same level of adhesion to silica and PS with longer contacts[38]. In contrast, we found that stronger adhesion was found with silica tips and tyrosinase-modified fibers. These observations suggest that, other than providing high surface area for contact, the amyloid domains of our adhesive fibers may modulate how the Mfp domains interact with the substrates and achieve different adhesion levels.

We have demonstrated a modular genetic strategy for designing a new generation of bio-inspired self-assembling underwater adhesives. Our hybrid adhesive fibers recapitulate features from two independent natural adhesive building blocks based on amyloids and Dopa-containing mussel-foot proteins. The resulting amyloid-based molecular materials have hierarchical fibrous structures and multi-functional properties, such as strong wet bonding strength, material robustness, enhanced stability, and unexpected intrinsic fluorescence, which are advancements upon current biomimetic and natural adhesives. In particular, the co-assembly of two hybrid proteins in a defined ratio led to engineered copolymer structures with ultra-strong underwater adhesion. The enhanced functional properties of the copolymer structures demonstrate the promise of mimicking natural molecular materials by engineering complex, multi-component, and self-assembling biomaterials.

References for Example 2

1 Dolgin, E. The sticking point. *Nature Medicine* 19, 124-125 (2013).
2 Lee, B. P., Messersmith, P. B., Israelachvili, J. N. & Waite, J. H. in *Annual Review of Materials Research* Vol. 41 99-132 (2011).
3 Brubaker, C. E. & Messersmith, P. B. The Present and Future of Biologically Inspired Adhesive Interfaces and Materials. *Langmuir* 28, 2200-2205, doi:10.1021/la300044v (2012).
4 Stewart, R. J., Ransom, T. C. & Hlady, V. Natural Underwater Adhesives. *Journal of Polymer Science Part B—Polymer Physics* 49, 757-771, doi:10.1002/polb.22256 (2011).
5 Stewart, R. J. Protein-based underwater adhesives and the prospects for their biotechnological production. *Applied Microbiology and Biotechnology* 89, 27-33, doi:10.1007/s00253-010-2913-8 (2011).
6 Yin, M., Yuan, Y., Liu, C. S. & Wang, J. Development of mussel adhesive polypeptide mimics coating for in-situ inducing re-endothelialization of intravascular stent devices. *Biomaterials* 30, 2764-2773, Doi:10.1016/j.Biomaterials.2009.01.039 (2009).
7 Brubaker, C. E., Kissler, H., Wang, L. J., Kaufman, D. B. & Messersmith, P. B. Biological performance of mussel-inspired adhesive in extrahepatic islet transplantation. *Biomaterials* 31, 420-427, doi:10.1016/j.biomaterials.2009.09.062 (2010).
8 Matos-Perez, C. R., White, J. D. & Wilker, J. J. Polymer Composition and Substrate Influences on the Adhesive Bonding of a Biomimetic, Cross-Linking Polymer. *Journal of the American Chemical Society* 134, 9498-9505, doi:10.1021/ja303369p (2012).
9 Shafiq, Z. et al. Bioinspired Underwater Bonding and Debonding on Demand. *Angewandte Chemie-International Edition* 51, 4332-4335, doi:10.1002/anie.201108629 (2012).
10 Hwang, D. S., Yoo, H. J., Jun, J. H., Moon, W. K. & Cha, H. J. Expression of functional recombinant mussel adhesive protein Mgfp-5 in *Escherichia coli*. *Applied and Environmental Microbiology* 70, 3352-3359, doi:10.1128/aem.70.6.3352-3359.2004 (2004).
11 Kamino, K., Nakano, M. & Kanai, S. Significance of the conformation of building blocks in curing of barnacle 12 Kamino, K. Underwater adhesive of marine organisms as the vital link between biological science and material science. *Marine Biotechnology* 10, 111-121, doi:10.1007/s10126-007-9076-3 (2008).

13 Anika S. Mostaert, S. P. J. in *The Functional Fold: Amyloid Structures in Nature* (ed Suzi Jarvis; Anika Mostaert) Ch. 8, 131-146 (Pan Stanford, 2012).

14 Barlow, D. E. et al. Characterization of the Adhesive Plaque of the Barnacle Balanus amphitrite: Amyloid-Like Nanofibrils Are a Major Component. *Langmuir* 26, 6549-6556, doi:10.1021/la9041309 (2010).

15 Wasmer, C. et al. Amyloid fibrils of the HET-s(218-289) prion form a beta solenoid with a triangular hydrophobic core. *Science* 319, 1523-1526, doi:10.1126/science.1151839 (2008).

16 Sawaya, M. R. et al. Atomic structures of amyloid cross-beta spines reveal varied steric zippers. *Nature* 447, 453-457, doi:10.1038/nature05695 (2007).

17 Knowles, T. P. J. & Buehler, M. J. Nanomechanics of functional and pathological amyloid materials. *Nature Nanotechnology* 6, 469-479, doi:10.1038/nnano.2011.102 (2011).

18 Knowles, T. P. et al. Role of intermolecular forces in defining material properties of protein nanofibrils. *Science* 318, 1900-1903, doi:10.1126/science.1150057 (2007).

19 Chapman, M. R. et al. Role of *Escherichia coli* curli operons in directing amyloid fiber formation. *Science* 295, 851-855 (2002).

20 Knowles, T. P. J., Oppenheim, T. W., Buell, A. K., Chirgadze, D. Y. & Welland, M. E. Nanostructured films from hierarchical self-assembly of amyloidogenic proteins. *Nature Nanotechnology* 5, 204-207, doi:10.1038/nnano.2010.26 (2010).

21 Li, C. X., Adamcik, J. & Mezzenga, R. Biodegradable nanocomposites of amyloid fibrils and graphene with shape-memory and enzyme-sensing properties. *Nature Nanotechnology* 7, 421-427, doi:10.1038/nnano.2012.62 (2012).

22 Waite, J. H. & Benedict, C. V. Assay of dihydroxyphenylalanine (dopa) in invertebrate structural proteins. *Methods in enzymology* 107, 397-413 (1983).

23 Paz, M., Flückiger, R., Boak, A., Kagan, H. & Gallop, P. M. Specific detection of quinoproteins by redox-cycling staining. *Journal of Biological Chemistry* 266, 689-692 (1991).

24 Wang, X., Zhou, Y., Ren, J.-J., Hammer, N. D. & Chapman, M. R. Gatekeeper residues in the major curlin subunit modulate bacterial amyloid fiber biogenesis. *Proceedings of the National Academy of Sciences of the United States of America* 107, 163-168, doi:10.1073/pnas.0908714107 (2010).

25 Shoemaker, B. A., Portman, J. J. & Wolynes, P. G. Speeding molecular recognition by using the folding funnel: The fly-casting mechanism. *Proceedings of the National Academy of Sciences of the United States of America* 97, 8868-+,doi:10.1073/pnas. 160259697 (2000).

26 Sugase, K., Dyson, H. J. & Wright, P. E. Mechanism of coupled folding and binding of an intrinsically disordered protein. *Nature* 447, 1021-U1011, doi:10.1038/nature05858 (2007).

27 Yang, J. et al. Development of aliphatic biodegradable photoluminescent polymers. *Proceedings of the National Academy of Sciences of the United States of America* 106, 10086-10091, doi:10.1073/pnas.0900004106 (2009).

28 Williams, A. T. R., Winfield, S. A. & Miller, J. N. Relative fluorescence quantum yields using a computer-controlled luminescence spectrometer. *Analyst* 108, 1067-1071 (1983).

29 del Mercato, L. L. et al. Charge transport and intrinsic fluorescence in amyloid-like fibrils. *Proceedings of the National Academy of Sciences of the United States of America* 104, 18019-18024, doi:10.1073/pnas.0702843104 (2007).

30 Smith, G. J. The fluorescence of dihydroxyphenylalanine: the effects of protonation-deprotonation. *Coloration Technology* 115, 346-349 (1999).

31 Chen, R. F. Fluorescence quantum yields of tryptophan and tyrosine. *Analytical Letters* 1, 35-42 (1967).

32 Al-Hilaly, Y. K. et al. A central role for dityrosine crosslinking of Amyloid-β in Alzheimer's disease. *Acta neuropathologica communications* 1, 83 (2013).

33 Leite, F. & Herrmann, P. Application of atomic force spectroscopy (AFS) to studies of adhesion phenomena: a review. *Journal of adhesion science and technology* 19, 365-405 (2005).

34 Danner, E. W., Kan, Y. J., Hammer, M. U., Israelachvili, J. N. & Waite, J. H. Adhesion of Mussel Foot Protein Mefp-5 to Mica: An Underwater Superglue. *Biochemistry* 51, 6511-6518, doi:10.1021/bi3002538 (2012).

35 Wei, W., Yu, J., Broomell, C., Israelachvili, J. N. & Waite, J. H. Hydrophobic enhancement of dopa-mediated adhesion in a mussel foot protein. *Journal of the American Chemical Society* 135, 377-383 (2012).

36 Wu, C., Lim, J. Y., Fuller, G. G. & Cegelski, L. Quantitative Analysis of Amyloid-Integrated Biofilms Formed by Uropathogenic *Escherichia coli* at the Air-Liquid Interface. *Biophysical journal* 103, 464-471 (2012).

37 Goulter-Thorsen, R., Taran, E., Gentle, I., Gobius, K. & Dykes, G. CsgA production by *Escherichia coli* O157: H7 alters attachment to abiotic surfaces in some growth environments. *Applied and environmental microbiology* 77, 7339-7344 (2011).

38 Lu, Q. et al. Adhesion of mussel foot proteins to different substrate surfaces. *Journal of* The Royal Society Interface 10, 20120759 (2013).

39 Yu, J. et al. Adaptive hydrophobic and hydrophilic interactions of mussel foot proteins with organic thin films. *Proceedings of the National Academy of Sciences* 110, 15680-15685 (2013).

40 Li, Y., Qin, M., Li, Y., Cao, Y. & Wang, W. Single molecule evidences for the adaptive binding of DOPA to different wet surfaces. *Langmuir* (2014).

41 Fowler, D. M., Koulov, A. V., Balch, W. E. & Kelly, J. W. Functional amyloid—from bacteria to humans. *Trends in Biochemical Sciences* 32, 217-224, doi:10.1016/j.tibs.2007.03.003 (2007).

42 Maji, S. K. et al. Functional Amyloids As Natural Storage of Peptide Hormones in Pituitary Secretory Granules. *Science* 325, 328-332, doi:10.1126/science.1173155 (2009).

43 Weber, W. & Fussenegger, M. Emerging biomedical applications of synthetic biology. *Nature Reviews Genetics* 13, 21-35, doi:10.1038/nrg3094 (2012).

44 Chen, A. Y. et al. Synthesis and patterning of tunable multiscale materials with engineered cells. *Nature materials* (2014).

45 Padilla, J. E., Colovos, C. & Yeates, T. O. Nanohedra: Using symmetry to design self assembling protein cages, layers, crystals, and filaments. *Proceedings of the*

46 Sinclair, J. C., Davies, K. M., Venien-Bryan, C. & Noble, M. E. M. Generation of protein lattices by fusing proteins with matching rotational symmetry. *Nature Nanotechnology* 6, 558-562, doi:10.1038/nnano.2011.122 (2011).
47 Lv, S. et al. Designed biomaterials to mimic the mechanical properties of muscles. *Nature* 465, 69-73, doi: 10.1038/nature09024 (2010).
48 Qian, L. & Winfree, E. Scaling up digital circuit computation with DNA strand displacement cascades. *Science* 332, 1196-1201, doi:10.1126/science.1200520 (2011).
49 Auslander, S., Auslander, D., Muller, M., Wieland, M. & Fussenegger, M. Programmable single-cell mammalian biocomputers. *Nature* 487, 123-+, doi:10.1038/nature11149 (2012).
50 Hong, S. H. et al. Cell-free protein synthesis from a release factor 1 deficient *Escherichia coli* activates efficient and multiple site-specific non-standard amino acid incorporation. *ACS synthetic biology* (2013).
51 Lajoie, M. J. et al. Genomically recoded organisms expand biological functions. *science* 342, 357-360 (2013).
52 Eswar, N. et al. Comparative protein structure modeling using Modeller. *Current protocols in bioinformatics*, 5.6. 1-5.6. 30 (2006).
53 Hwang, D. S. & Waite, J. H. Three intrinsically unstructured mussel adhesive proteins, mfp-1, mfp-2, and mfp-3: Analysis by circular dichroism. *Protein Science* 21, 1689-1695 (2012).
54 Lakowicz, J. R. *Principles of fluorescence spectroscopy*. (Springer, 2009).

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A fusion protein comprising
a mussel foot protein (Mfp) that is Mfp3 (SEQ ID NO:1 or SEQ ID NO:3) or Mfp5 (SEQ ID NO:2 or SEQ ID NO:4), respectively, and
CsgA of SEQ ID NO:7 or fragments thereof.

2. The fusion protein of claim 1, wherein the CsgA comprises one or more CsgA fragments selected from the group consisting of SEQ ID NOs: 13-18.

3. The fusion protein of claim 1, wherein the Mfp is Mfp3.

4. The fusion protein of claim 1, wherein the Mfp is Mfp5.

5. The fusion protein of claim 1, wherein the Mfp3 or Mfp5 is fused to the C-terminus of the CsgA, the Mfp3 or Mfp5 is fused to the N-terminus of the CsgA, or the Mfp3 or Mfp5 is fused within the CsgA.

6. The fusion protein of claim 1 comprising SEQ ID NO:9 (Mfp5-CsgA) or SEQ ID NO:8 (CsgA-Mfp3).

7. The fusion protein of claim 1, further comprising one or more polypeptides selected from fibronectin, histatin, and epidermal growth factor (EGF).

8. A fiber comprising at least one type of fusion protein of claim 1.

9. The fiber of claim 8, wherein the fiber comprises CsgA-Mfp3 and Mfp5-CsgA fusion proteins.

10. The fiber of claim 9, wherein the CsgA-Mfp3 and Mfp5-CsgA are present in a molar ratio of about 1:20 to 20:1 CsgA-Mfp3:Mfp5-CsgA, a molar ratio of about 1:15 to 15:1 CsgA-Mfp3:Mfp5-CsgA, a molar ratio of about 1:3 to 3:1 CsgA-Mfp3:Mfp5-CsgA, or a molar ratio of about 1:1 CsgA-Mfp3:Mfp5-CsgA.

11. The fiber of claim 8, wherein the fiber comprises a CsgA-Mfp3 fusion protein or a Mfp5-CsgA fusion protein.

12. An composition comprising one or more fusion proteins of claim 1.

13. A composition comprising one or more fusion proteins of claim 1, and a pharmaceutically acceptable carrier.

14. The composition of claim 13, further comprising an agent that promotes wound healing, wherein the agent that promotes wound healing is a growth factor or antibiotic.

* * * * *